United States Patent
Kinnings et al.

(10) Patent No.: US 12,260,935 B2
(45) Date of Patent: Mar. 25, 2025

(54) LIMIT OF DETECTION BASED QUALITY CONTROL METRIC

(71) Applicant: Illumina, Inc., San Diego, CA (US)

(72) Inventors: Sarah L. Kinnings, San Diego, CA (US); Cosmin Deciu, San Diego, CA (US); Badri Padhukasahasram, San Jose, CA (US); Dimitri Skvortsov, Orinda, CA (US)

(73) Assignee: Illumina, Inc., San Diego, CA (US)

(*) Notice: Subject to any disclaimer, the term of this patent is extended or adjusted under 35 U.S.C. 154(b) by 4 days.

(21) Appl. No.: 17/281,565

(22) PCT Filed: Jun. 2, 2020

(86) PCT No.: PCT/US2020/035787
§ 371 (c)(1),
(2) Date: Mar. 30, 2021

(87) PCT Pub. No.: WO2020/247411
PCT Pub. Date: Dec. 10, 2020

(65) Prior Publication Data
US 2021/0366569 A1    Nov. 25, 2021

Related U.S. Application Data

(60) Provisional application No. 62/856,651, filed on Jun. 3, 2019.

(51) Int. Cl.
| | | |
|---|---|---|
| G16B 20/10 | (2019.01) | |
| G16B 30/00 | (2019.01) | |
| G16B 30/20 | (2019.01) | |
| G16B 40/20 | (2019.01) | |
| G16B 40/30 | (2019.01) | |

(52) U.S. Cl.
CPC ............ *G16B 20/10* (2019.02); *G16B 30/00* (2019.02); *G16B 30/20* (2019.02); *G16B 40/20* (2019.02); *G16B 40/30* (2019.02)

(58) Field of Classification Search
CPC .................................................. G16B 20/10
USPC ........................................................ 702/19
See application file for complete search history.

(56) References Cited

U.S. PATENT DOCUMENTS

| | | | | |
|---|---|---|---|---|
| 10,095,831 B2 * | 10/2018 | Duenwald | ............. | G16B 30/00 |
| 2015/0005176 A1 | 1/2015 | Kim et al. | | |
| 2016/0239604 A1 | 8/2016 | Chudova et al. | | |
| 2017/0220735 A1 | 8/2017 | Duenwald et al. | | |
| 2017/0316150 A1 * | 11/2017 | Deciu | ..................... | G16B 30/00 |
| 2018/0089364 A1 | 3/2018 | Muzzey et al. | | |
| 2021/0017598 A1 * | 1/2021 | Jain | ...................... | C12Q 1/6876 |

FOREIGN PATENT DOCUMENTS

| | | |
|---|---|---|
| CN | 103374518 A | 10/2013 |
| CN | 105518151 A | 4/2016 |
| CN | 106460070 A | 2/2017 |
| CN | 107250356 A | 10/2017 |
| CN | 107771221 A | 3/2018 |
| CN | 108884491 A | 11/2018 |
| WO | WO-2017093561 A1 | 6/2017 |
| WO | WO-2017136059 A1 | 8/2017 |
| WO | WO-2019025004 A1 | 2/2019 |

OTHER PUBLICATIONS

International Search Report and Written Opinion dated Sep. 11, 2020 issued in Application No. PCT/US2020/035787.

Xin Yang et al: "Technical Validation of a Next-Generation Sequencing Assay for Detecting Clinically Relevant Levels of Breast Cancer-Related Single-Nucleotide Variants and Copy Number Variants Using Simulated Cell- Free DNA", A the Journal of Molecular Diagnostics, vol. 19, No. 4, Jul. 1, 2017 (Jul. 1, 2017), pp. 525-536, XP055726751, ISSN: 1525-1578, DOI: 10.1016/j.jmoldx.2017.04.007.

Richard B. Lanman et al: "Analytical and Clinical Validation of a Digital Sequencing Panel for Quantitative, Highly Accurate Evaluation of Cell-Free Circulating Tumor DNA", PLOS ONE, vol. 10, No. 10, Oct. 1, 2015 (Oct. 1, 2015), p. e0140712, XP055403636, DOI: 10.1371/journal.pone.0140712.

CN Office Action dated May 31, 2023, in Application No. CN202080005447.1 with English translation.

International Preliminary Report on Patentability dated Dec. 16, 2021, for International Application No. PCT/US2020/035787.

CN Office Action dated Dec. 15, 2023 in CN Application No. 202080005447.1 with English translation.

* cited by examiner

*Primary Examiner* — Kaitlyn L Minchella
*Assistant Examiner* — Janna Nicole Schultzhaus
(74) *Attorney, Agent, or Firm* — Weaver Austin Villeneuve & Sampson LLP

(57) ABSTRACT

Provided are methods and systems for sample quality control in CNV detection using test samples comprising cell-free nucleic acid fragments originating from a mother and a fetus. The method involves determining an exclusion region defined by at least a fetal fraction limit of detection (LOD) curve. The fetal fraction LOD curve varies with coverage values and indicates minimum values of fetal fractions needed to achieve a detection criterion given different coverages.

19 Claims, 35 Drawing Sheets

Each plot shows samples with observed FFs of 0% through 8%

| Effective Read Count (M) | FF error based on ERC (%) | LOD95 (%) | Obs FF Required (%) 80% conf. | Obs FF Required (%) 75% conf. |
|---|---|---|---|---|
| 1 | 3.89 | 6.50 | 8.0 | 7.3 |
| 2 | 3.14 | 4.59 | 4.2 | 3.6 |
| 3 | 2.64 | 3.75 | 2.5 | 1.9 |
| 4 | 2.31 | 3.25 | 1.6 | 1.0 |
| 5 | 2.09 | 2.91 | 0.9 | 0.3 |
| 6 | 1.95 | 2.65 | 0.4 | -0.2 |
| 7 | 1.87 | 2.46 | -0.1 | -0.7 |
| 8 | 1.82 | 2.30 | -0.5 | -1.0 |
| 9 | 1.80 | 2.17 | -0.9 | -1.5 |
| 10 | 1.80 | 2.05 | -1.3 | -1.9 |

FIG. 13

|  | Original QC (with NES FF QC) | New QC (with LOD QC, 80% +1M) |
|---|---|---|
| 1st run passes (%) | 97.75 | 97.88 |
| 1st run failures (%) | 2.25 | 2.12 |
| Passes on re-run (%) | 81.31 (inc. those not re-run because not re-run meant not salvageable) | 81.87 (exc. those not re-run because most of these were not re-run since they passed orig QC) |
| Final passes (%) | 99.58 | 99.62 |
| Final failures (%) | 0.42 | 0.38 |

FIG. 25

|  | Original QC (with NES FF QC) | New QC (with LoD QC 50% + LM) |
|---|---|---|
| 1st run passes (%) | 97.75 | 97.88 |
| 1st run failures (%) | 2.25 | 2.12 |
| Passes on re-run (%) | 81.31 (inc. those not re-run because not re-run meant not salvageable) | 81.87 (exc. those not re-run because most of these were not re-run since they passed orig QC) |
| Final passes (%) | 99.58 | 99.62 |
| Final failures (%) | 0.42 | 0.38 |

FIG. 29

LIMIT OF DETECTION BASED QUALITY CONTROL METRIC

INCORPORATION BY REFERENCE

A PCT Request Form is filed concurrently with this specification as part of the present application. Each application that the present application claims benefit of or priority to as identified in the concurrently filed PCT Request Form is incorporated by reference herein in its entirety and for all purposes.

BACKGROUND

One of the critical endeavors in human medical research is the discovery of genetic abnormalities that produce adverse health consequences. In many cases, specific genes and/or critical diagnostic markers have been identified in portions of the genome that are present at abnormal copy numbers. For example, in prenatal diagnosis, extra or missing copies of whole chromosomes are frequently occurring genetic lesions. In cancer, deletion or multiplication of copies of whole chromosomes or chromosomal segments, and higher-level amplifications of specific regions of the genome, are common occurrences.

Most information about copy number variation (CNV) has been provided by cytogenetic resolution that has permitted recognition of structural abnormalities. Conventional procedures for genetic screening and biological dosimetry have utilized invasive procedures, e.g., amniocentesis, cordocentesis, or chorionic villus sampling (CVS), to obtain cells for the analysis of karyotypes. Recognizing the need for more rapid testing methods that do not require cell culture, fluorescence in situ hybridization (FISH), quantitative fluorescence PCR (QF-PCR) and array-Comparative Genomic Hybridization (array-CGH) have been developed as molecular-cytogenetic methods for the analysis of copy number variations.

One of the critical endeavors in human medical research is the discovery of genetic abnormalities that produce adverse health consequences. In many cases, specific genes and/or critical diagnostic markers have been identified in portions of the genome that are present at abnormal copy numbers. For example, in prenatal diagnosis, extra or missing copies of whole chromosomes are frequently occurring genetic lesions. In cancer, deletion or multiplication of copies of whole chromosomes or chromosomal segments, and higher level amplifications of specific regions of the genome, are common occurrences.

Most information about copy number variation (CNV) has been provided by cytogenetic resolution that has permitted recognition of structural abnormalities. Conventional procedures for genetic screening and biological dosimetry have utilized invasive procedures, e.g., amniocentesis, cordocentesis, or chorionic villus sampling (CVS), to obtain cells for the analysis of karyotypes. Recognizing the need for more rapid testing methods that do not require cell culture, fluorescence in situ hybridization (FISH), quantitative fluorescence PCR (QF-PCR) and array-Comparative Genomic Hybridization (array-CGH) have been developed as molecular-cytogenetic methods for the analysis of copy number variations.

The advent of technologies that allow for sequencing entire genomes in relatively short time, and the discovery of circulating cell-free DNA (cfDNA) have provided the opportunity to compare genetic material originating from one chromosome to be compared to that of another without the risks associated with invasive sampling methods, which provides a tool to diagnose various kinds of copy number variations of genetic sequences of interest.

Limitations of existing methods in noninvasive prenatal diagnostics, which include insufficient sensitivity stemming from the limited levels of cfDNA, and the sequencing bias of the technology stemming from the inherent nature of genomic information, underlie the continuing need for noninvasive methods that would provide any or all of the specificity, sensitivity, and applicability, to reliably diagnose copy number changes in a variety of clinical settings. It has been shown that the average lengths of the fetal cfDNA fragments are shorter than the maternal cfDNA fragments in the plasma of pregnant women. This difference between maternal and fetal cfDNA is exploited in the implementation herein to determine CNV and/or fetal fraction. Embodiments disclosed herein fulfill some of the above needs. Some embodiments provides methods and system to control sample quality in CNV detection, so that samples having too low a fetal fraction or read coverage are identified for further processing, such as re-sequencing. Some embodiments provide high analytical sensitivity and specificity for noninvasive prenatal diagnostics and diagnoses of a variety of diseases.

SUMMARY

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

One aspect of the disclosure relates to methods for processing test samples each including cell-free nucleic acid fragments originating from a mother and a fetus. The methods are implemented using a computer system including one or more processors and memory. In some implementations, the method includes: (a) determining a value of fetal fraction of the test sample, wherein the fetal fraction of the test sample indicates the relative amount of fetal origin cell-free nucleic acid fragments in the test sample; (b) receiving, by the computer system, sequence reads obtained by sequencing the cell-free nucleic acid fragments in the test sample; (c) aligning, by the computer system, the sequence reads of the cell-free nucleic acid fragments to a reference genome comprising a sequence of interest, thereby providing sequence tags; (d) determining, by the computer system, a coverage of the sequence tags for at least a portion of the reference genome; (e) determining that the test sample is within an exclusion region based on the coverage of sequences tags determined in (d) and the fetal fraction determined in (a), wherein the exclusion region is defined by at least a fetal fraction limit of detection (LOD) curve, wherein the fetal fraction LOD curve varies with coverage values and indicates minimum values of fetal fractions needed to achieve a detection criterion given different coverages; and (f) excluding the test sample from being used to make a call of CNV of the sequence of interest, or re-sequencing the test sample to obtain re-sequenced sequence reads for making a call of CNV of the sequence of interest.

In some implementations, the method further includes, prior to (f), determining that the test sample is negative for the CNV of the sequence of interest.

In some implementations, the method further includes: repeating (a)-(d) using the re-sequenced sequence reads; determining that the test sample is outside the exclusion region; and calling the test sample as either having the CNV of the sequence of interest or not having the CNV of the sequence of interest.

In some implementations, the fetal fraction LOD curve is obtained based on LOD of affected training samples that are affected by the CNV. In some implementations, the affected samples include in silico samples. In some implementations, the affected samples include in vitro samples. In some implementations, the affected samples are obtained by combining samples having two or more fetal fractions.

In some implementations, the detection criterion is a desired level of confidence that for an observed fetal fraction the ground truth fetal fraction is larger than a specified LOD. In some implementations, the detection criterion is X % confident that for the observed fetal fraction, the ground truth fetal fraction is larger than LOD Y %. In some implementations, X is about 50%, 55%, 60%, 65%, 70%, 75%, 80%, 85%, 90%, 95%, 99%, or 99.5%. In some implementations, Y is about 50%, 55%, 60%, 65%, 70%, 75%, 80%, 85%, 90%, 95%, or 99% confidence of detection. In some implementations, X is 50% and Y is 95%. In some implementations, the specified LOD is determined as a smallest observed fetal fraction at which Y % of affected samples can be detected. In some implementations, the detection criterion for an observed fetal fraction at an observed coverage is obtained using a distribution of ground truth fetal fractions of the observed fetal fraction at the observed coverage.

In some implementations, the exclusion region is under the fetal fraction LOD curve.

In some implementations, the exclusion region is defined by the fetal fraction LOD curve and a coverage threshold.

In some implementations, the exclusion region is under both the fetal fraction LOD curve and the coverage threshold.

In some implementations, the determining the coverage of the sequence tags for the portion of the reference genome includes: (i) dividing the reference genome into a plurality of bins; (ii) determining a number of sequence tags aligning to each bin; and (iii) determining the coverage of the sequence tags using the numbers of sequence tags in bins in the portion of the reference genome. In some implementations, the method further includes adjusting, before (iii), the number of sequence tags aligning to the bin by accounting for bin-to-bin variations due to factors other than copy number variation.

In some implementations, the value of fetal fraction of the test sample is determined based on sizes of the cell-free nucleic acid fragments. In some implementations, the value of fetal fraction of the test sample is determined by: obtaining a frequency distribution of the sizes of the cell-free nucleic acid fragments; and applying the frequency distribution to a model relating fetal fraction to frequency of fragment size to obtain the fetal fraction value.

In some implementations, the value of fetal fraction of the test sample is determined based on coverage information for bins of the reference genome. In some implementations, the value of fetal fraction is calculated by: applying coverage values of a plurality of bins of the reference genome to a model relating fetal fraction to coverage of bin to obtain the fetal fraction value. In some implementations, the plurality of bins of the reference genome have higher fractions of fetal cell-free nucleic acid fragments than other bins.

In some implementations, the value of fetal fraction of the test sample is determined based on coverage information for the bins of a sex chromosome.

Another aspect of the disclosure relates to a computer system including one or more processors and system memory. The one or more processors are configured to perform any of the methods described above.

An additional aspect of the disclosure relates a computer program product including one or more computer-readable non-transitory storage media having stored thereon computer-executable instructions that, when executed by one or more processors of a computer system, cause the computer system to implement any of the methods above.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIG. 13 tabulates the LOD, coverage, and observed fetal fraction.

FIG. 25 shows the past rates and failure rates for the first run and the second run for the prior methods and the LOD QC method.

FIG. 29 shows the past and failure rates for two runs for the existing prior method and the LODQC method.

DETAILED DESCRIPTION

Definitions

Figure 1:
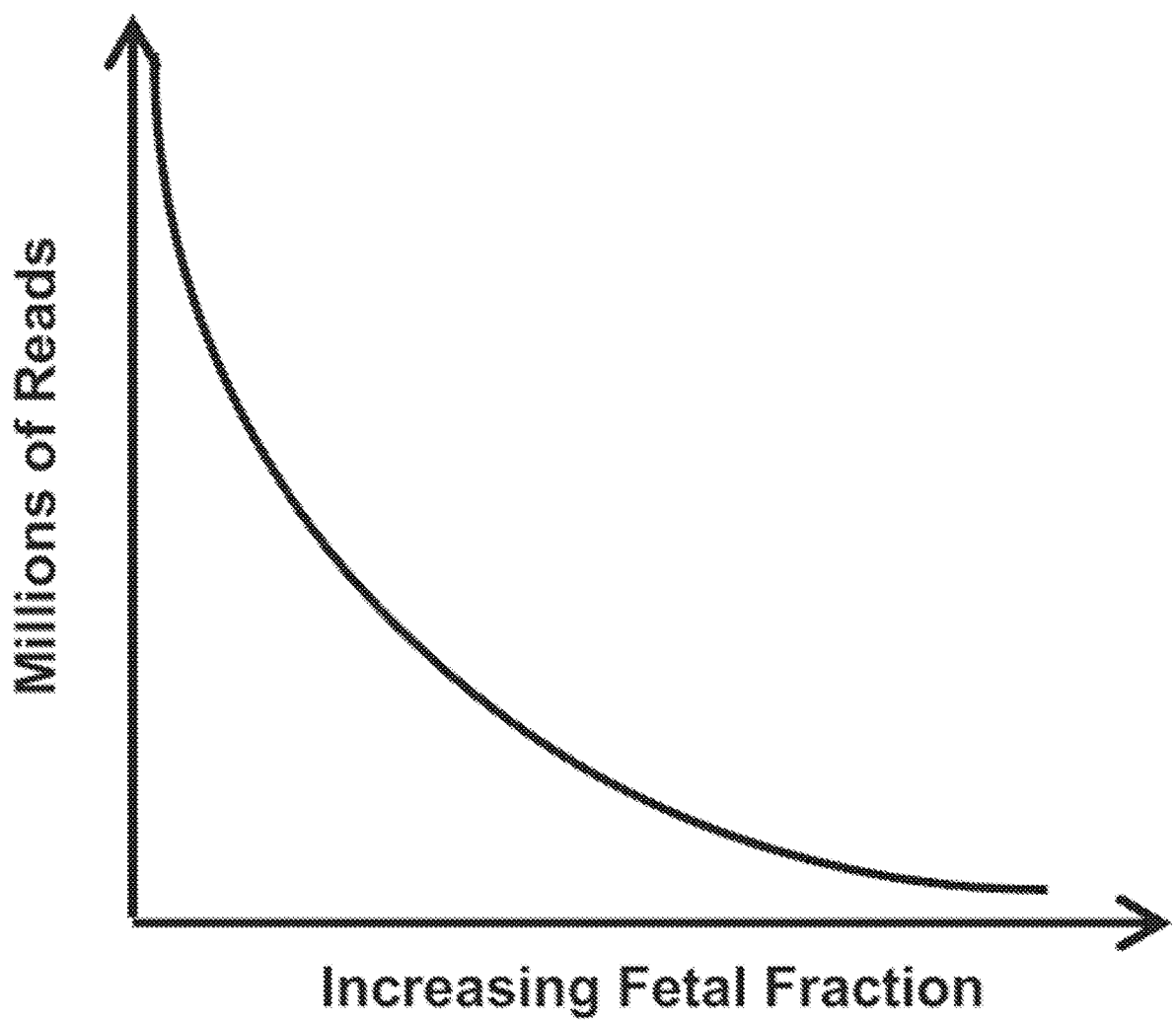
FIG. 1 schematically shows minimal fetal fraction needed to ensure detection as a function of coverage.

As used herein the term "about" with reference to numerical values refers to ±10%.

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Unless otherwise indicated, the practice of the method and system disclosed herein involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art. As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

A limit of detection (LOD) is a minimal level of signal (e.g., analytes, fetal fraction, scores indicating conditions, etc.) that can be detected with a defined confidence. In this application, an LOD is the minimal level of fetal fraction (or other analytes) required to detect an aneuploidy/CNV with a defined confidence.

The term "parameter" is used herein represents a physical feature whose value or other characteristic has an impact a relevant condition such as copy number variation. In some cases, the term parameter is used with reference to a variable that affects the output of a mathematical relation or model, which variable may be an independent variable (i.e., an input to the model) or an intermediate variable based on one or more independent variables. Depending on the scope of a model, an output of one model may become an input of another model, thereby becoming a parameter to the other model.

The term "fragment size parameter" refers to a parameter that relates to the size or length of a fragment or a collection of fragments such nucleic acid fragments; e.g., a cfDNA fragments obtained from a bodily fluid. As used herein, a parameter is "biased toward a fragment size or size range" when: 1) the parameter is favorably weighted for the fragment size or size range, e.g., a count weighted more heavily when associated with fragments of the size or size range than for other sizes or ranges; or 2) the parameter is obtained from a value that is favorably weighted for the fragment size or size range, e.g., a ratio obtained from a count weighted more heavily when associated with fragments of the size or size range. A fragment size or size range may be a characteristic of a genome or a portion thereof when the genome produces nucleic acid fragments enriched in or having a higher concentration of the size or size range relative to nucleic acid fragments from another genome or another portion of the same genome.

The term "weighting" refers to modifying a quantity such as a parameter or variable using one or more values or functions, which are considered the "weight." In certain embodiments, the parameter or variable is multiplied by the weight. In other embodiments, the parameter or variable is modified exponentially. In some embodiments, the function may be a linear or non-linear function. Examples of applicable non-linear functions include, but are not limited to Heaviside step functions, box-car functions, stair-case functions, or sigmoidal functions. Weighting an original parameter or variable may systematically increase or decrease the value of the weighted variable. In various embodiments, weighting may result in positive, non-negative, or negative values.

The term "copy number variation" herein refers to variation in the number of copies of a nucleic acid sequence present in a test sample in comparison with the copy number of the nucleic acid sequence present in a reference sample. In certain embodiments, the nucleic acid sequence is 1 kb or larger. In some cases, the nucleic acid sequence is a whole chromosome or significant portion thereof. A "copy number variant" refers to the sequence of nucleic acid in which copy-number differences are found by comparison of a nucleic acid sequence of interest in test sample with an expected level of the nucleic acid sequence of interest. For example, the level of the nucleic acid sequence of interest in the test sample is compared to that present in a qualified sample. Copy number variants/variations include deletions, including microdeletions, insertions, including microinsertions, duplications, multiplications, and translocations. CNVs encompass chromosomal aneuploidies and partial aneuploidies.

The term "aneuploidy" herein refers to an imbalance of genetic material caused by a loss or gain of a whole chromosome, or part of a chromosome.

The terms "chromosomal aneuploidy" and "complete chromosomal aneuploidy" herein refer to an imbalance of genetic material caused by a loss or gain of a whole chromosome, and includes germline aneuploidy and mosaic aneuploidy.

The terms "partial aneuploidy" and "partial chromosomal aneuploidy" herein refer to an imbalance of genetic material caused by a loss or gain of part of a chromosome, e.g., partial monosomy and partial trisomy, and encompasses imbalances resulting from translocations, deletions and insertions.

The term "plurality" refers to more than one element. For example, the term is used herein in reference to a number of nucleic acid molecules or sequence tags that are sufficient to identify significant differences in copy number variations in test samples and qualified samples using the methods disclosed herein. In some embodiments, at least about $3 \times 10^6$ sequence tags of between about 20 and 40 bp are obtained for each test sample. In some embodiments, each test sample provides data for at least about $5 \times 10^6$, $8 \times 10^6$, $10 \times 10^6$, $15 \times 10^6$, $20 \times 10^6$, $30 \times 10^6$, $40 \times 10^6$, or $50 \times 10^6$ sequence tags, each sequence tag comprising between about 20 and 40 bp.

The term "paired end reads" refers to reads from paired end sequencing that obtains one read from each end of a nucleic acid fragment. Paired end sequencing may involve fragmenting strands of polynucleotides into short sequences called inserts. Fragmentation is optional or unnecessary for relatively short polynucleotides such as cell free DNA molecules.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA molecules. The term "polynucleotide" includes, without limitation, single- and double-stranded polynucleotide.

The term "test sample" herein refers to a sample, typically derived from a biological fluid, cell, tissue, organ, or organism, comprising a nucleic acid or a mixture of nucleic acids comprising at least one nucleic acid sequence that is to be screened for copy number variation. In certain embodiments the sample comprises at least one nucleic acid sequence whose copy number is suspected of having undergone variation. Such samples include, but are not limited to sputum/oral fluid, amniotic fluid, blood, a blood fraction, or fine needle biopsy samples (e.g., surgical biopsy, fine needle biopsy, etc.), urine, peritoneal fluid, pleural fluid, and the like. Although the sample is often taken from a human subject (e.g., patient), the assays can be used to copy number variations (CNVs) in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "qualified sample" or "unaffected sample" herein refers to a sample comprising a mixture of nucleic acids that are present in a known copy number to which the nucleic acids in a test sample are to be compared, and it is a sample that is normal, i.e., not aneuploid, for the nucleic acid sequence of interest. In some embodiments, qualified samples are used as unaffected training samples of a training set to derive sequence masks or sequence profiles. In certain embodiments, qualified samples are used for identifying one or more normalizing chromosomes or segments for a chromosome under consideration. For example, qualified samples may be used for identifying a normalizing chromosome for chromosome 21. In such case, the qualified sample is a sample that is not a trisomy 21 sample. Another example involves using only females as qualifying samples for chromosome X. Qualified samples may also be employed for other purposes such as determining thresholds for calling affected samples, identifying thresholds for defining mask regions on a reference sequence, determining expected coverage quantities for different regions of a genome, and the like.

The term "training set" herein refers to a set of training samples that can comprise affected and/or unaffected samples and are used to develop a model for analyzing test samples. In some embodiments, the training set includes unaffected samples. In these embodiments, thresholds for determining CNV are established using training sets of samples that are unaffected for the copy number variation of interest. The unaffected samples in a training set may be used as the qualified samples to identify normalizing sequences, e.g., normalizing chromosomes, and the chromosome doses of unaffected samples are used to set the thresholds for each of the sequences, e.g., chromosomes, of interest. In some embodiments, the training set includes affected samples. The affected samples in a training set can be used to verify that affected test samples can be easily differentiated from unaffected samples.

A training set is also a statistical sample in a population of interest, which statistical sample is not to be confused with a biological sample. A statistical sample often comprises multiple individuals, data of which individuals are used to determine one or more quantitative values of interest generalizable to the population. The statistical sample is a subset of individuals in the population of interest. The individuals may be persons, animals, tissues, cells, other biological samples (i.e., a statistical sample may include multiple biological samples), and other individual entities providing data points for statistical analysis.

Usually, a training set is used in conjunction with a validation set. The term "validation set" is used to refer to a set of individuals in a statistical sample, data of which individuals are used to validate or evaluate the quantitative values of interest determined using a training set. In some embodiments, for instance, a training set provides data for calculating a mask for a reference sequence, while a validation set provides data to evaluate the validity or effectiveness of the mask.

"Evaluation of copy number" is used herein in reference to the statistical evaluation of the status of a genetic sequence related to the copy number of the sequence. For example, in some embodiments, the evaluation comprises the determination of the presence or absence of a genetic sequence. In some embodiments the evaluation comprises the determination of the partial or complete aneuploidy of a genetic sequence. In other embodiments the evaluation comprises discrimination between two or more samples based on the copy number of a genetic sequence. In some embodiments, the evaluation comprises statistical analyses, e.g., normalization and comparison, based on the copy number of the genetic sequence.

The term "qualified nucleic acid" is used interchangeably with "qualified sequence," which is a sequence against which the amount of a sequence or nucleic acid of interest is compared. A qualified sequence is one present in a biological sample preferably at a known representation, i.e., the amount of a qualified sequence is known. Generally, a qualified sequence is the sequence present in a "qualified sample." A "qualified sequence of interest" is a qualified sequence for which the amount is known in a qualified sample, and is a sequence that is associated with a difference of a sequence of interest between a control subject and an individual with a medical condition.

The term "sequence of interest" or "nucleic acid sequence of interest" herein refers to a nucleic acid sequence that is associated with a difference in sequence representation between healthy and diseased individuals. A sequence of interest can be a sequence on a chromosome that is misrepresented, i.e., over- or under-represented, in a disease or genetic condition. A sequence of interest may be a portion of a chromosome, i.e., chromosome segment, or a whole chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "normalizing sequence" herein refers to a sequence that is used to normalize the number of sequence tags mapped to a sequence of interest associated with the normalizing sequence. In some embodiments, a normalizing sequence comprises a robust chromosome. A "robust chromosome" is one that is unlikely to be aneuploid. In some cases involving the human chromosome, a robust chromosome is any chromosome other than the X chromosome, Y chromosome, chromosome 13, chromosome 18, and chromosome 21. In some embodiments, the normalizing sequence displays a variability in the number of sequence tags that are mapped to it among samples and sequencing runs that approximates the variability of the sequence of interest for which it is used as a normalizing parameter. The normalizing sequence can differentiate an affected sample from one or more unaffected samples. In some implementations, the normalizing sequence best or effectively differentiates, when compared to other potential normalizing sequences such as other chromosomes, an affected sample from one or more unaffected samples. In some embodiments, the variability of the normalizing sequence is calculated as the variability in the chromosome dose for the sequence of interest across samples and sequencing runs. In some embodiments, normalizing sequences are identified in a set of unaffected samples.

A "normalizing chromosome," "normalizing denominator chromosome," or "normalizing chromosome sequence" is an example of a "normalizing sequence." A "normalizing chromosome sequence" can be composed of a single chromosome or of a group of chromosomes. In some embodiments, a normalizing sequence comprises two or more robust chromosomes. In certain embodiments, the robust chromosomes are all autosomal chromosomes other than chromosomes, X, Y, 13, 18, and 21. A "normalizing segment" is another example of a "normalizing sequence." A "normalizing segment sequence" can be composed of a single segment of a chromosome or it can be composed of two or more segments of the same or of different chromosomes. In certain embodiments, a normalizing sequence is intended to normalize for variability such as process-related, interchromosomal (intra-run), and inter-sequencing (inter-run) variability.

The term "differentiability" herein refers to a characteristic of a normalizing chromosome that enables one to distinguish one or more unaffected, i.e., normal, samples from one or more affected, i.e., aneuploid, samples. A normalizing chromosome displaying the greatest "differentiability" is a chromosome or group of chromosomes that provides the greatest statistical difference between the distribution of chromosome doses for a chromosome of interest in a set of qualified samples and the chromosome dose for the same chromosome of interest in the corresponding chromosome in the one or more affected samples.

The term "variability" herein refers to another characteristic of a normalizing chromosome that enables one to distinguish one or more unaffected, i.e., normal, samples from one or more affected, i.e., aneuploid, samples. The variability of a normalizing chromosome, which is measured in a set of qualified samples, refers to the variability in the number of sequence tags that are mapped to it that approximates the variability in the number of sequence tags that are mapped to a chromosome of interest for which it serves as a normalizing parameter.

The term "sequence tag density" herein refers to the number of sequence reads that are mapped to a reference genome sequence, e.g., the sequence tag density for chromosome 21 is the number of sequence reads generated by the sequencing method that are mapped to chromosome 21 of the reference genome.

The term "sequence tag density ratio" herein refers to the ratio of the number of sequence tags that are mapped to a chromosome of the reference genome, e.g., chromosome 21, to the length of the reference genome chromosome.

The term "sequence dose" herein refers to a parameter that relates the number of sequence tags or another parameter identified for a sequence of interest and the number of sequence tags or the other parameter identified for the normalizing sequence. In some cases, the sequence dose is the ratio of the sequence tag coverage or the other parameter for a sequence of interest to the sequence tag coverage or the other parameter for a normalizing sequence. In some cases, the sequence dose refers to a parameter that relates the sequence tag density of a sequence of interest to the sequence tag density of a normalizing sequence. A "test sequence dose" is a parameter that relates the sequence tag density or the other parameter of a sequence of interest, e.g., chromosome 21, to that of a normalizing sequence, e.g., chromosome 9, determined in a test sample. Similarly, a "qualified sequence dose" is a parameter that relates the sequence tag density or the other parameter of a sequence of interest to that of a normalizing sequence determined in a qualified sample.

The term "coverage" refers to the abundance of sequence tags mapped to a defined sequence. Coverage can be quantitatively indicated by sequence tag density (or count of sequence tags), sequence tag density ratio, normalized coverage amount, adjusted coverage values, etc.

The term "coverage quantity" refers to a modification of raw coverage and often represents the relative quantity of sequence tags (sometimes called counts) in a region of a genome such as a bin. A coverage quantity may be obtained by normalizing, adjusting and/or correcting the raw coverage or count for a region of the genome. For example, a normalized coverage quantity for a region may be obtained by dividing the sequence tag count mapped to the region by the total number sequence tags mapped to the entire genome. Normalized coverage quantity allows comparison of coverage of a bin across different samples, which may have different depths of sequencing. It differs from sequence dose in that the latter is typically obtained by dividing by the tag count mapped to a subset of the entire genome. The subset is one or more normalizing segments or chromosomes. Coverage quantities, whether or not normalized, may be corrected for global profile variation from region to region on the genome, G-C fraction variations, outliers in robust chromosomes, etc.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "parameter" herein refers to a numerical value that characterizes a property of a system. Frequently, a parameter numerically characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a qualified threshold value is calculated using a qualifying data set and serves as a limit of diagnosis of a copy number variation, e.g., an aneuploidy, in an organism. If a threshold is exceeded by results obtained from methods disclosed herein, a subject can be diagnosed with a copy number variation, e.g., trisomy 21. Appropriate threshold values for the methods described herein can be identified by analyzing normalized values (e.g. chromosome doses, NCVs or NSVs) calculated for a training set of samples. Threshold values can be identified using qualified (i.e., unaffected) samples in a training set which comprises both qualified (i.e., unaffected) samples and affected samples. The samples in the training set known to have chromosomal aneuploidies (i.e., the affected samples) can be used to confirm that the chosen thresholds are useful in differentiating affected from unaffected samples in a test set (see the Examples herein). The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may be advantageous to use larger sets of qualified samples to improve the diagnostic utility of the threshold values.

The term "bin" refers to a segment of a sequence or a segment of a genome. In some embodiments, bins are contiguous with one another within the genome or chromosome. Each bin may define a sequence of nucleotides in a reference genome. Sizes of the bin may be 1 kb, 100 kb, 1 Mb, etc., depending on the analysis required by particular applications and sequence tag density. In addition to their positions within a reference sequence, bins may have other characteristics such as sample coverage and sequence structure characteristics such as G-C fraction.

The term "masking threshold" is used herein to refer to a quantity against which a value based on the number of sequence tags in a sequence bin is compared, wherein a bin having a value exceeding the masking threshold is masked. In some embodiments, the masking threshold can be a percentile rank, an absolute count, a mapping quality score, or other suitable values. In some embodiments, a masking threshold may be defined as the percentile rank of a coefficient of variation across multiple unaffected samples. In other embodiments, a masking threshold may be defined as a mapping quality score, e.g., a MapQ score, which relates to the reliability of aligning sequence reads to a reference genome. Note that a masking threshold value is different from a copy number variation (CNV) threshold value, the latter being a cutoff to characterize a sample containing a nucleic acid from an organism suspected of having a medical condition related to CNV. In some embodiment, a CNV threshold value is defined relative to a normalized chromosome value (NCV) or a normalized segment value (NSV) described elsewhere herein.

The term "normalized value" herein refers to a numerical value that relates the number of sequence tags identified for the sequence (e.g. chromosome or chromosome segment) of interest to the number of sequence tags identified for a normalizing sequence (e.g. normalizing chromosome or normalizing chromosome segment). For example, a "normalized value" can be a chromosome dose as described elsewhere herein, or it can be an NCV, or it can be an NSV as described elsewhere herein.

The term "read" refers to a sequence obtained from a portion of a nucleic acid sample. Typically, though not necessarily, a read represents a short sequence of contiguous base pairs in the sample. The read may be represented symbolically by the base pair sequence (in A, T, C, or G) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "genomic read" is used in reference to a read of any segments in the entire genome of an individual.

The term "sequence tag" is herein used interchangeably with the term "mapped sequence tag" to refer to a sequence read that has been specifically assigned, i.e., mapped, to a larger sequence, e.g., a reference genome, by alignment. Mapped sequence tags are uniquely mapped to a reference genome, i.e., they are assigned to a single location to the reference genome. Unless otherwise specified, tags that map to the same sequence on a reference sequence are counted once. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to allow a limited amount of mismatch in aligning to a reference genome. In some embodiments, tags that can be mapped to more than one location on a reference genome, i.e., tags that do not map uniquely, may not be included in the analysis.

The term "non-redundant sequence tag" refers to sequence tags that do not map to the same site, which is counted for the purpose of determining normalized chromosome values (NCVs) in some embodiments. Sometimes multiple sequence reads are aligned to the same locations on a reference genome, yielding redundant or duplicated sequence tags. In some embodiments, duplicate sequence tags that map to the same position are omitted or counted as one "non-redundant sequence tag" for the purpose of determining NCVs. In some embodiments, non-redundant sequence tags aligned to non-excluded sites are counted to yield "non-excluded-site counts" (NES counts) for determining NCVs.

The term "site" refers to a unique position (i.e. chromosome ID, chromosome position and orientation) on a reference genome. In some embodiments, a site may provide a position for a residue, a sequence tag, or a segment on a sequence.

"Excluded sites" are sites found in regions of a reference genome that have been excluded for the purpose of counting sequence tags. In some embodiments, excluded sites are found in regions of chromosomes that contain repetitive sequences, e.g., centromeres and telomeres, and regions of chromosomes that are common to more than one chromosome, e.g., regions present on the Y-chromosome that are also present on the X chromosome.

"Non-excluded sites" (NESs) are sites that are not excluded in a reference genome for the purpose of counting sequence tags.

"Non-excluded-site counts" (NES counts) are the numbers of sequence tags that are mapped to NESs on a reference genome. In some embodiments, NES counts are the numbers of non-redundant sequence tags mapped to NESs. In some embodiments, coverage and related parameters such normalized coverage quantities, global profile removed coverage quantities, and chromosome dose are based on NES counts. In one example, a chromosome dose is calculated as the ratio of the NES count for a chromosome of interest to the count for a normalizing chromosome.

Normalized chromosome value (NCV) relates coverage of a test sample to coverages of a set of training/qualified samples. In some embodiments, NCV is based on chromosome dose. In some embodiments, NCV relates to the difference between the chromosome dose of a chromosome of interest in a test sample and the mean of the corresponding chromosome dose in a set of qualified samples as, and can be calculated as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome ratio (dose) for test sample i.

In some embodiments, NCV can be calculated "on the fly" by relating the chromosome dose of a chromosome of interest in a test sample to the median of the corresponding chromosome dose in multiplexed samples sequenced on the same flow cells as:

$$NCV_{ij} = \frac{x_{ij} - M_j}{\hat{\sigma}_j}$$

where $M_j$ is the estimated median for the j-th chromosome dose in a set of multiplexed samples sequenced on the same flow cell; $\hat{\sigma}_j$ is the standard deviation for the j-th chromosome dose in one or more sets of multiplexed samples sequenced on one or more flow cells, and $x_{ij}$ is the observed j-th chromosome dose for test sample i. In this embodiment, test sample i is one of the multiplexed samples sequenced on the same flow cell from which $M_j$ is determined.

For example, for chromosome of interest 21 in test sample A, which is sequenced as one of 64 multiplexed samples on one flow cell, the NCV for chromosome 21 in test sample A is calculated as the dose of chromosome 21 in sample *A minus* the median of the dose for chromosome 21 determined in the 64 multiplexed samples, divided by the standard deviation of the dose for chromosome 21 determined for the 64 multiplexed samples on flow cell 1, or of additional flow cells.

As used herein, the terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

The term "mapping" used herein refers to specifically assigning a sequence read to a larger sequence, e.g., a reference genome, by alignment.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In various embodiments, the reference sequence is a consensus sequence or other combination derived from multiple individuals. However, in certain applications, the reference sequence may be taken from a particular individual.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "based on" when used in the context of obtaining a specific quantitative value, herein refers to using another quantity as input to calculate the specific quantitative value as an output.

The term "patient sample" herein refers to a biological sample obtained from a patient, i.e., a recipient of medical attention, care or treatment. The patient sample can be any of the samples described herein. In certain embodiments, the patient sample is obtained by non-invasive procedures, e.g., peripheral blood sample or a stool sample. The methods described herein need not be limited to humans Thus, various veterinary applications are contemplated in which case the patient sample may be a sample from a non-human mammal (e.g., a feline, a porcine, an equine, a bovine, and the like).

The term "mixed sample" herein refers to a sample containing a mixture of nucleic acids, which are derived from different genomes.

The term "maternal sample" herein refers to a biological sample obtained from a pregnant subject, e.g., a woman.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

As used herein, the term "corresponding to" sometimes refers to a nucleic acid sequence, e.g., a gene or a chromosome, that is present in the genome of different subjects, and which does not necessarily have the same sequence in all genomes, but serves to provide the identity rather than the genetic information of a sequence of interest, e.g., a gene or chromosome.

As used herein, the term "fetal fraction" refers to the fraction of fetal nucleic acids present in a sample comprising fetal and maternal nucleic acid. Fetal fraction is often used to characterize the cfDNA in a mother's blood.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

As used herein, the term "polynucleotide length" refers to the absolute number of nucleotides in a sequence or in a region of a reference genome. The term "chromosome length" refers to the known length of the chromosome given in base pairs, e.g., provided in the NCBI36/hg18 assembly of the human chromosome found at |genome|.|ucsc|.|edu/cgi-bin/hgTracks?hgsid=167155613&chromInfoPage=on the World Wide Web.

The term "subject" herein refers to a human subject as well as a non-human subject such as a mammal, an invertebrate, a vertebrate, a fungus, a yeast, a bacterium, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "condition" herein refers to "medical condition" as a broad term that includes all diseases and disorders, but can include injuries and normal health situations, such as pregnancy, that might affect a person's health, benefit from medical assistance, or have implications for medical treatments.

The term "complete" when used in reference to a chromosomal aneuploidy herein refers to a gain or loss of an entire chromosome.

The term "partial" when used in reference to a chromosomal aneuploidy herein refers to a gain or loss of a portion, i.e., segment, of a chromosome.

The term "mosaic" herein refers to denote the presence of two populations of cells with different karyotypes in one individual who has developed from a single fertilized egg. Mosaicism may result from a mutation during development which is propagated to only a subset of the adult cells.

The term "non-mosaic" herein refers to an organism, e.g., a human fetus, composed of cells of one karyotype.

The term "sensitivity" as used herein refers to the probability that a test result will be positive when the condition of interest is present. It may be calculated as the number of true positives divided by the sum of true positives and false negatives.

The term "specificity" as used herein refers to the probability that a test result will be negative when the condition of interest is absent. It may be calculated as the number of true negatives divided by the sum of true negatives and false positives.

The term "enrich" herein refers to the process of amplifying polymorphic target nucleic acids contained in a portion of a maternal sample, and combining the amplified product with the remainder of the maternal sample from which the portion was removed. For example, the remainder of the maternal sample can be the original maternal sample.

The term "original maternal sample" herein refers to a non-enriched biological sample obtained from a pregnant subject, e.g., a woman, who serves as the source from which a portion is removed to amplify polymorphic target nucleic acids. The "original sample" can be any sample obtained from a pregnant subject, and the processed fractions thereof, e.g., a purified cfDNA sample extracted from a maternal plasma sample.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, and a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

Introduction and Context

CNV in the human genome significantly influence human diversity and predisposition to diseases (Redon et al., Nature 23:444-454 [2006], Shaikh et al. Genome Res 19:1682-1690 [2009]). Such diseases include, but are not limited to cancer, infectious and autoimmune diseases, diseases of the nervous system, metabolic and/or cardiovascular diseases, and the like.

CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as Autism, ADHD, and schizophrenia as compared to normal controls, highlighting the potential pathogenicity of rare or unique CNVs (Sebat et al., 316:445-449 [2007]; Walsh et al., Science 320:539-543 [2008]). CNV arise from genomic rearrangements, primarily owing to deletion, duplication, insertion, and unbalanced translocation events.

It has been shown that cfDNA fragments of fetal origin are shorter, on average, than those of maternal origin. NIPT (Non-invasive prenatal testing) based on NGS data has been successfully implemented. Current methodologies involve sequencing maternal samples using short reads (25 bp-36 bp), aligning to the genome, computing and normalizing sub-chromosomal coverage, and finally evaluating over-representation of target chromosomes (13/18/21/X/Y) compared to the expected normalized coverage associated with a normal diploid genome. Thus, traditional NIPT assay and analysis relies on the counts or coverage to evaluate the likelihood of fetal aneuploidy.

Since maternal plasma samples represent a mixture of maternal and fetal cfDNA, the success of any given NIPT method depends on its sensitivity to detect copy number changes in the low fetal fraction samples. For counting based methods, their sensitivity is determined by (a) sequencing depth and (b) ability of data normalization to reduce technical variance. This disclosure provides analytical methodology for NIPT and other applications by deriving fragment size information from, e.g., paired-end reads, and using this information in an analysis pipeline. Improved analytical sensitivity provides the ability to apply NIPT methods at reduced coverage (e.g., reduced sequencing depth) which enables the use of the technology for lower-cost testing of average risk pregnancies.

In some embodiments, methods are provided for determining copy number variation (CNV) of fetuses using maternal samples containing maternal and fetal cell free DNA.

Aspects of this disclosure pertain to methods and systems that can identify sample measurements for which calls of copy number variation can be reliably made and sample measurements for which such calls cannot be reliably made. In other words, the disclosed embodiments are able to discriminate between sample measurements that have sufficient information to make trustworthy calls and sample measurements that do not have sufficient information.

In some current approaches for discriminating between reliable and unreliable sample measurements, fetal fraction is used as a metric for determining whether or not to exclude a sample from being called. Such approaches may employ running a sequencing routine in a particular manner for NIPT samples. The resulting sample has a coverage or number of reads value for non-excluded regions of the genome or chromosome. Such approaches may also determine a value of fetal fraction. If the determined value of fetal fraction is below some threshold, say 3%, the sample measurement is excluded. At the bottom of such plots, there is sample exclusion region that covers sample measurements having rather low effective read counts and/or have low determined fetal fraction values. In some implementations, the excluded region includes a step where for particularly low fetal fractions even relatively high numbers of effective reads are excluded.

Data, as shown in certain figures hereinafter, illustrates various examples of situations where determined values of fetal fraction are inaccurate possibly for a variety of reasons. The data shows certain trends in fetal fraction error such as increasing fetal fraction error with increasing call error (which may result from reduced coverage) and increasing fetal fraction error with decreasing magnitude of the true fetal fraction value. Due to these problems with fetal fraction as a mode for determining which samples to exclude, another technique for determining which's samples to exclude should be used.

Fetal fraction affects the determination of fetal cell-free DNA abundance and copy number variations in NIPT. When fetal fraction decreases in a sample, it becomes more difficult to accurately determine the relative coverage of fetal cell-free DNA because the signal decreases and the relative noise increases as fetal fraction decreases. Coverage or sequencing depth also has a similar effect on CNV detection. Because the two factors jointly affect CNV detection, the minimal fetal fraction needed to ensure detection changes as a function of coverage, having a hyperbolic shape as shown in FIG. 1.

Figure 2:
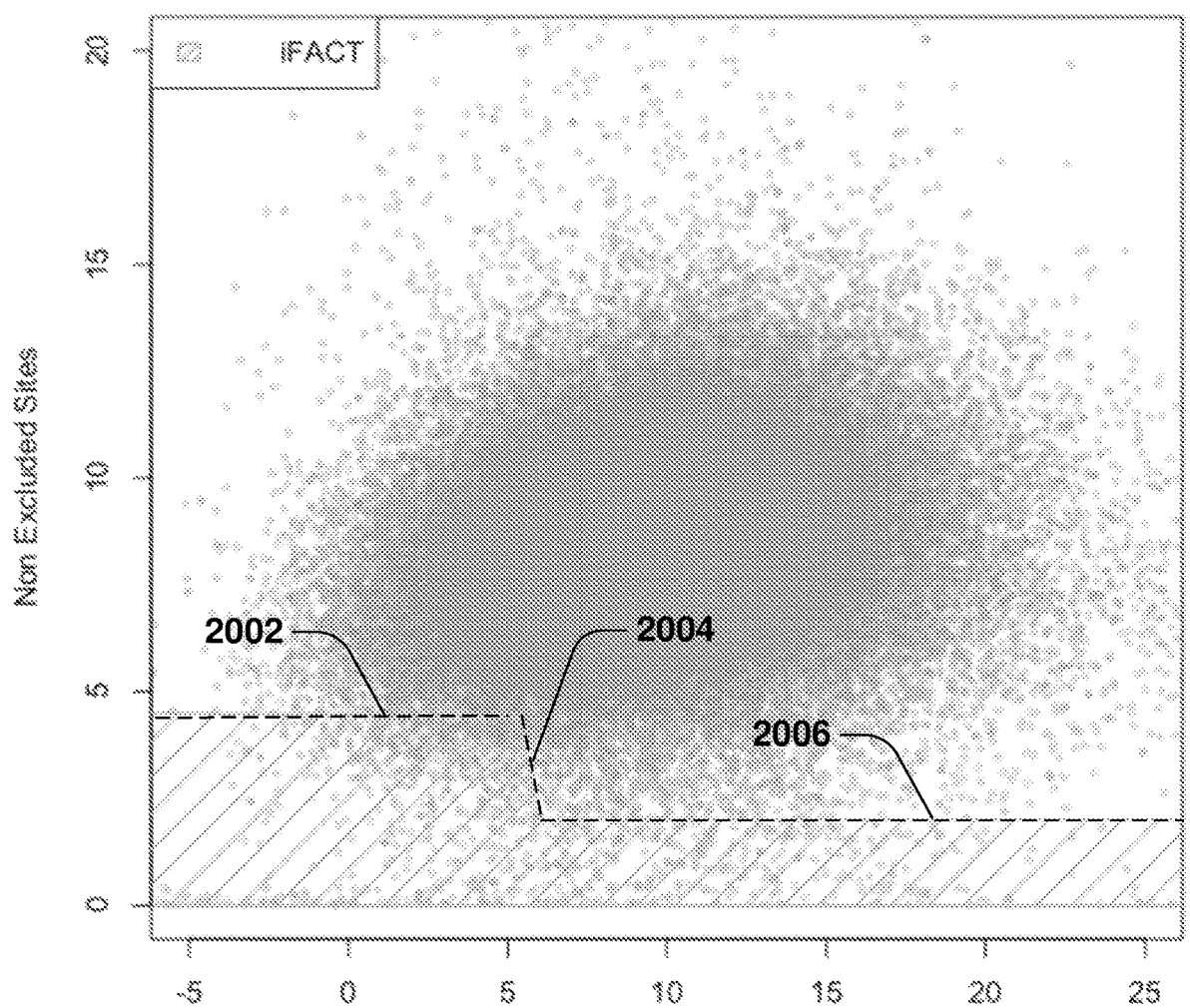
FIG. 2 shows a two-step coverage threshold for excluding samples.

Existing methods perform quality control by excluding samples that have low coverage. For example, some existing methods set two levels of coverage threshold depending on fetal fraction values. In the example shown in FIG. 2, a first coverage thresholds is set at about 4.5 M non-excluded site NES or effective reads for fetal fraction smaller than about 5% (line 2002), and a second coverage threshold of about 2 M (line 2006) for fetal fraction larger than about 5%. A line or curve (2004) connects the two threshold levels.

Figure 3:
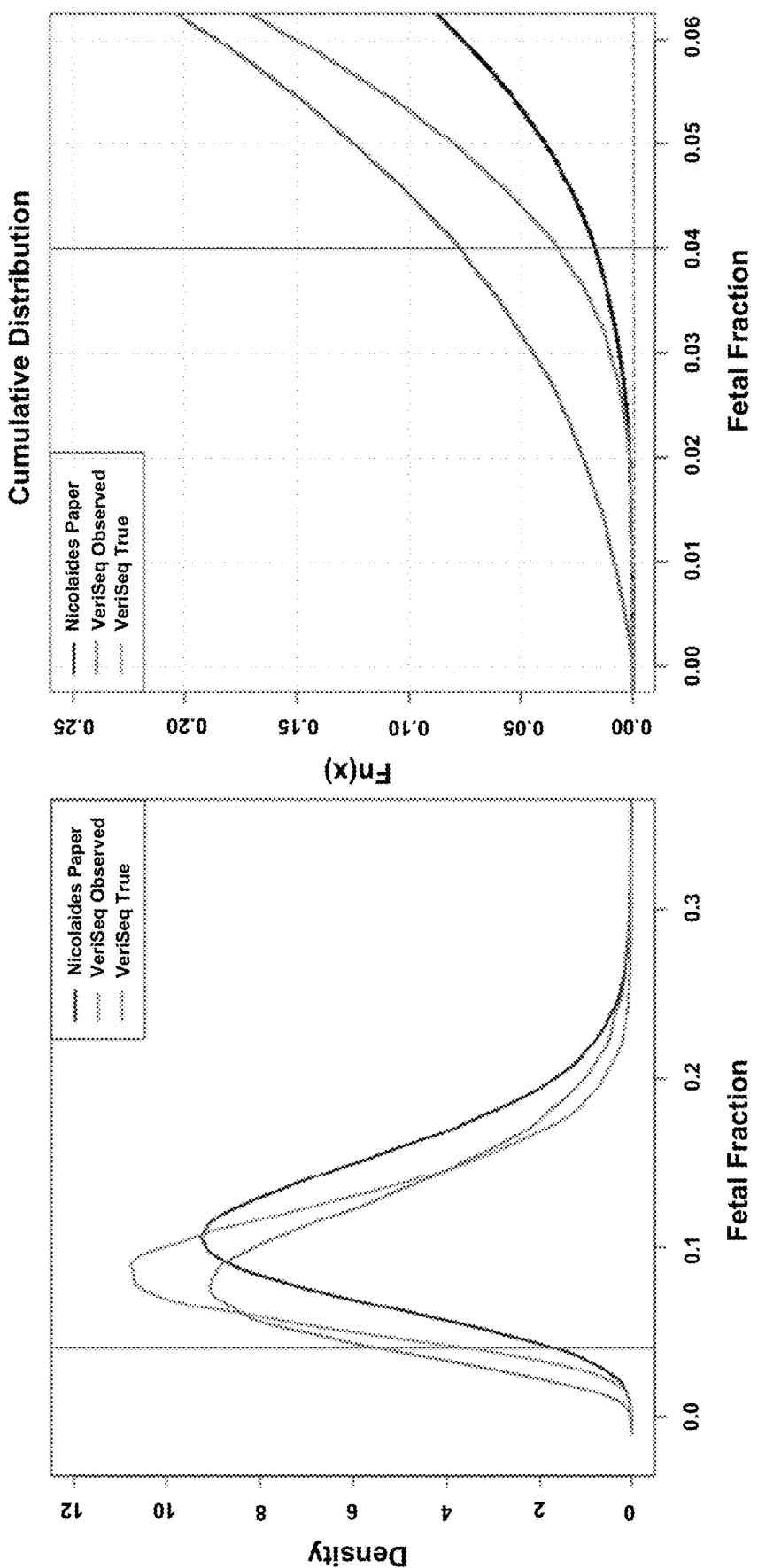
FIG. 3 shows fetal fraction distributions for three populations or samples thereof.

However, such methods have various limitations. They do not adequately capture the relation between coverage and fetal fraction with regard to their effect on CNV detection. Moreover, the thresholds used in these existing methods are static, the same thresholds being applied to different samples, populations and platforms. As shown in FIG. 3, different sample populations have different fetal fraction distributions. FIG. 3 shows fetal fraction distributions for three populations or samples thereof. The left panel shows the probability density function of the three populations. The panel on the right shows the cumulative distributions of the three populations. The cumulative distributions clearly show that the fixed fetal fraction threshold of 0.04 excludes different portions of samples from the three populations.

This disclosure provides methods and systems of quality control (QC) in CNV detection processes such as those shown in FIGS. 4A, 4B, 15, and 16A. The QC can be performed either before or after making a CNV call to identify samples that have fetal fraction levels too low to yield reliable results. The identified samples can be rerun to obtain new reads. If sequencing depth increases in rerun, coverage increases, which improve signal or reduce noise of the sample. The disclosed implementations when applied to different sample populations can take into consideration variations between samples and populations. And they can more effectively identify samples with low fetal fraction and/or low read coverage.

Example Workflows

Figure 4A:
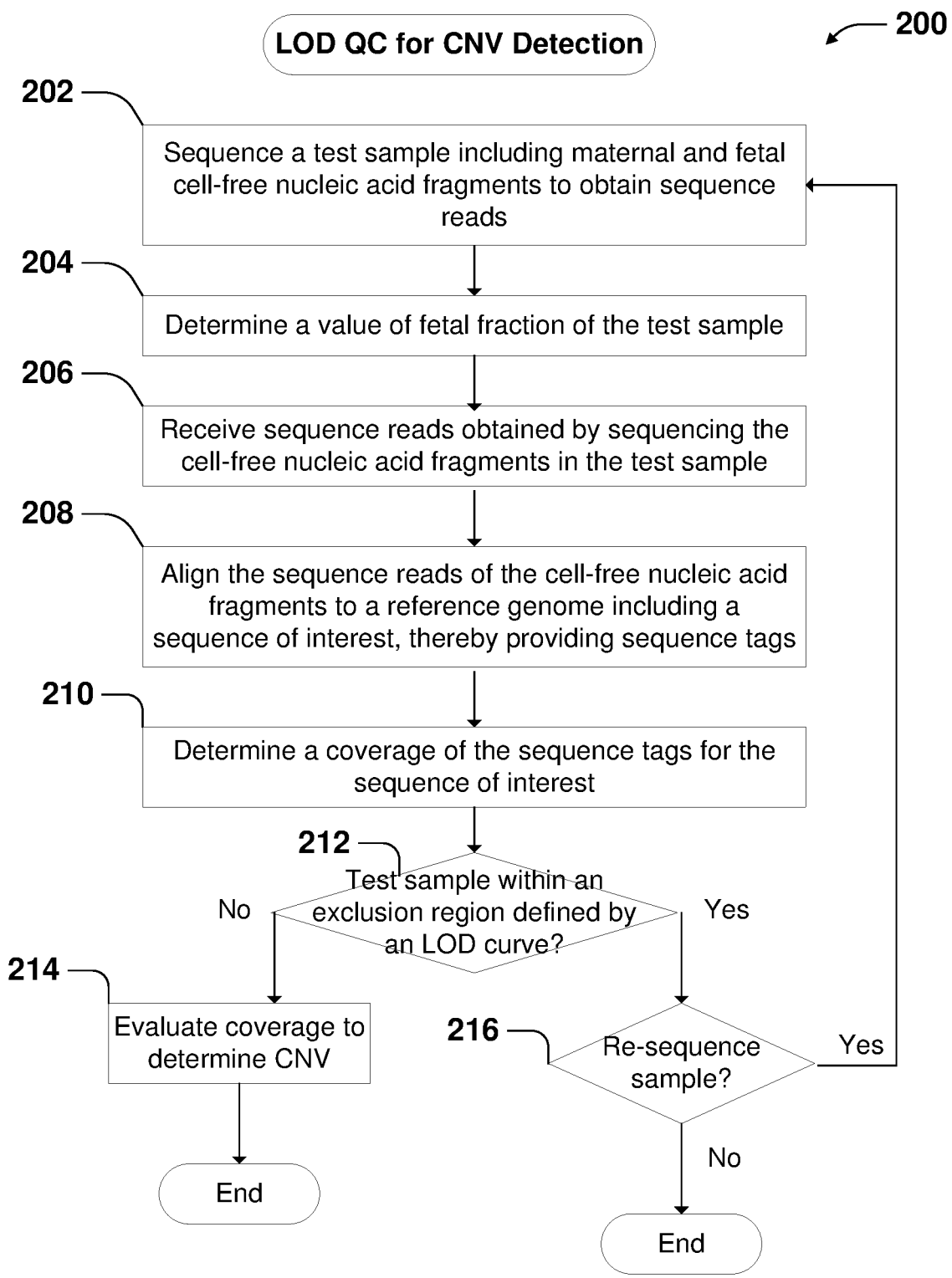
FIG. 4A shows workflow 200 that uses a limit of detection (LOD) QC method for determining CNV according to some implementations.

The workflows and labeled steps in this disclosure can be performed in orders different from those described in figures, examples, and claims, unless specified otherwise. For example, operation of determining a fetal fraction value shown in box 204 may be performed before or after the operations shown in 202, 206, 208, and 210. FIG. 4A shows workflow 200 that uses a limit of detection (LOD) QC method for determining CNV according to some implementations. In this workflow, the quality check occurs at box 212 to check whether the test sample is within an exclusion region that is defined by at least a fetal fraction LOD curve. In many implementations, the exclusion region is defined by the LOD curve and a coverage threshold or a fetal fraction threshold. This step and its downstream steps can be applied to other CNV detection process described hereinafter. This illustrative workflow involves sequencing a test sample including maternal and fetal cell-free nucleic acid fragments to obtain sequence reads. See box 202. Various techniques may be used to obtain the sequence reads, including but not limited to the sequencing techniques described herein after.

Process 200 then proceed to determine a fetal fraction value of the test sample. In some implementations, the obtained sequence reads from 202 are used to determine a fetal fraction. However, other nucleic acids from the same individuals may also be used. In some implementations, various techniques may be used to determine the fetal fraction of the test sample, including but not limited to the techniques described hereinafter. Briefly, in some implementations, the value of fetal fraction of the test sample is determined based on sizes of the cell-free nucleic acid fragments. In some implementations, by obtaining a frequency distribution of the sizes of the cell-free nucleic acid fragments, and applying the frequency distribution to a model relating fetal fraction to frequency of fragment size to obtain the fetal fraction value. In some implementations, the fetal fraction value is determined based on coverage information for the bins of the reference genome, where the reference genome is divided into segments or bins. In some implementations, the value of fetal fraction is calculated by applying coverage values of a plurality of bins of the reference genome to a model relating fetal fraction to coverage of bin to obtain the fetal fraction value. In some implementations, bins that have over-represented fetal cell-free nucleic acid fragments aligned to them are selected from training samples. The test reads aligned to the bins are used to determine the fetal fraction. In some implementations, the value of fetal fraction of the test sample is determined based on coverage information for the bins of a sex chromosome, such as the Y chromosome in a maternal sample obtained from a mother carrying a male fetus.

Process 200 further involves receiving sequence reads obtained by sequencing the cell-free nucleic acid fragments in the test sample. See box 206. It then aligns the sequence reads of the cell-free nucleic acid fragments to a reference genome including the sequence of interest, thereby providing sequence tags. See box 208.

Process 200 proceeds to determine a coverage of the sequence tags for a sequence of interest. See 210. Coverages are determined per sample. In various implementations, coverages are determined over all chromosomes (entire reference genome), over a subset of chromosomes, or at the sub-chromosomal level. Various techniques may be used to determine the coverage, including but not limited to those shown hereinafter. In some implementations, the coverage is determined by: dividing the reference genome into a plurality of bins, determining a number of sequence tags aligning to each bin, and determining the coverage of the sequence tags using the numbers of sequence tags in bins in the sequence of interest. In some implementations, the method further includes adjusting the number of sequence tags aligning to the bins by accounting for bin-to-bin variations due to factors other than copy number variations. More detailed descriptions of methods for determining coverage are provided hereinafter.

The next step in process 200 is a QC step. It involves determining whether the test sample is within an exclusion region based on the coverage of sequence tags determined in 208 and the fetal fraction determined in 204. The exclusion region is defined by at least a fetal fraction LOD curve. The fetal fraction LOD curve varies with coverage values and indicates minimum values of fetal fractions needed to achieve a detection criterion given different coverages. See FIG. 14 for examples of the LOD curve.

In some implementations, the fetal fraction LOD curve is obtained using training samples that are affected by a CNV. The affected samples may include in silico samples obtained by combining sequence reads from different individuals. In some implementations, the affected samples are obtained by combining physical samples having two or more fetal fractions, thereby providing synthetic samples having intermediate fetal fraction values. In some implementations, the fetal fraction LOD curve is obtained using affected samples and unaffected samples with regard to the CNV. In some implementations, the LOD curve can be derived using physical or simulated samples, In some implementations, the detection criterion is a desired level of confidence that given an observed fetal fraction the ground truth fetal fraction is larger than a specified LOD. An LOD is the minimal level of signals (analytes, fetal fraction, scores indicating conditions, etc.) that can be detected with a defined confidence. In the context of this application, an LOD is the minimal level of fetal fraction (or other analytes) required to detect an aneuploidy/CNV with a defined confidence. Note that two confidence values are involved: the first confidence is for the ground truth fetal fraction being larger than a specified LOD fetal fraction, and the second confidence is for the LOD itself. In some implementations, the detection criterion is X % confident that for the observed fetal fraction the ground truth fetal fraction is larger than LOD Y %. The ground truth fetal fraction is the actual fetal fraction underlying the inferred fetal fraction. In some implementations, X is about 50%, 55%, 60%, 65%, 70%, 75%, 80%, 85%, 90%, 95%, 99%, or 99.5%. In some implementations, Y is about 50%, 55%, 60%, 65%, 70%, 75%, 80%, 85%, 90%, 95%, or 99% confidence of detection. In some implementations, X is 80% and Y is 95%. In other words, the detection criterion is 80% confident that for an observed fetal fraction the ground truth fetal fraction is larger than LOD95% or simply LOD95, LOD95 being a smallest fetal fraction value at which a CNV or aneuploidy can be detected 95% of the time. In other implementations, X is 50% and Y is 95%.

Figure 5:
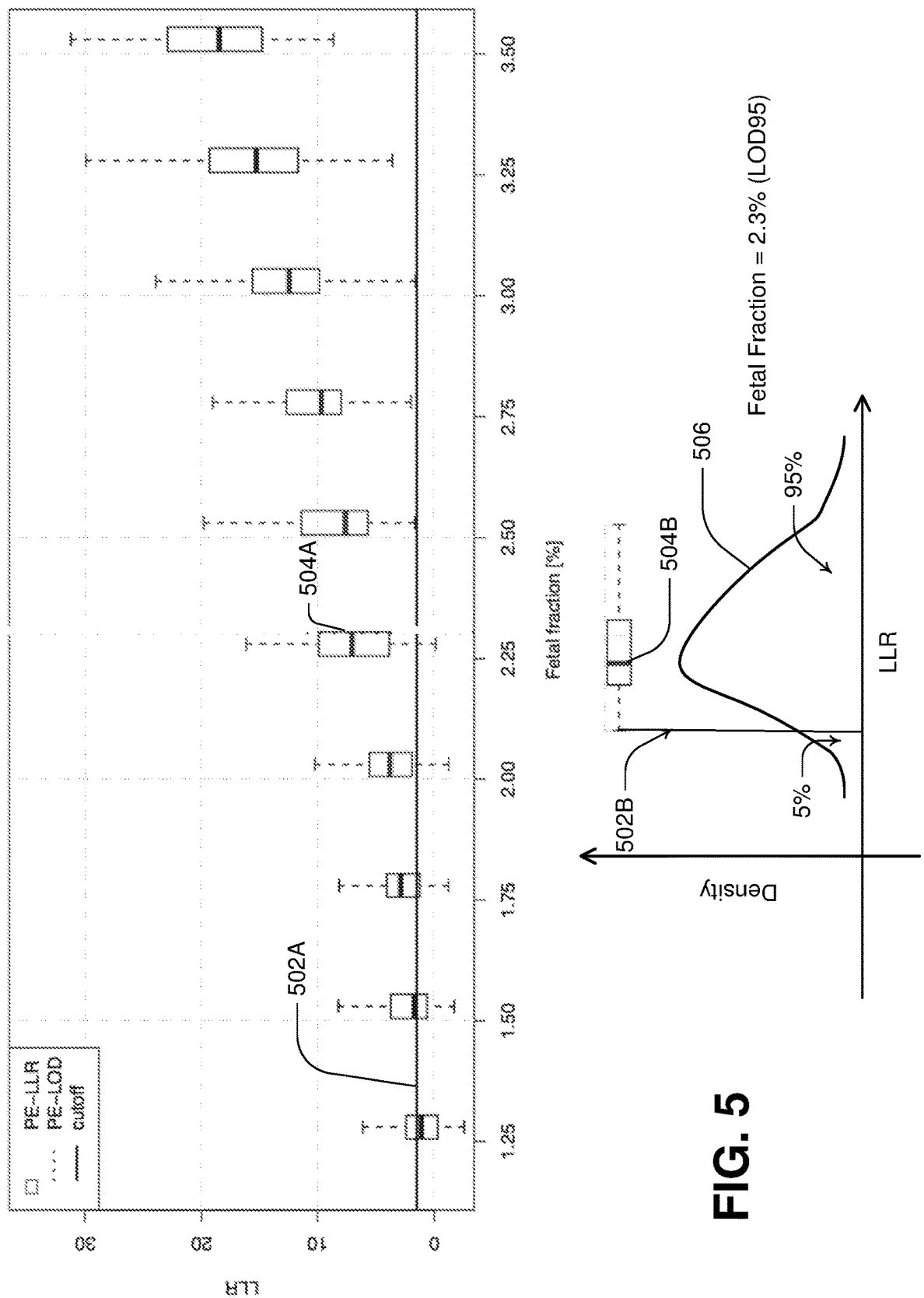
FIG. 5 shows empirical and hypothetical data illustrating the statistical concepts underlying LOD.

In some implementations, the specified LOD is determined as a smallest observed fetal fraction in which Y percent of the affected samples can be detected. In some implementations, the detection criterion for an observed fetal fraction and observed coverage is obtained using a distribution of true fetal fractions (or simulated fetal fraction) of the observed fetal fraction at the observed coverage. FIG. 5 shows empirical and hypothetical data illustrating the statistical concepts underlying LOD. The CNV detection is based on a log likelihood ratio indicating the likelihood that a sample harbors CNV. The top panel shows LLR on the Y axis and fetal fraction on the X axis. At each fetal fraction level, multiple samples are measured and the mean and standard deviation can be obtained. Given the sample data, one can infer the population distribution of LLR for each level of fetal fraction. The top panel shows that a cutoff value (labeled 502A) is applied to call the CNV. As the fetal fraction value increases, the LLR scores also increase, moving further away from the cutoff, allowing more samples to be detected.

In this example, 2.3% is the lowest fetal fraction at which an aneuploidy/CNV can be detected with 95% confidence (one-tailed). The observed LLR for affected samples at fetal fraction 2.3% is shown as 504A in the top panel and 504B in the bottom panel. The underlying population distribution of the observed data is shown in the bottom panel as 506. The cutoff LLR is shown as 502A in the top panel, and 502B in the bottom panel. The bottom panel illustrates that at fetal fraction 2.3%, 5% of the underlying population are below the LLR cutoff, and 95% of the population are above the LLR threshold 502B. As such, 95% of the samples in the population are detected as having CNV.

Figure 6:
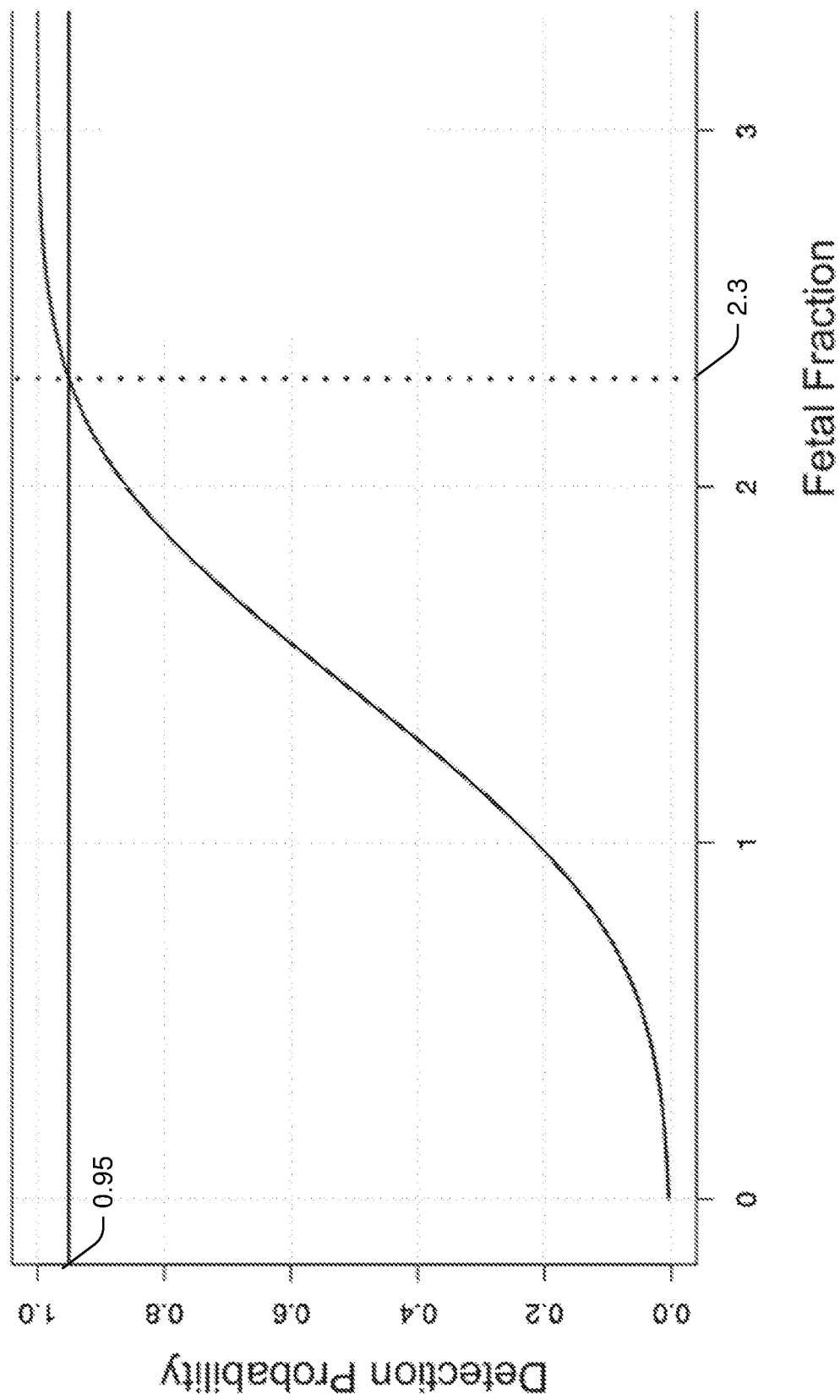
FIG. 6 shows the detection probability as a function of fetal fraction.

As can be seen in FIG. 5 top panel, as fetal fraction increases, LLR and detection probability increase as well. FIG. 6 shows the detection probability as a function of fetal fraction. In this example, a fetal fraction of 2.3% has a detection probability of 95%. So here the fetal fraction LOD95 is 2.3%.

Returning to FIG. 4A, if it is decided that the test sample is not within the exclusion region defined by the fetal fraction LOD curve, the process proceeds to evaluate coverage of the sequence of interest to determine CNV. See the "NO" branch from box 212 to box 14. And that ends the process in this path. If it is determined that the test sample is within the LOD exclusion region, and it is determined that the sample should be re-sequenced, the "YES" branch of box 212 and the "YES" branch of box 216. Then the sample is re-sequenced and the process repeats from 202 through 212. If it is determined at box 216 that the sequence does not need to be re-sequenced, such as when it was already re-sequenced, the process ends.

As shown herein after in the experimental data, the QC methods disclosed can help to increase both sensitivity and specificity. If one wishes to only improve sensitivity, one may first determine that the test sample is negative or positive. Only samples that are negatively called go through the QC process as shown in FIG. 4B.

Figure 4B:
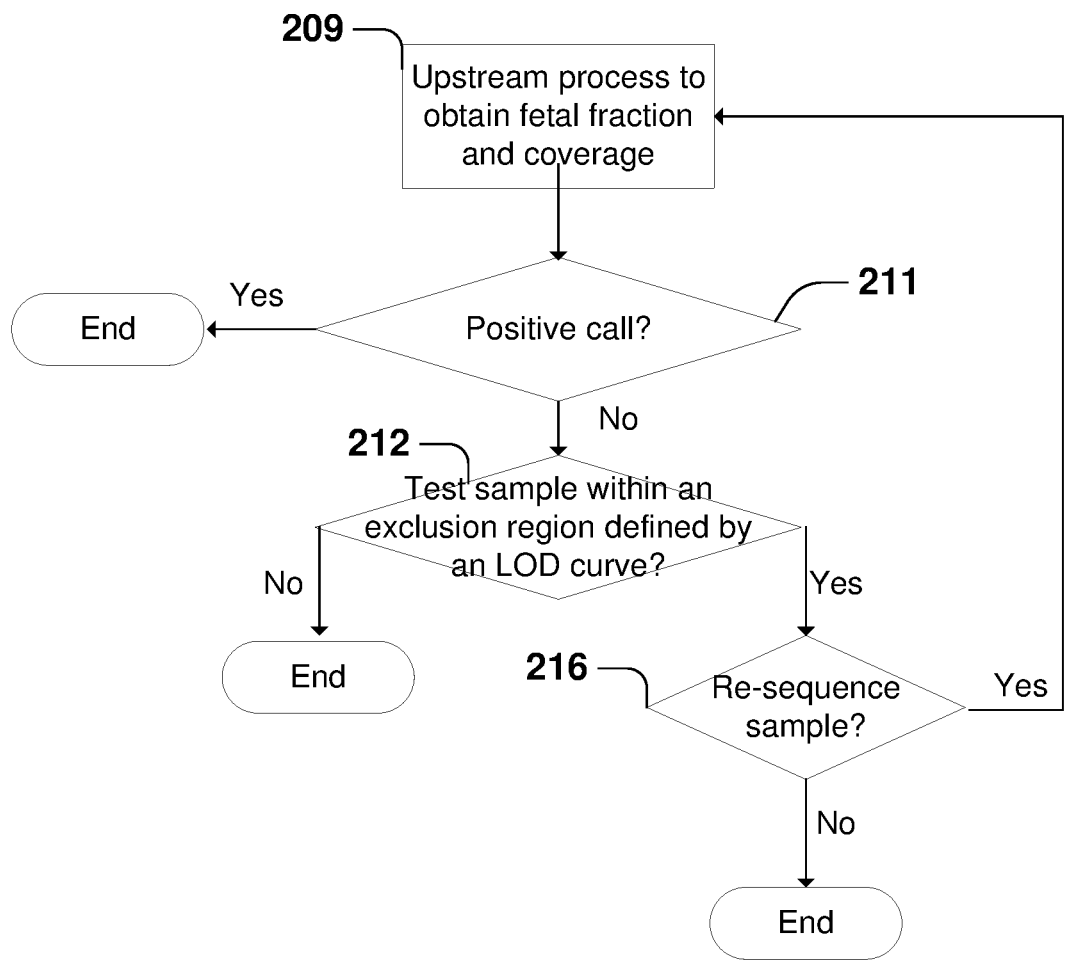
FIG. 4B shows another LOD QC process for CNV detection.

FIG. 4B shows a LOD QC process for CNV detection that is similar to the process in FIG. 4A, except that a call is first performed before determining whether the sample falls in the exclusion region. See block 211. If the call is negative, the process then determines whether the sample is within the exclusion region defined by an LOD curve. See block 212. If not, the process ends. See the "NO" branch of box 216. If the test sample is within the exclusion region, ("YES" branch of box 212) and it is determined that re-sequenced is needed, then the sample will be re-sequenced and repeat the process. If it is determined that the sample does not need to be re-sequenced, such as in the case that it has already been re-sequenced once, then the process ends. See the "NO" branch of box 216.

LOD and LOD Curve

Figure 7:
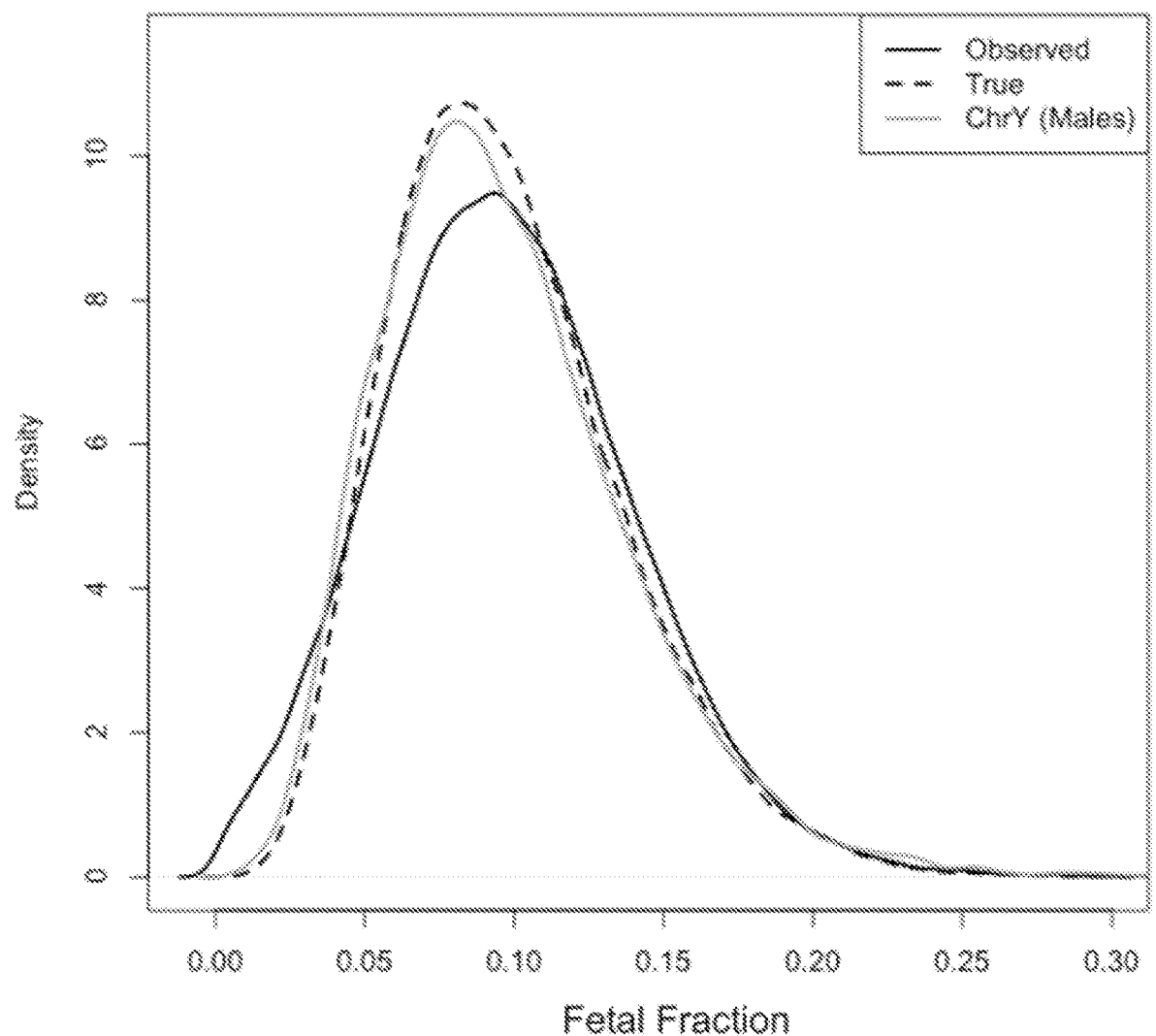
FIG. 7 shows that estimated fetal fractions include errors causing the estimated fetal fractions to deviate from the true fetal fractions.

FIG. 7 shows that estimated fetal fractions include errors causing the estimated fetal fractions to deviate from the true fetal fractions. The solid line shows an observed fetal fraction distribution. The dash line shows the true fetal fraction distribution. The observed fetal fraction is inferred from other variables instead of directly measured from fetal DNA fragments and maternal DNA fragments. The gray line is the distribution of fetal fractions that are directly measured from fetal Y chromosome. Because it is directly measured, it is closer to the true fetal fraction than the observed fetal fraction.

Figure 8:
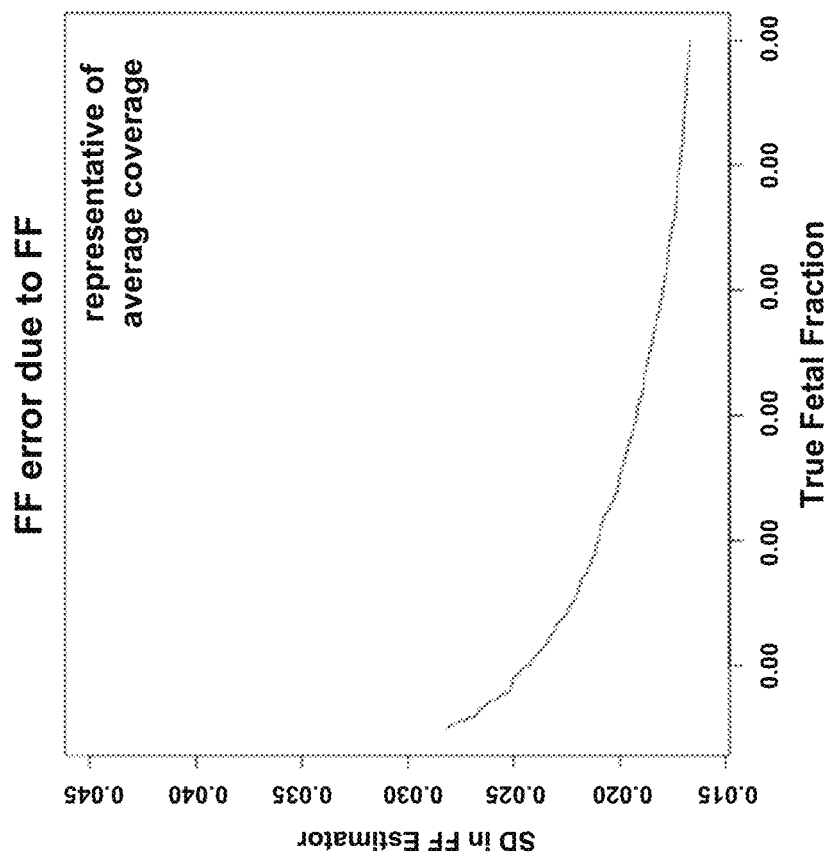
FIG. 8 shows fetal fraction error due to coverage and due to fetal fraction values.
Figure 8:
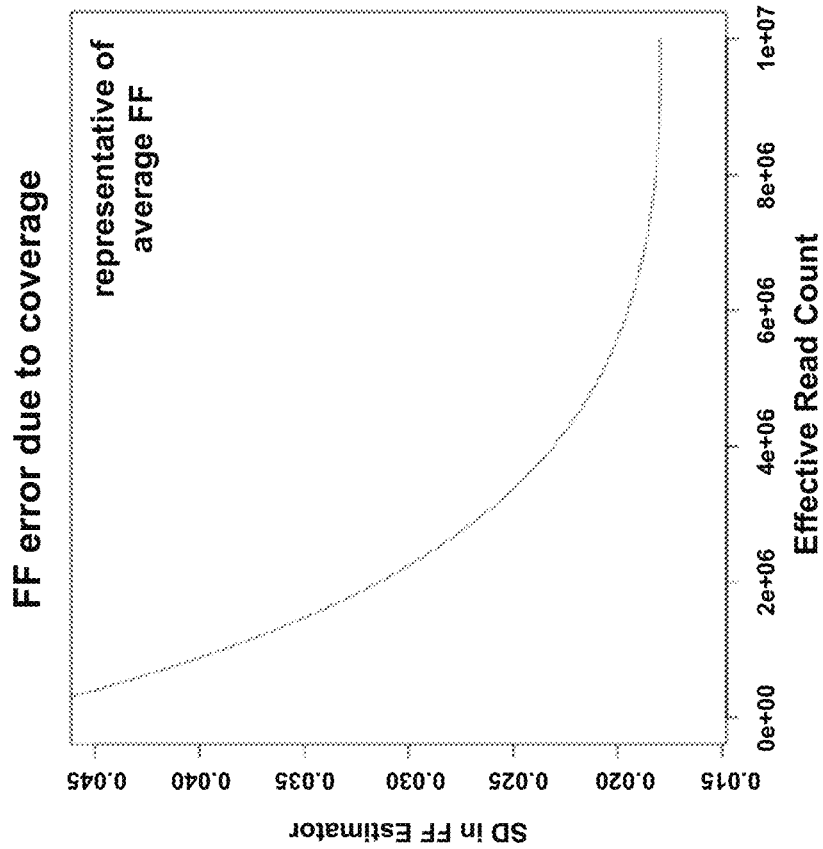

FIG. 8 shows fetal fraction error due to coverage and due to fetal fraction values. The left panel shows that the standard deviation of fetal fraction estimates (a measure related to error) decreases as coverage increases. The right panel shows that the standard deviation of fetal fraction estimates decreases as the true fetal fraction increases.

Figure 9:
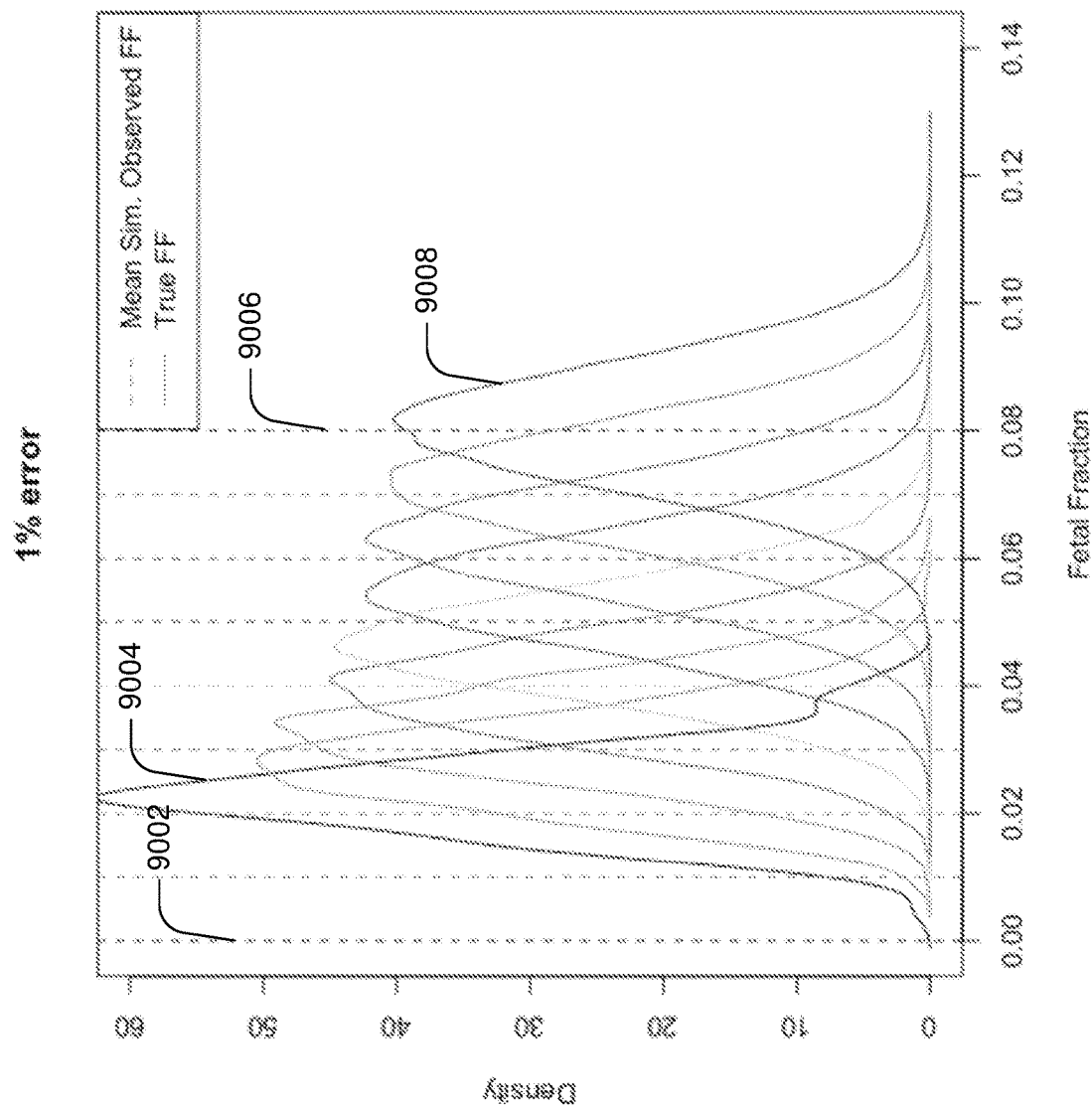
FIG. 9 simulate the true fetal fractions for eight levels of observed fetal fractions.

FIG. 9 simulate the true fetal fractions for eight levels of observed fetal fractions. It shows observed fetal fractions at 1% interval between 0% and 8%. It also shows the ground truth distributions for those observed fetal fractions. The vertical dash line 9002 shows an observed fetal fraction 0%. Solid line 9004 is the distribution of the true fetal fraction for the observed fetal fraction at 0%. Dash line 9006 indicates the observed fetal fraction of 8%. Solid line 9008 shows the distribution of true fetal fraction for the observed fetal fraction of 8%. As the figure illustrates, when an observed fetal fraction is low, such as at line 9002 and 0%, the ground truth fetal fraction distribution 9004 deviates further away from the observed fetal fraction than true fetal fraction at 8% (9008) deviates from the 8% observed fetal fraction (9006). Also, kurtosis of lower fetal fraction distributions tends to be larger. In other words, as the observed fetal fraction increases, the distribution of the true fetal fraction becomes flatter and is less deviated from the observed fetal fraction.

Figure 10:
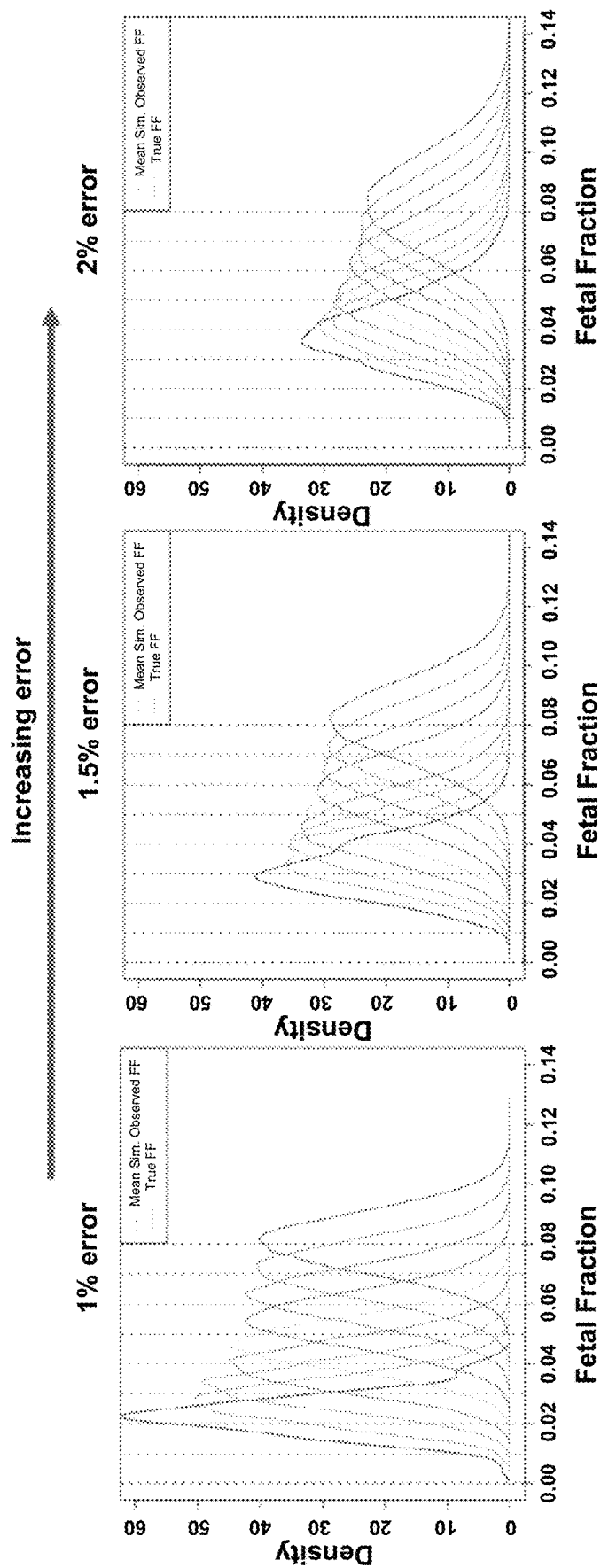
FIG. 10 shows the distributions of true fetal fraction relative to observed fetal fractions for three different levels of error or coverage.

FIG. 10 shows the distributions of true fetal fraction relative to observed fetal fractions for three different levels of error or coverage (noting that coverage inversely correlates with error). The left panel of FIG. 10 is the same as FIG. 9. It is simulated with 1% fetal fraction error. The middle panel shows the distributions for fetal fractions with 1.5% error. The right panel shows the distributions of fetal fraction in 2% error. As can be seen from the figure, the difference between the observed fetal fraction and true fetal fraction is affected by coverage, such that larger error leads to larger difference between the observed fetal fraction and true fetal fraction.

Figure 11:
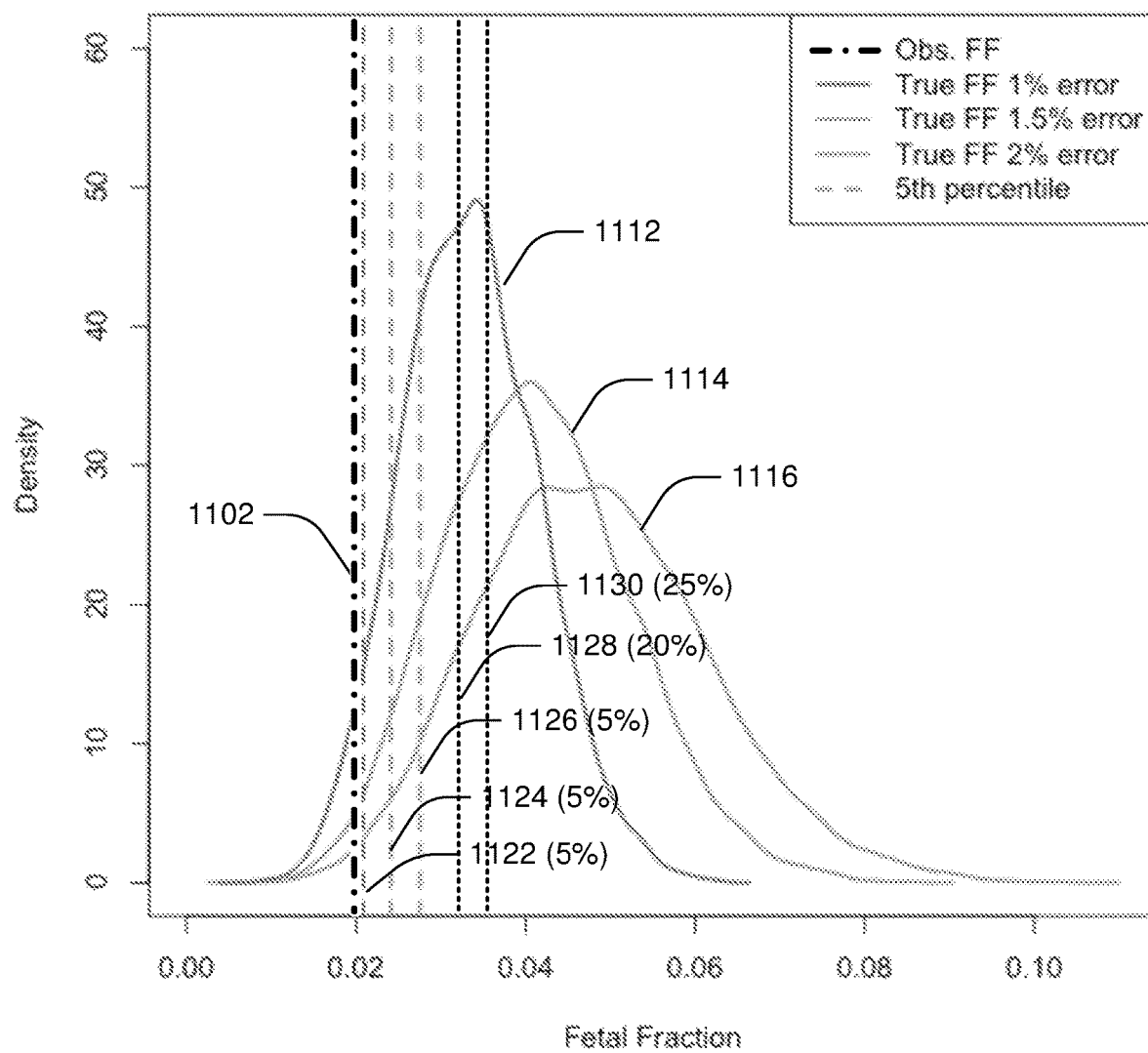
FIG. 11 shows observed fetal fraction of 2% and its simulated true fetal fraction distributions given different errors or coverage.

FIG. 11 shows observed fetal fraction of 2% and its simulated true fetal fraction distributions given different errors or coverage. The observed fetal fraction is indicated by line 1102. The true fetal fraction with the smallest error 1% (or highest coverage) has a distribution 1112. Distribution 1114 is the true fetal fraction 1.5% error or intermediate coverage. Distribution 1116 is the true fetal fraction distribution with the highest 2% error or the lowest coverage. The 5th percentile or 95% confidence for distributions 1112, 1114, 1116 are marked by lines 1122, 1124, and 1126, respectively. They show that as error increases or coverage decreases, the true fetal fraction deviates further from the observed fetal fraction, and the 95% confidence level also increases. Also shown in FIG. 11 are 20 percentile (1128) and 25 percentile (1130) of distribution 1116. They correspond to 80% confidence level and 75% confidence level respectively. Similarly, other confidence levels such as 50% confidence may be determined.

Figure 12:
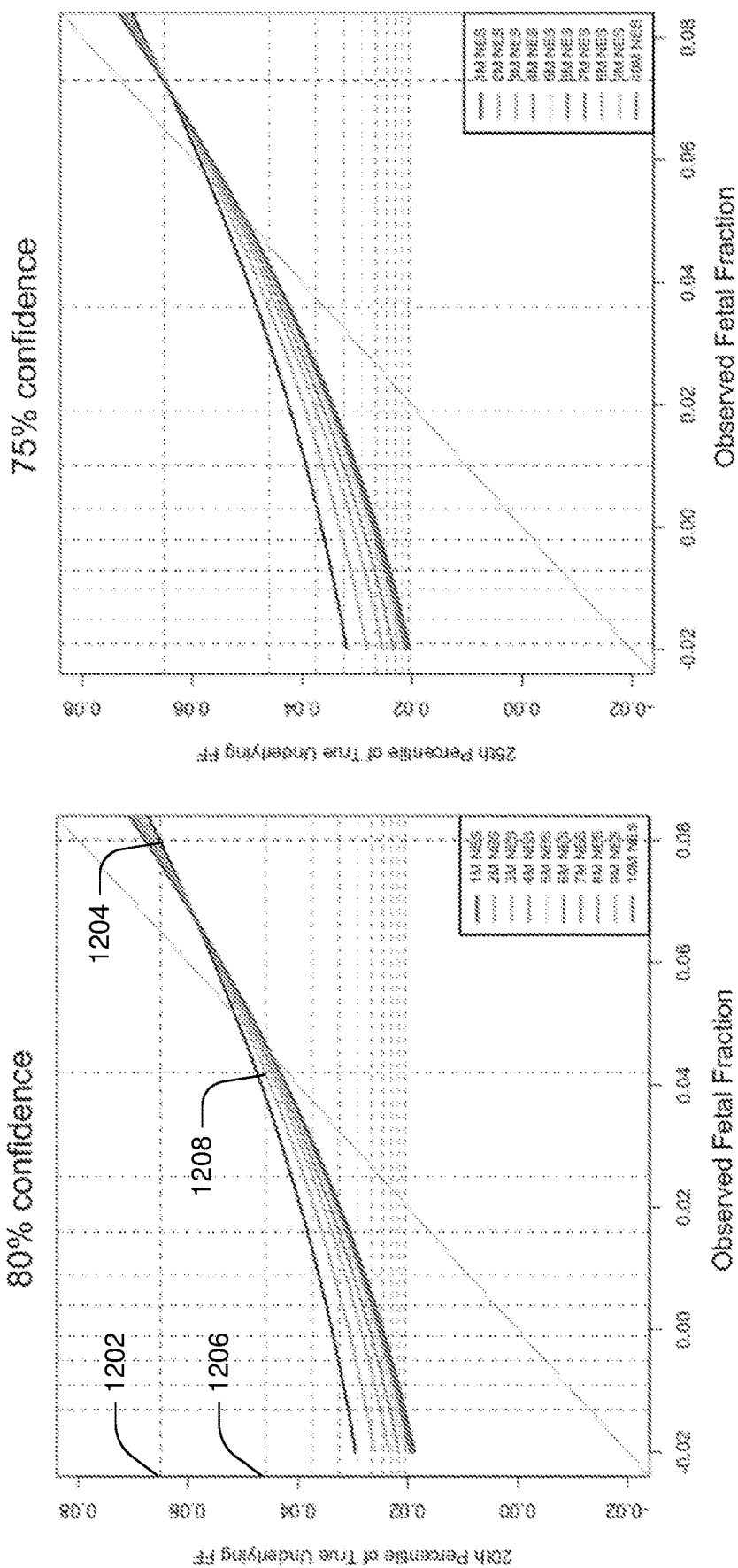
FIG. 12 shows the 20th percentile of true fetal fraction distribution as a function of the observed fetal fraction.

FIG. 12 shows the 20th percentile of true fetal fraction distribution as a function of the observed fetal fraction. As observed fetal fraction increases, the 20th percentile of true fetal fraction also increases correspondingly. The left panel shows 80% confidence data, namely 20th percentile of the true fetal fraction distribution. Right panel shows 75% confidence data. In the left panel, the relation between 20th percentile true fetal fraction and the observed fetal fraction are shown as different lines, each line indicating a different coverage level (and corresponding FF error level). Ten different levels of coverage (1M-10M) are shown. The figure shows the relation among three variables: observed fetal fraction, true fetal fraction at $20^{th}$ percentile (or 80% confidence), and coverage. Examining, e.g., the left panel, one sees two patterns at 2% observed FF (corresponding to the observed FF in FIG. 11), (a) the $20^{th}$ percentile (or 80% confidence) of true FF is higher than 2%, and (b) as coverage decreases (or error increases), the $20^{th}$ percentile (or 80% confidence) of true FF increases. These two patterns are also seen in FIG. 11.

At the low end of observed fetal fraction, as coverage decreases, the 20th percentile of true fetal fraction increases. On the high end of the observed fetal fraction, that relation reversed. To calculate the LOD curve, LOD95 is first empirically determined for a particular coverage as (as fetal fraction). This LOD95 value is also the value for the desired, e.g., 20 percentile, true fetal fraction. With this value, one can determine the observed fetal fraction from the true vs observed functions (lines in the left panel of FIG. 12).

For instance, the LOD95 for coverage 1 million is empirically determined to be 6.50% FF, which is also the 20th percentile of the true fetal fraction at 1202. One can determine from the figure that the observed fetal fraction is 8% (as indicated at 1204). The LOD95 for coverage 2 million is empirically determined to be 4.59% FF, which is also the 20th percentile of the true fetal fraction at 1206. One can determine from the figure that the observed fetal fraction is 4.2% (as indicated at 1208). One can similarly obtain the observed fetal fraction for other coverages from other lines in the figure. These points are observed fetal fractions required to have 80% confidence that its true fetal fraction exceeds the LOD95 for different coverage.

FIG. 13 tabulates the LOD, coverage, and observed fetal fraction. The table shows the effective read count in the first column from the left, LOD95 in the third column, and observed fetal fraction required to achieve 80% confidence that the true fetal fraction is above LOD95 in the fourth column. The observed fetal fraction required to have a 75% confidence is shown in the right column, which may be obtained from the data shown in the right panel of FIG. 12. The second column shows FF errors for the different effective read counts, illustrating that as coverage increases, error decreases.

Figure 14:
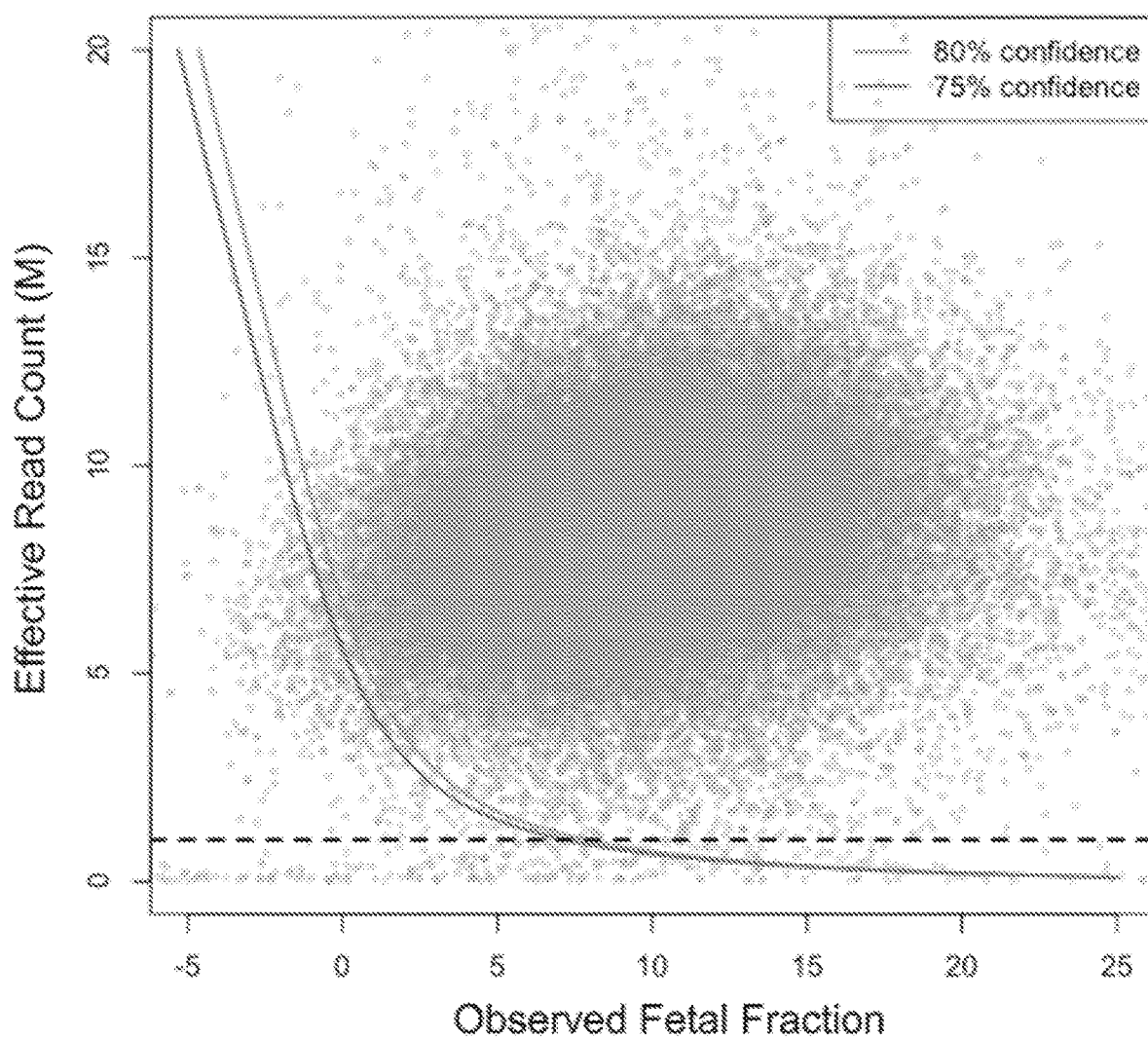
FIG. 14 includes two fetal fraction LOD curves that may be obtained from data similar to those shown in FIG. 13.

FIG. 14 includes two fetal fraction LOD curves that may be obtained from data similar to those shown in FIG. 13. In some implementations, the LOD curve is used in conjunction with coverage threshold such as 1 M coverage threshold shown in FIG. 14.

In some implementations, as shown in FIG. 14, the exclusion region is under the fetal fraction LOD curve. Put numerically, the exclusion region is the area in which each point has a lower value in fetal fraction or and/or coverage than the corresponding points on the fetal fraction LOD curve. In some implementations, the exclusion region is defined by the fetal fraction LOD curve and a coverage threshold. The exclusion region is under both the fetal fraction LOD curve and the coverage threshold.

In some implementations, the method of generating an LOD curve may be summarized as follows. An LOD curve was obtained using simulating "samples" where each "sample" includes the following.

A coverage value sampled from the known normal distribution of coverage values in clinical samples An underlying true FF value sampled from the known underlying true FF distribution as determined from the observed FF distribution in clinical samples An observed FF value determined by adding error (corresponding to the coverage value) to the underlying true FF value A very large number of such "samples" were simulated. For each observed fetal fraction value (in decimal increments), and at each coverage level (1-10M in increments), all the corresponding true FF values in this dataset were gathered, and the 100 minus X percentile of these true FF values was selected. For each possible observed FF value and coverage combination, there is now a single true FF value and we can say given this observed FF value, we are X % confident that the true FF is at least as high as the selected true FF.

For each coverage level, the observed FF was plotted versus the selected true FF to give those plots with one curved line per coverage level.

Separate from this, a LOD study such as that of Example 1 describes the relationship between coverage and LOD95 (the derivation of this relationship involves affected samples). The LOD95(Y) values corresponding to coverage levels 1-10M (in increments) from this plot were then superimposed on the plot of observed FF vs. true FF described above. The point at which each of these horizontal LOD95(Y) lines intersected the corresponding (by coverage) curved lines on the observed FF vs. true FF plot was read off the x-axis to give the observed FF required to be X % sure that the true FF exceeded the LOD95(Y).

Then the coverage values were plotted against the observed FF required to obtain the LODQC curve.

Evaluating CNV

Methods for Determination of CNV

Using the sequence coverage value, fragment size parameters, and/or methylation levels provided by the methods disclosed herein, one can determine various genetic conditions related to copy number and CNV of sequences, chromosomes, or chromosome segments with improved sensitivity, selectivity, and/or efficiency relative to using sequence coverage values obtained by conventional methods. For example, in some embodiments, the masked reference sequences are used for determining the presence or absence of any two or more different complete fetal chromosomal aneuploidies in a maternal test sample comprising fetal and maternal nucleic acid molecules. Exemplary methods provided below align reads to reference sequences (including reference genomes). The alignment can be performed on an unmasked or masked reference sequence, thereby yielding sequence tags mapped to the reference sequence. In some embodiments, only sequence tags falling on unmasked segments of the reference sequence are taken into account to determine copy number variation.

In some embodiments, assessing a nucleic acid sample for CNV involves characterizing the status of a chromosomal or segment aneuploidy by one of three types of calls: "normal" or "unaffected," "affected," and "no-call." Thresholds for calling normal and affected are typically set. A parameter related to aneuploidy or other copy number variation is measured in a sample and the measured value is compared to the thresholds. For duplication type aneuploidies, a call of affected is made if a chromosome or segment dose (or other measured value sequence content) is above a defined threshold set for affected samples. For such aneuploidies, a call of normal is made if the chromosome or segment dose is below a threshold set for normal samples. By contrast for deletion type aneuploidies, a call of affected is made if a chromosome or segment dose is below a defined threshold for affected samples, and a call of normal is made if the chromosome or segment dose is above a threshold set for normal samples. For example, in the presence of trisomy the "normal" call is determined by the value of a parameter, e.g., a test chromosome dose that is below a user-defined threshold of reliability, and the "affected" call is determined by a parameter, e.g., a test chromosome dose, that is above a user-defined threshold of reliability. A "no-call" result is determined by a parameter, e.g., a test chromosome dose that lies between the thresholds for making a "normal" or an "affected" call. The term "no-call" is used interchangeably with "unclassified".

The parameters that may be used to determine CNV include, but are not limited to, coverage, fragment size biased/weighted coverage, fraction or ratio of fragments in a defined size range, and methylation level of fragments. As discussed herein, coverage is obtained from counts of reads aligned to a region of a reference genome and optionally normalized to produce sequence tag counts. In some embodiments, sequence tag counts can be weighted by fragment size.

In some embodiments, a fragment size parameter is biased toward fragment sizes characteristic of one of the genomes. A fragment size parameter is a parameter that relates to the size of a fragment. A parameter is biased toward a fragment size when: 1) the parameter is favorably weighted for the fragment size, e.g., a count weighted more heavily for the size than for other sizes; or 2) the parameter is obtained from a value that is favorably weighted for the fragment size, e.g., a ratio obtained from a count weighted more heavily for the size. A size is characteristic of a genome when the genome has an enriched or higher concentration of nucleic acid of the size relative to another genome or another portion of the same genome.

In some embodiments, the method for determining the presence or absence of any complete fetal chromosomal aneuploidies in a maternal test sample comprises (a) obtaining sequence information for fetal and maternal nucleic acids in the maternal test sample; (b) using the sequence information and the method described above to identify a number of sequence tags, sequence coverage quantity, a fragment size parameter, or another parameter for each of the chromosomes of interest selected from chromosomes 1-22, X and Y and to identify a number of sequence tags or another parameter for one or more normalizing chromosome sequences; (c) using the number of sequence tags or the other parameter identified for each of the chromosomes of interest and the number of sequence tags or the other parameter identified for each of the normalizing chromosomes to calculate a single chromosome dose for each of the chromosomes of interests; and (d) comparing each chromosome dose to a threshold value, and thereby determining the presence or absence of any complete fetal chromosomal aneuploidies in the maternal test sample.

In some embodiments, step (a) described above can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags or the other parameter identified for each of the chromosomes of interest and the number of sequence tags or the other parameter identified for the normalizing chromosome sequence(s). In some other embodiments, chromosome dose is based on processed sequence coverage quantities derived from the number of sequence tags or another parameter. In some embodiments, only unique, non-redundant sequence tags are used to calculate the processed sequence coverage quantities or another parameter. In some embodiments, the processed sequence coverage quantity is a sequence tag density ratio, which is the number of sequence tag standardized by sequence length. In some embodiments, the processed sequence coverage quantity or the other parameter is a normalized sequence tag or another normalized parameter, which is the number of sequence tags or the other parameter of a sequence of interest divided by that of all or a substantial portion of the genome. In some embodiments, the processed sequence coverage quantity or the other parameter such as a fragment size parameter is adjusted according to a global profile of the sequence of interest. In some embodiments, the processed sequence coverage quantity or the other parameter is adjusted according to the within-sample correlation between the GC content and the sequence coverage for the sample being tested. In some embodiments, the processed sequence coverage quantity or the other parameter results from combinations of these processes, which are further described elsewhere herein.

In some embodiments, a chromosome dose is calculated as the ratio of the processed sequence coverage or the other parameter for each of the chromosomes of interest and that for the normalizing chromosome sequence(s).

In any one of the embodiments above, the complete chromosomal aneuploidies are selected from complete chromosomal trisomies, complete chromosomal monosomies and complete chromosomal polysomies. The complete chromosomal aneuploidies are selected from complete aneuploidies of any one of chromosome 1-22, X, and Y. For example, the said different complete fetal chromosomal aneuploidies are selected from trisomy 2, trisomy 8, trisomy 9, trisomy 20, trisomy 21, trisomy 13, trisomy 16, trisomy 18, trisomy 22, 47,XXX, 47,XYY, and monosomy X.

In any one of the embodiments above, steps (a)-(d) are repeated for test samples from different maternal subjects, and the method comprises determining the presence or absence of any two or more different complete fetal chromosomal aneuploidies in each of the test samples.

In any one of the embodiments above, the method can further comprise calculating a normalized chromosome value (NCV), wherein the NCV relates the chromosome dose to the mean of the corresponding chromosome dose in a set of qualified samples as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.

In some embodiments, NCV can be calculated "on the fly" by relating the chromosome dose of a chromosome of interest in a test sample to the median of the corresponding chromosome dose in multiplexed samples sequenced on the same flow cells as:

$$NCV_{ij} = \frac{x_{ij} - M_j}{\hat{\sigma}_j}$$

where $M_j$ is the estimated median for the j-th chromosome dose in a set of multiplexed samples sequenced on the same flow cell; $\hat{\sigma}_j$ is the standard deviation for the j-th chromosome dose in one or more sets of multiplexed samples sequenced on one or more flow cells, and $x_i$ is the observed j-th chromosome dose for test sample i. In this embodiment, test sample i is one of the multiplexed samples sequenced on the same flow cell from which $M_j$ is determined.

In some embodiments, a method is provided for determining the presence or absence of different partial fetal chromosomal aneuploidies in a maternal test sample comprising fetal and maternal nucleic acids. The method involves procedures analogous to the method for detecting complete aneuploidy as outlined above. However, instead of analyzing a complete chromosome, a segment of a chromosome is analyzed. See US Patent Application Publication No. 2013/0029852, which is incorporated by reference.

Figure 15:
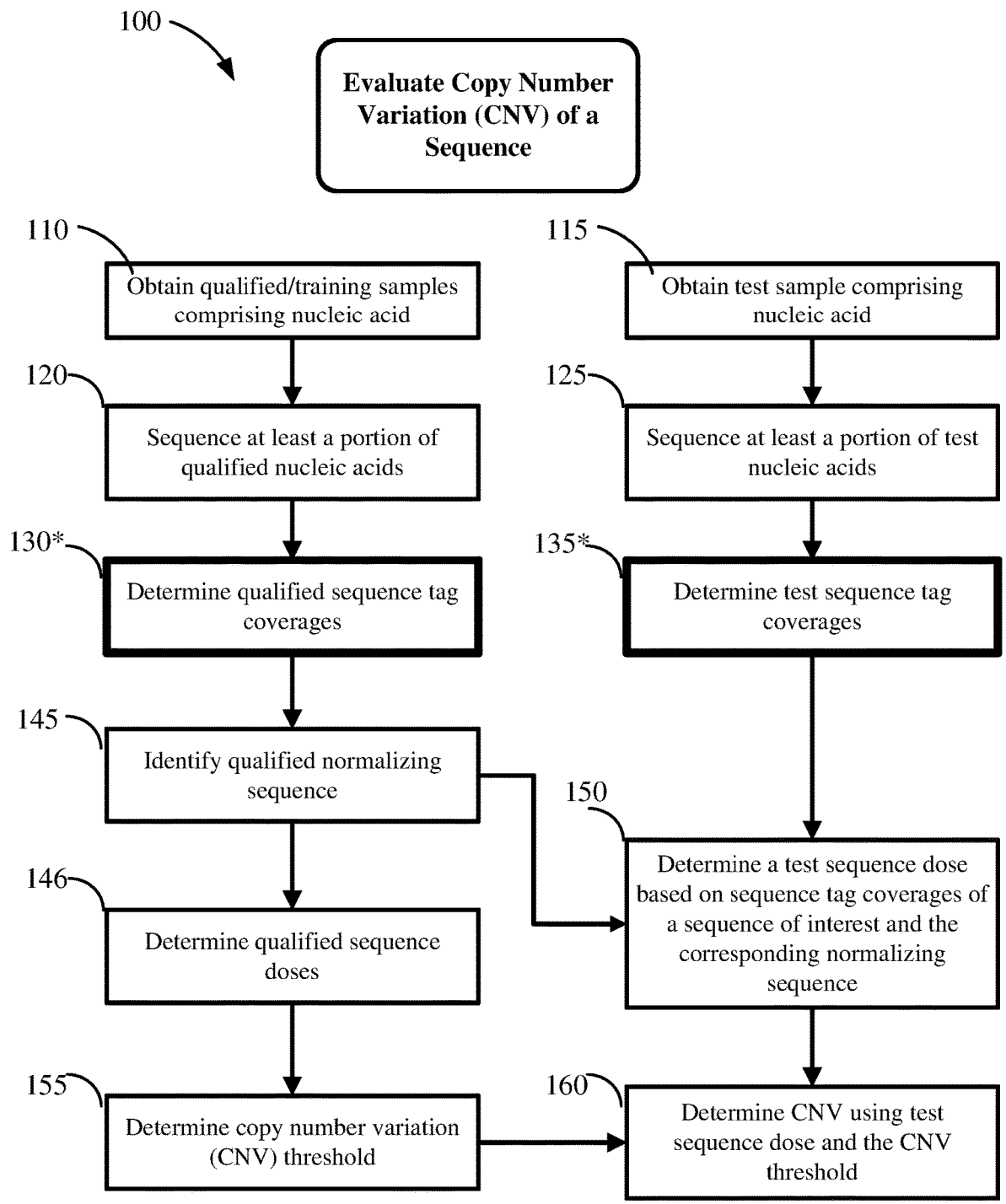
FIG. 15 shows a method for determining the presence of copy number variation in accordance with some embodiments.

FIG. 15 shows a method for determining the presence of copy number variation in accordance with some embodiments. Process 100 illustrated in FIG. 15 uses sequence tag coverage based on the number of sequence tags (i.e., the sequence tag count) to determine CNV. However, similar to the description above for calculation of a NCV, other variables or parameters, such as size, size ratio, and methylation level, may be used instead of coverage. In some implementations, two or more variables are combined to determine a CNV. Furthermore, coverage and other parameters may be weighted based on the size of the fragments from which tags are derived. For ease of reading, only coverage is referred to in process 100 illustrated in FIG. 1, but one should note that other parameters, such as size, size ratio, and methylation level, count weighted by size, etc. may be used in place of coverage.

In operations 130 and 135, qualified sequence tag coverages (or values of another parameter) and test sequence tag coverages (or values of another parameter) are determined. The present disclosure provides processes to determine coverage quantities that provide improved sensitivity and selectivity relative to conventional methods. Operation 130 and 135 are marked by asterisks and emphasized by boxes of heavy lines to indicate these operations contribute to improvement over prior art. In some embodiments, the sequence tag coverage quantities are normalized, adjusted, trimmed, and otherwise processed to improve the sensitivity and selectivity of the analysis. These processes are further described elsewhere herein.

From an over-view perspective, the method makes use of normalizing sequences of qualified training samples in determination of CNV of test samples. In some embodiments, the qualified training samples are unaffected and have normal copy number. Normalizing sequences provide a mechanism to normalize measurements for intra-run and inter-run variabilities. Normalizing sequences are identified using sequence information from a set of qualified samples obtained from subjects known to comprise cells having a normal copy number for any one sequence of interest, e.g., a chromosome or segment thereof. Determination of normalizing sequences is outlined in steps 110, 120, 130, 145 and 146 of the embodiment of the method depicted in FIG. 1. In some embodiments, the normalizing sequences are used to calculate sequence dose for test sequences. See step 150. In some embodiments, normalizing sequences are also used to calculate a threshold against which the sequence dose of the test sequences is compared. See step 150. The sequence information obtained from the normalizing sequence and the test sequence is used for determining statistically meaningful identification of chromosomal aneuploidies in test samples (step 160).

Turning to the details of the method for determining the presence of copy number variation according to some embodiments, FIG. 15 provides a flow diagram 100 of an embodiment for determining a CNV of a sequence of interest, e.g., a chromosome or segment thereof, in a biological sample. In some embodiments, a biological sample is obtained from a subject and comprises a mixture of nucleic acids contributed by different genomes. The different genomes can be contributed to the sample by two individuals, e.g., the different genomes are contributed by the fetus and the mother carrying the fetus. Also, the different genomes can be contributed to the sample by three or more individuals, e.g., the different genomes are contributed by two or more fetuses and the mother carrying the fetuses. Alternatively, the genomes are contributed to the sample by aneuploid cancerous cells and normal euploid cells from the same subject, e.g., a plasma sample from a cancer patient.

Apart from analyzing a patient's test sample, one or more normalizing chromosomes or one or more normalizing chromosome segments are selected for each possible chromosome of interest. The normalizing chromosomes or segments are identified asynchronously from the normal testing of patient samples, which may take place in a clinical setting. In other words, the normalizing chromosomes or segments are identified prior to testing patient samples. The associations between normalizing chromosomes or segments and chromosomes or segments of interest are stored for use during testing. As explained below, such association is typically maintained over periods of time that span testing of many samples. The following discussion concerns embodiments for selecting normalizing chromosomes or chromosome segments for individual chromosomes or segments of interest.

A set of qualified samples is obtained to identify qualified normalizing sequences and to provide variance values for use in determining statistically meaningful identification of CNV in test samples. In step 110, a plurality of biological qualified samples are obtained from a plurality of subjects known to comprise cells having a normal copy number for any one sequence of interest. In one embodiment, the qualified samples are obtained from mothers pregnant with a fetus that has been confirmed using cytogenetic means to have a normal copy number of chromosomes. The biological qualified samples may be a biological fluid, e.g., plasma, or any suitable sample as described below. In some embodiments, a qualified sample contains a mixture of nucleic acid molecules, e.g., cfDNA molecules. In some embodiments, the qualified sample is a maternal plasma sample that contains a mixture of fetal and maternal cfDNA molecules. Sequence information for normalizing chromosomes and/or segments thereof is obtained by sequencing at least a portion of the nucleic acids, e.g., fetal and maternal nucleic acids, using any known sequencing method. Preferably, any one of the Next Generation Sequencing (NGS) methods described elsewhere herein is used to sequence the fetal and maternal nucleic acids as single or clonally amplified molecules. In various embodiments, the qualified samples are processed as disclosed below prior to and during sequencing. They may be processed using apparatus, systems, and kits as disclosed herein.

In step 120, at least a portion of each of all the qualified nucleic acids contained in the qualified samples are sequenced to generate millions of sequence reads, e.g., 36 bp reads, which are aligned to a reference genome, e.g., hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence reads comprise 36 bp. In another embodiment, the mapped sequence reads comprise 25 bp.

Sequence reads are aligned to a reference genome, and the reads that are uniquely mapped to the reference genome are known as sequence tags. Sequence tags falling on masked segments of a masked reference sequence are not counted for analysis of CNV.

In one embodiment, at least about 3×106 qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags comprising between 20 and 40 bp reads are obtained from reads that map uniquely to a reference genome.

In step 130, all the tags obtained from sequencing the nucleic acids in the qualified samples are counted to obtain a qualified sequence tag coverage. Similarly, in operation 135, all tags obtained from a test sample are counted to obtain a test sequence tag coverage. The present disclosure provides processes to determine coverage quantities that provides improved sensitivity and selectivity relative to conventional methods. Operation 130 and 135 are marked by asterisks and emphasized by boxes of heavy lines to indicate these operations contribute to improvement over prior art. In some embodiments, the sequence tag coverage quantities are normalized, adjusted, trimmed, and otherwise processed to improve the sensitivity and selectivity of the analysis. These processes are further described elsewhere herein.

As all qualified sequence tags are mapped and counted in each of the qualified samples, the sequence tag coverage for a sequence of interest, e.g., a clinically-relevant sequence, in the qualified samples is determined, as are the sequence tag coverages for additional sequences from which normalizing sequences are identified subsequently.

In some embodiments, the sequence of interest is a chromosome that is associated with a complete chromosomal aneuploidy, e.g., chromosome 21, and the qualified normalizing sequence is a complete chromosome that is not associated with a chromosomal aneuploidy and whose variation in sequence tag coverage approximates that of the sequence (i.e., chromosome) of interest, e.g., chromosome 21. The selected normalizing chromosome(s) may be the one or group that best approximates the variation in sequence tag coverage of the sequence of interest. Any one or more of chromosomes 1-22, X, and Y can be a sequence of interest, and one or more chromosomes can be identified as the normalizing sequence for each of the any one chromosomes 1-22, X and Y in the qualified samples. The normalizing chromosome can be an individual chromosome or it can be a group of chromosomes as described elsewhere herein.

In another embodiment, the sequence of interest is a segment of a chromosome associated with a partial aneuploidy, e.g., a chromosomal deletion or insertion, or unbalanced chromosomal translocation, and the normalizing sequence is a chromosomal segment (or group of segments) that is not associated with the partial aneuploidy and whose variation in sequence tag coverage approximates that of the chromosome segment associated with the partial aneuploidy. The selected normalizing chromosome segment(s) may be the one or more that best approximates the variation in sequence tag coverage of the sequence of interest. Any one or more segments of any one or more chromosomes 1-22, X, and Y can be a sequence of interest.

In other embodiments, the sequence of interest is a segment of a chromosome associated with a partial aneuploidy and the normalizing sequence is a whole chromosome or chromosomes. In still other embodiments, the sequence of interest is a whole chromosome associated with an aneuploidy and the normalizing sequence is a chromosomal segment or segments that are not associated with the aneuploidy.

Whether a single sequence or a group of sequences are identified in the qualified samples as the normalizing sequence(s) for any one or more sequences of interest, the qualified normalizing sequence may be chosen to have a variation in sequence tag coverage or a fragment size parameter that best or effectively approximates that of the sequence of interest as determined in the qualified samples. For example, a qualified normalizing sequence is a sequence that produces the smallest variability across the qualified samples when used to normalize the sequence of interest, i.e., the variability of the normalizing sequence is closest to that of the sequence of interest determined in qualified samples. Stated another way, the qualified normalizing sequence is the sequence selected to produce the least variation in sequence dose (for the sequence of interest) across the qualified samples. Thus, the process selects a sequence that when used as a normalizing chromosome is expected to produce the smallest variability in run-to-run chromosome dose for the sequence of interest.

The normalizing sequence identified in the qualified samples for any one or more sequences of interest remains the normalizing sequence of choice for determining the presence or absence of aneuploidy in test samples over days, weeks, months, and possibly years, provided that procedures needed to generate sequencing libraries, and sequencing the samples are essentially unaltered over time. As described above, normalizing sequences for determining the presence of aneuploidies are chosen for (possibly among other reasons as well) the variability in the number of sequence tags or values of the fragment size parameter that are mapped to it among samples, e.g., different samples, and sequencing runs, e.g., sequencing runs that occur on the same day and/or different days, that best approximates the variability of the sequence of interest for which it is used as a normalizing parameter. Substantial alterations in these procedures will affect the number of tags that are mapped to all sequences, which in turn will determine which one or group of sequences will have a variability across samples in the same and/or in different sequencing runs, on the same day or on different days that most closely approximates that of the sequence(s) of interest, which would require that the set of normalizing sequences be re-determined. Substantial alterations in procedures include changes in the laboratory protocol used for preparing the sequencing library, which includes changes related to preparing samples for multiplex sequencing instead of singleplex sequencing, and changes in sequencing platforms, which include changes in the chemistry used for sequencing.

In some embodiments, the normalizing sequence chosen to normalize a particular sequence of interest is a sequence that best distinguishes one or more qualified, samples from one or more affected samples, which implies that the normalizing sequence is a sequence that has the greatest differentiability, i.e., the differentiability of the normalizing sequence is such that it provides optimal differentiation to a sequence of interest in an affected test sample to easily distinguish the affected test sample from other unaffected samples. In other embodiments, the normalizing sequence is a sequence that has a combination of the smallest variability and the greatest differentiability.

The level of differentiability can be determined as a statistical difference between the sequence doses, e.g., chromosome doses or segment doses, in a population of qualified samples and the chromosome dose(s) in one or more test samples as described below and shown in the Examples. For example, differentiability can be represented numerically as a t-test value, which represents the statistical difference between the chromosome doses in a population of qualified samples and the chromosome dose(s) in one or more test samples. Similarly, differentiability can be based on segment doses instead of chromosome doses. Alternatively, differentiability can be represented numerically as a Normalized Chromosome Value (NCV), which is a z-score for chromosome doses as long as the distribution for the NCV is normal. Similarly, in the case where chromosome segments are the sequences of interest, differentiability of segment doses can be represented numerically as a Normalized Segment Value (NSV), which is a z-score for chromosome segment doses as long as the distribution for the NSV is normal. In determining the z-score, the mean and standard deviation of chromosome or segment doses in a set of qualified samples can be used. Alternatively, the mean and standard deviation of chromosome or segment doses in a training set comprising qualified samples and affected samples can be used. In other embodiments, the normalizing sequence is a sequence that has the smallest variability and the greatest differentiability or an optimal combination of small variability and large differentiability.

The method identifies sequences that inherently have similar characteristics and that are prone to similar variations among samples and sequencing runs, and which are useful for determining sequence doses in test samples.

Determination of Sequence Doses

In some embodiments, chromosome or segment doses for one or more chromosomes or segments of interest are determined in all qualified samples as described in step 146 shown in FIG. 1, and a normalizing chromosome or segment sequence is identified in step 145. Some normalizing sequences are provided before sequence doses are calculated. Then one or more normalizing sequences are identified according to various criteria as further described below, see step 145. In some embodiments, e.g., the identified normalizing sequence results in the smallest variability in sequence dose for the sequence of interest across all qualified samples.

In step 146, based on the calculated qualified tag densities, a qualified sequence dose, i.e., a chromosome dose or a segment dose, for a sequence of interest is determined as the ratio of the sequence tag coverage for the sequence of interest and the qualified sequence tag coverage for additional sequences from which normalizing sequences are identified subsequently in step 145. The identified normalizing sequences are used subsequently to determine sequence doses in test samples.

In one embodiment, the sequence dose in the qualified samples is a chromosome dose that is calculated as the ratio of the number of sequence tags or fragment size parameter for a chromosome of interest and the number of sequence tags for a normalizing chromosome sequence in a qualified sample. The normalizing chromosome sequence can be a single chromosome, a group of chromosomes, a segment of one chromosome, or a group of segments from different chromosomes. Accordingly, a chromosome dose for a chromosome of interest is determined in a qualified sample as the ratio of the number of tags for a chromosome of interest and the number of tags for (i) a normalizing chromosome sequence composed of a single chromosome, (ii) a normalizing chromosome sequence composed of two or more chromosomes, (iii) a normalizing segment sequence composed of a single segment of a chromosome, (iv) a normalizing segment sequence composed of two or more segments form one chromosome, or (v) a normalizing segment sequence composed of two or more segments of two or more chromosomes. Examples for determining a chromosome dose for chromosome of interest 21 according to (i)-(v) are as follows: chromosome doses for chromosome of interest, e.g., chromosome 21, are determined as a ratio of the sequence tag coverage of chromosome 21 and one of the following sequence tag coverages: (i) each of all the remaining chromosomes, i.e., chromosomes 1-20, chromosome 22, chromosome X, and chromosome Y; (ii) all possible combinations of two or more remaining chromosomes; (iii) a segment of another chromosome, e.g., chromosome 9; (iv) two segments of one other chromosome, e.g., two segments of chromosome 9; (v) two segments of two different chromosomes, e.g., a segment of chromosome 9 and a segment of chromosome 14.

In another embodiment, the sequence dose in the qualified samples is a segment dose as opposed to a chromosome dose, which segment dose is calculated as the ratio of the number of sequence tags for a segment of interest, that is not a whole chromosome, and the number of sequence tags for a normalizing segment sequence in a qualified sample. The normalizing segment sequence can be any of the normalizing chromosome or segment sequences discussed above.

Identification of Normalizing Sequences

In step 145, a normalizing sequence is identified for a sequence of interest. In some embodiments, e.g., the normalizing sequence is the sequence based on the calculated sequence doses, e.g., that result in the smallest variability in sequence dose for the sequence of interest across all qualified training samples. The method identifies sequences that inherently have similar characteristics and are prone to similar variations among samples and sequencing runs, and which are useful for determining sequence doses in test samples.

Normalizing sequences for one or more sequences of interest can be identified in a set of qualified samples, and the sequences that are identified in the qualified samples are used subsequently to calculate sequence doses for one or more sequences of interest in each of the test samples (step 150) to determine the presence or absence of aneuploidy in each of the test samples. The normalizing sequence identified for chromosomes or segments of interest may differ when different sequencing platforms are used and/or when differences exist in the purification of the nucleic acid that is to be sequenced and/or preparation of the sequencing library. The use of normalizing sequences according to the methods described herein provides specific and sensitive measure of a variation in copy number of a chromosome or segment thereof irrespective of sample preparation and/or sequencing platform that is used.

In some embodiments, more than one normalizing sequence is identified, i.e., different normalizing sequences can be determined for one sequence of interest, and multiple sequence doses can be determined for one sequence of interest. For example, the variation, e.g., coefficient of variation (CV=standard deviation/mean), in chromosome dose for chromosome of interest 21 is least when the sequence tag coverage of chromosome 14 is used. However, two, three, four, five, six, seven, eight or more normalizing sequences can be identified for use in determining a sequence dose for a sequence of interest in a test sample. As an example, a second dose for chromosome 21 in any one test sample can be determined using chromosome 7, chromosome 9, chromosome 11 or chromosome 12 as the normalizing chromosome sequence as these chromosomes all have CV close to that for chromosome 14.

In some embodiments, when a single chromosome is chosen as the normalizing chromosome sequence for a chromosome of interest, the normalizing chromosome sequence will be a chromosome that results in chromosome doses for the chromosome of interest that has the smallest variability across all samples tested, e.g., qualified samples. In some instances, the best normalizing chromosome may not have the least variation, but may have a distribution of qualified doses that best distinguishes a test sample or samples from the qualified samples, i.e., the best normalizing chromosome may not have the lowest variation, but may have the greatest differentiability.

In some embodiments, normalizing sequences include one or more robust autosomes sequences or segments thereof. In some embodiments, the robust autosomes include all autosomes except for the chromosome(s) of interest. In some embodiments, the robust autosomes include all autosomes except for chromosomes X, Y, 13, 18, and 21. In some embodiments, the robust autosomes include all autosomes except those determined from a sample to be deviating from a normal diploid state, which can be useful in determining cancer genomes that have abnormal copy number relative to a normal diploid genome.

Determination of Aneuploidies in Test Samples

Based on the identification of the normalizing sequence(s) in qualified samples, a sequence dose is determined for a sequence of interest in a test sample comprising a mixture of nucleic acids derived from genomes that differ in one or more sequences of interest.

In step 115, a test sample is obtained from a subject suspected or known to carry a clinically-relevant CNV of a sequence of interest. The test sample may be a biological fluid, e.g., plasma, or any suitable sample as described below. As explained, the sample may be obtained using a non-invasive procedure such as a simple blood draw. In some embodiments, a test sample contains a mixture of nucleic acid molecules, e.g., cfDNA molecules. In some embodiments, the test sample is a maternal plasma sample that contains a mixture of fetal and maternal cfDNA molecules.

In step 125, at least a portion of the test nucleic acids in the test sample is sequenced as described for the qualified samples to generate millions of sequence reads, e.g., 36 bp reads. In various embodiments, 2×36 bp paired end reads are used for paired end sequencing. As in step 120, the reads generated from sequencing the nucleic acids in the test sample are uniquely mapped or aligned to a reference genome to produce tags. As described in step 120, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^6$ qualified sequence tags comprising between 20 and 40 bp reads are obtained from reads that map uniquely to a reference genome. In certain embodiments, the reads produced by sequencing apparatus are provided in an electronic format. Alignment is accomplished using computational apparatus as discussed below. Individual reads are compared against the reference genome, which is often vast (millions of base pairs) to identify sites where the reads uniquely correspond with the reference genome. In some embodiments, the alignment procedure permits limited mismatch between reads and the reference genome. In some cases, 1, 2, or 3 base pairs in a read are permitted to mismatch corresponding base pairs in a reference genome, and yet a mapping is still made.

In step 135, all or most of the tags obtained from sequencing the nucleic acids in the test samples are counted to determine a test sequence tag coverage using a computational apparatus as described below. In some embodiments, each read is aligned to a particular region of the reference genome (a chromosome or segment in most cases), and the read is converted to a tag by appending site information to the read. As this process unfolds, the computational apparatus may keep a running count of the number of tags/reads mapping to each region of the reference genome (chromosome or segment in most cases). The counts are stored for each chromosome or segment of interest and each corresponding normalizing chromosome or segment.

In certain embodiments, the reference genome has one or more excluded regions that are part of a true biological genome but are not included in the reference genome. Reads potentially aligning to these excluded regions are not counted. Examples of excluded regions include regions of long repeated sequences, regions of similarity between X and Y chromosomes, etc. Using a masked reference sequence obtained by masking techniques described above, only tags on unmasked segments of the reference sequence are taken into account for analysis of CNV.

In some embodiments, the method determines whether to count a tag more than once when multiple reads align to the same site on a reference genome or sequence. There may be occasions when two tags have the same sequence and therefore align to an identical site on a reference sequence. The method employed to count tags may under certain circumstances exclude from the count identical tags deriving from the same sequenced sample. If a disproportionate number of tags are identical in a given sample, it suggests that there is a strong bias or other defect in the procedure. Therefore, in accordance with certain embodiments, the counting method does not count tags from a given sample that are identical to tags from the sample that were previously counted.

Various criteria may be set for choosing when to disregard an identical tag from a single sample. In certain embodiments, a defined percentage of the tags that are counted must be unique. If more tags than this threshold are not unique, they are disregarded. For example, if the defined percentage requires that at least 50% are unique, identical tags are not counted until the percentage of unique tags exceeds 50% for the sample. In other embodiments, the threshold number of unique tags is at least about 60%. In other embodiments, the threshold percentage of unique tags is at least about 75%, or at least about 90%, or at least about 95%, or at least about 98%, or at least about 99%. A threshold may be set at 90% for chromosome 21. If 30M tags are aligned to chromosome 21, then at least 27M of them must be unique. If 3M counted tags are not unique and the 30 million and first tag is not unique, it is not counted. The choice of the particular threshold or other criterion used to determine when not to count further identical tags can be selected using appropriate statistical analysis. One factor influencing this threshold or other criterion is the relative amount of sequenced sample to the size of the genome to which tags can be aligned. Other factors include the size of the reads and similar considerations.

In one embodiment, the number of test sequence tags mapped to a sequence of interest is normalized to the known length of a sequence of interest to which they are mapped to provide a test sequence tag density ratio. As described for the qualified samples, normalization to the known length of a sequence of interest is not required, and may be included as a step to reduce the number of digits in a number to simplify it for human interpretation. As all the mapped test sequence tags are counted in the test sample, the sequence tag coverage for a sequence of interest, e.g., a clinically-relevant sequence, in the test samples is determined, as are the sequence tag coverages for additional sequences that correspond to at least one normalizing sequence identified in the qualified samples.

In step 150, based on the identity of at least one normalizing sequence in the qualified samples, a test sequence dose is determined for a sequence of interest in the test sample. In various embodiments, the test sequence dose is computationally determined using the sequence tag coverages of the sequence of interest and the corresponding normalizing sequence as described herein. The computational apparatus responsible for this undertaking will electronically access the association between the sequence of interest and its associated normalizing sequence, which may be stored in a database, table, graph, or be included as code in program instructions.

As described elsewhere herein, the at least one normalizing sequence can be a single sequence or a group of sequences. The sequence dose for a sequence of interest in a test sample is a ratio of the sequence tag coverage determined for the sequence of interest in the test sample and the sequence tag coverage of at least one normalizing sequence determined in the test sample, wherein the normalizing sequence in the test sample corresponds to the normalizing sequence identified in the qualified samples for the particular sequence of interest. For example, if the normalizing sequence identified for chromosome 21 in the qualified samples is determined to be a chromosome, e.g., chromosome 14, then the test sequence dose for chromosome 21 (sequence of interest) is determined as the ratio of the sequence tag coverage for chromosome 21 in and the sequence tag coverage for chromosome 14 each determined in the test sample. Similarly, chromosome doses for chromosomes 13, 18, X, Y, and other chromosomes associated with chromosomal aneuploidies are determined. A normalizing sequence for a chromosome of interest can be one or a group of chromosomes, or one or a group of chromosome segments. As described previously, a sequence of interest can be part of a chromosome, e.g., a chromosome segment. Accordingly, the dose for a chromosome segment can be determined as the ratio of the sequence tag coverage determined for the segment in the test sample and the sequence tag coverage for the normalizing chromosome segment in the test sample, wherein the normalizing segment in the test sample corresponds to the normalizing segment (single or a group of segments) identified in the qualified samples for the particular segment of interest. Chromosome segments can range from kilobases (kb) to megabases (Mb) in size (e.g., about 1 kb to 10 kb, or about 10 kb to 100 kb, or about 100 kb to 1 Mb).

In step 155, threshold values are derived from standard deviation values established for qualified sequence doses determined in a plurality of qualified samples and sequence doses determined for samples known to be aneuploid for a sequence of interest. Note that this operation is typically performed asynchronously with analysis of patient test samples. It may be performed, for example, concurrently with the selection of normalizing sequences from qualified samples. Accurate classification depends on the differences between probability distributions for the different classes, i.e., type of aneuploidy. In some examples, thresholds are chosen from empirical distribution for each type of aneuploidy, e.g., trisomy 21. Possible threshold values that were established for classifying trisomy 13, trisomy 18, trisomy 21, and monosomy X aneuploidies as described in the Examples, which describe the use of the method for determining chromosomal aneuploidies by sequencing cfDNA extracted from a maternal sample comprising a mixture of fetal and maternal nucleic acids. The threshold value that is determined to distinguish samples affected for an aneuploidy of a chromosome can be the same or can be different from the threshold for a different aneuploidy. As is shown in the Examples, the threshold value for each chromosome of interest is determined from the variability in the dose of the chromosome of interest across samples and sequencing runs. The less variable the chromosome dose for any chromosome of interest, the narrower the spread in the dose for the chromosome of interest across all the unaffected samples, which are used to set the threshold for determining different aneuploidies.

Returning to the process flow associated with classifying a patient test sample, in step 160, the copy number variation of the sequence of interest is determined in the test sample by comparing the test sequence dose for the sequence of interest to at least one threshold value established from the qualified sequence doses. This operation may be performed by the same computational apparatus employed to measure sequence tag coverages and/or calculate segment doses.

In step 160, the calculated dose for a test sequence of interest is compared to that set as the threshold values that are chosen according to a user-defined "threshold of reliability" to classify the sample as a "normal" an "affected" or a "no call." The "no call" samples are samples for which a definitive diagnosis cannot be made with reliability. Each type of affected sample (e.g., trisomy 21, partial trisomy 21, monosomy X) has its own thresholds, one for calling normal (unaffected) samples and another for calling affected samples (although in some cases the two thresholds coincide). As described elsewhere herein, under some circumstances a no-call can be converted to a call (affected or normal) if fetal fraction of nucleic acid in the test sample is sufficiently high. The classification of the test sequence may be reported by the computational apparatus employed in other operations of this process flow. In some cases, the classification is reported in an electronic format and may be displayed, emailed, texted, etc. to interest persons.

In some embodiments, the determination of CNV comprises calculating a NCV or NSV that relates the chromosome or segment dose to the mean of the corresponding chromosome or segment dose in a set of qualified samples as described above. Then CNV can be determined by comparing the NCV/NSV to a predetermined copy number evaluation threshold value.

The copy number evaluation threshold can be chosen to optimize the rate of false positives and false negatives. The higher the copy number evaluation threshold, the less likely the occurrence of a false positive. Similarly, the lower the threshold, the less likely the occurrence of a false negative. Thus, a trade-off exists between a first ideal threshold above which only true positives are classified, and a second ideal threshold below which only true negatives are classified.

Thresholds are set largely depending on the variability in chromosome doses for a particular chromosome of interest as determined in a set of unaffected samples. The variability is dependent on a number of factors, including the fraction of fetal cDNA present in a sample. The variability (CV) is determined by the mean or median and standard deviation for chromosome doses across a population of unaffected samples. Thus, the threshold (s) for classifying aneuploidy use NCVs, according to:

$$NCV_{ij} = \frac{x_{ij} - \hat{\mu}_j}{\hat{\sigma}_j}$$

(where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.)

with an associated fetal fraction as:

$$FF_{ij} = 2 \times \left| \frac{NCV_{ij} \times \hat{\sigma}_j}{\hat{\mu}_j} \right| = 2 \times NCV \times CV$$

Thus, for every NCV of a chromosome of interest, an expected fetal fraction associated with the given NCV value can be calculated from the CV based on the mean and standard deviation of the chromosome ratio for the chromosome of interest across a population of unaffected samples.

Subsequently, based on the relationship between fetal fraction and NCV values, a decision boundary can be chosen above which samples are determined to be positive (affected) based on the normal distribution quantiles. As described above, in some embodiments, a threshold is set for optimal trade-off between the detection of true positives and rate of false negative results. Namely, the threshold is chosen to maximize the sum of true positives and true negatives, or minimize the sum of the false positives and false negatives.

Certain embodiments provide a method for providing prenatal diagnosis of a fetal chromosomal aneuploidy in a biological sample comprising fetal and maternal nucleic acid molecules. The diagnosis is made based on obtaining sequence information from at least a portion of the mixture of the fetal and maternal nucleic acid molecules derived from a biological test sample, e.g., a maternal plasma sample, computing from the sequencing data a normalizing chromosome dose for one or more chromosomes of interest, and/or a normalizing segment dose for one or more segments of interest, and determining a statistically significant difference between the chromosome dose for the chromosome of interest and/or the segment dose for the segment of interest, respectively, in the test sample and a threshold value established in a plurality of qualified (normal) samples, and providing the prenatal diagnosis based on the statistical difference. As described in step 160 of the method, a diagnosis of normal or affected is made. A "no call" is provided in the event that the diagnosis for normal or affected cannot be made with confidence.

In some embodiments, two thresholds can be chosen. A first threshold is chosen to minimize the false positive rate, above which samples will be classified as "Affected", and a second threshold is chosen to minimize the false negative rate, below which samples will be classified as "unaffected". Samples having NCVs above the second threshold but below the first threshold can be classified as "Aneuploidy suspected" or "No call" samples, for which the presence or absence of aneuploidy can be confirmed by independent means. The region between the first and second thresholds can be referred to as a "no call" region.

In some embodiments, the suspected and no call thresholds are shown in Table 1. As can be seen, the thresholds of NCV vary across different chromosomes. In some embodiments, the thresholds vary according to the FF for the sample as explained above. Threshold techniques applied here contribute to improved sensitivity and selectivity in some embodiments.

TABLE 1

Suspected and Affected NCV Thresholds Bracketing No-Call Ranges

|  | Suspected | Affected |
| --- | --- | --- |
| Chr 13 | 3.5 | 4.0 |
| Chr 18 | 3.5 | 4.5 |
| Chr 21 | 3.5 | 4.0 |
| Chr X (XO, XXX) | 4.0 | 4.0 |
| Chr Y (XX vs XY) | 6.0 | 6.0 |

Figure 16A:
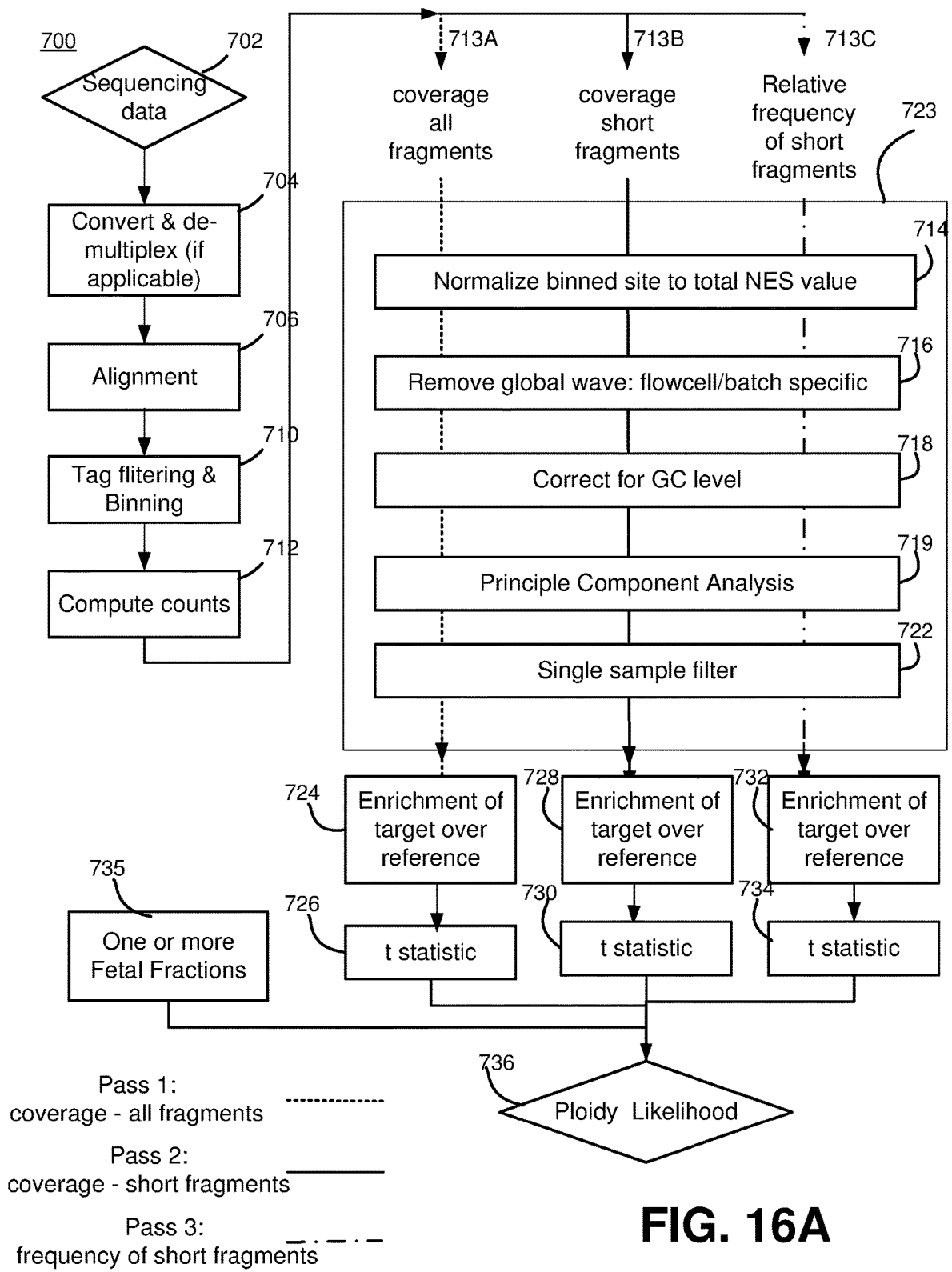
FIG. 16A shows a flow chart of a three-pass process for evaluating copy number.

Copy Number Determination Using a Three-Pass Process, Likelihood Ratios, T Statistics, and/or Fetal Fractions
Three-Pass Process FIG. 16A shows a flow chart of a three-pass process for evaluating copy number. It includes three overlapping passes of work flow 700, which includes pass 1 (or 713A) analysis of coverage of reads associated with fragments of all sizes, pass 2 (or 713B) analysis of coverage of reads associated with shorter fragments, and pass 3 (or 713C) analysis of relative frequency of shorter reads relative to all reads.

Process 700 is similar to process 600 in its overall organization. Operations indicated by blocks 702, 704, 706, 710, 712 may be performed in the same or a similar manner to operations indicated by blocks 602, 604, 606, and 610, and 612. After read counts are obtained, coverage is determined using reads from fragments of all sizes in pass 713A. Coverage is determined using reads from short fragments in pass 713B. Frequency of reads from short fragments relative to all reads is determined in pass 713C. The relative frequency is also referred to as a size ratio or a size fraction elsewhere herein. It is an example of a fragment size characteristic. In some implementations, short fragments are fragments shorter than about 150 base pairs. In various implementations, short fragments can be in the size ranges of about 50-150, 80-150, or 110-150 base pairs. In some implementations, the third pass, or pass 713C, is optional.

The data of the three passes 713A, 713B, and 713C all undergo normalization operations 714, 716, 718, 719, and 722 to remove variance unrelated to copy number of the sequence of interest. These normalization operations are boxed in blocks 723. Operation 714 involves normalizing the analyzed quantity of the sequence of interest by dividing the analyzed quantity by the total value of the quantity of the reference sequence. This normalization step uses values obtained from a test sample. Similarly, operations 718 and 722 normalize the analyzed quantity using values obtained from the test sample. Operations 716 and 719 use values obtained from a training set of unaffected samples.

Operation 716 removes variance of a global wave obtained from the training set of unaffected samples, which uses the same or similar methods as described with reference to block 616. Operation 718 removes variance of individual-specific GC variance using the same or similar manner methods as described with reference to block 618.

Operation 719 removes further variance using a principal component analysis (PCA) method. The variance removed by the PCA methods is due to factors unrelated to copy number of the sequence of interest. The analyzed quantity in each bin (coverage, fragment size ratio, etc.) provides an independent variable for the PCA, and the samples of the unaffected training set supply values for these independent variables. The samples of the training set all include samples having the same copy number of the sequence of interest, e.g., two copies of a somatic chromosome, one copy of the X chromosome (when male samples are used as unaffected samples), or two copies of the X chromosome (when female samples are used as unaffected samples). Thus, variance in the samples does not result from an aneuploidy or other difference in copy number. The PCA of the training set yields principal components that are unrelated to copy number of the sequence of interest. The principal components can then be used to remove variance in a test sample unrelated to the copy number of the sequence of interest.

In certain embodiments, the variance of one or more of the principal components is removed from the test sample's data using the coefficients estimated from unaffected samples' data in a region outside of the sequence of interest. In some implementations, the region represents all robust chromosomes. For instance, a PCA is performed on normalized bin coverage data of training normal samples, thereby providing principal components corresponding to dimensions in which most variance in the data can be captured. Variance so captured is unrelated to copy number variation in the sequence of interest. After the principal components have been obtained from the training normal samples, they are applied to test data. A linear regression model with test sample as response variable and principal components as dependent variables is generated across bins from a region outside of the sequence of interest. Resulting regression coefficients are used to normalize the bin coverage of the region of interest by subtracting the linear combination of principal components defined by the estimated regression coefficients. This removes variance unrelated to CNV from the sequence of interest. See block 719. The residual data is used for downstream analysis. Additionally, operation 722 removes outlier data points using methods described with reference to block 622.

After undergoing the normalization operations in block 723, the coverage values of all bins have been "normalized" to remove sources of variation other than aneuploidy or other copy number variations. In a sense, the bins of the sequence of interest are enriched or altered relative to other bins for purposes of copy number variation detection. See block 724, which is not an operation but represents the resulting coverage values. The normalization operations in large block 723 may increase the signal and/or reduce the noise of the quantity under analysis. Similarly, the coverage values of short fragments for the bins have been normalized to remove sources of variation other than aneuploidy or other copy number variations as shown in block 728, and the relative frequency of short fragments (or size ratio) for the bins have been similarly normalized to remove sources of variation other than aneuploidy or other copy number variations as shown in block 732. As with block 724, blocks 728 and 732 are not operations but represents the coverage and relative frequency values after the processing large block 723. It should be understood, that the operations in large block 723 may be modified, rearranged, or removed. For example, in some embodiments, PCA operation 719 is not performed. In other embodiments, the correcting for GC operation 718 is not performed. In other embodiments, the order of the operations is changed; e.g., PCA operation 719 is performed prior to correct for GC operation 718, The coverage of all fragments after normalization and variance removal shown in block 724 is used to obtain a t-statistic in block 726. Similarly, the coverage of short fragments after normalization and variance removal shown in block 728 is used to obtain a t-statistic in block 730, and the relative frequency of short fragments after normalization and variance removal shown in block 732 is used to obtain a t-statistic in block 734.

Applying a t-statistic to copy number analysis can help to improve the accuracy of the analysis. Using only the mean to distinguish the two distributions does not capture the difference between the two distributions as well as using both mean and variance. A t-statistic can reflect both the mean and variance of the distribution.

In some implementations, operation 726 calculates a t-statistic as follows:

$$t = \frac{\overline{x_1} - \overline{x_2}}{\sqrt{\frac{s_1^2}{n_1} + \frac{s_2^2}{n_2}}}$$

where $x_1$ is the bin coverage of the sequence of interest, $x_2$ being the bin coverage of the reference region/sequence, $s_1$ being the standard deviation of the coverages of the sequence of interest, $s_2$ being the standard deviation of the coverages of the reference region, $n_1$ being the number of bins of the sequence of interest; and $n_2$ being the number of the bins of the reference region.

In some implementations, the reference region includes all robust chromosomes (e.g., chromosomes other than those most likely to harbor an aneuploidy). In some implementations, the reference region includes at least one chromosome outside of the sequence of interest. In some imitations, the reference region includes robust chromosomes not including the sequence of interest. In other implementations, the reference region includes a set of chromosomes (e.g., a subset of chromosomes selected from the robust chromosomes) that have been determined to provide the best signal detection ability for a set of training samples. In some embodiments, the signal detection ability is based on the ability of the reference region to discriminate bins harboring copy number variations from bins that do not harbor copy number variations. In some embodiments, the reference region is identified in a manner similar to that employed to determine a "normalizing sequence" or a "normalizing chromosome" as described in the section titled "Identification of Normalizing Sequences."

Determination of Fetal Fraction

Returning to FIG. 16A, one or more fetal fraction estimates (block 735) may be combined with any of the t statistics in block 726, 730 and 734 to obtain a likelihood estimate for a ploidy case. See block 736. In some implementations, the one or more fetal fractions of block 740 are obtained by any of process 800 in FIG. 16B, process 900 in FIG. 16C, or process 1000 of FIG. 16D. The processes may be implemented in parallel using a workflow as workflow 1100 in FIG. 2J.

Figure 16B:
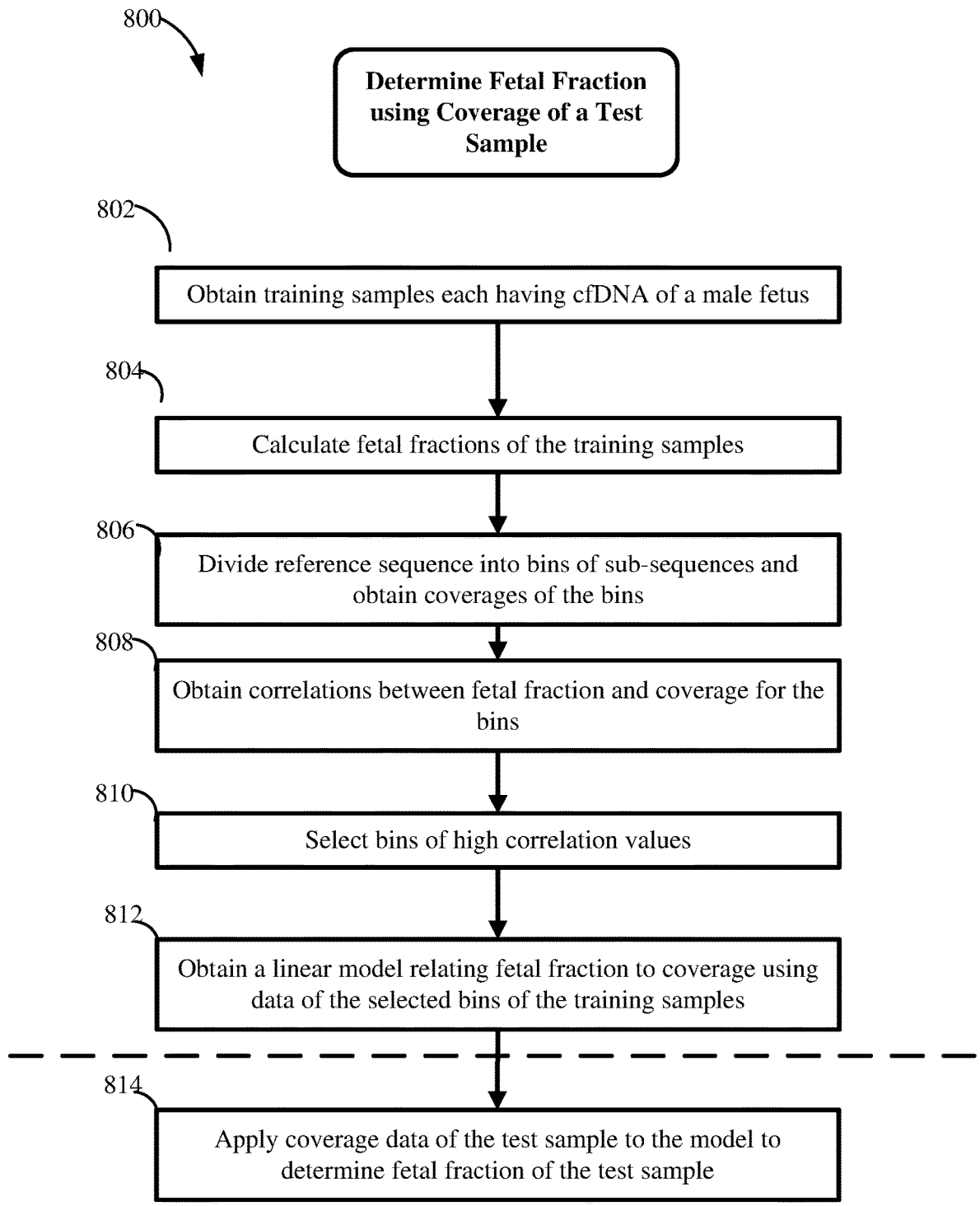
FIG. 16B shows an example process 800 for determining fetal fraction from coverage information according to some implementations of the disclosure.

FIG. 16B shows an example process 800 for determining fetal fraction from coverage information according to some implementations of the disclosure. Process 800 starts by obtaining coverage information (e.g., sequence dose values) of training samples from a training set. See block 802. Each sample of the training set is obtained from a pregnant woman known to be carrying a male fetus. Namely, the sample contains cfDNA of the male fetus. In some implementations, operation 802 may obtain sequence coverage normalized in ways different from sequence dose as described herein, or it may obtain other coverage values.

Process 800 then involves calculating fetal fractions of the training samples. In some implementations, fetal fraction may be calculated from the sequence dose values:

$$FF_j = -2 \times \frac{Rx_j - \text{median}(Rx_i)}{\text{median}(Rx_i)}$$

where $Rx_j$ is the sequence dose for a male sample, median($Rx_i$) being the median of the sequence doses for female samples. In other implementations, mean or other central tendency measures may be used. In some implementations, the FF may be obtained by other methods, such as the relative frequency of X and Y chromosomes. See block 804.

Process 800 further involves dividing the reference sequence into multiple bins of subsequences. In some implementations, the reference sequence is a complete genome. In some implementations, the bins are 100 kb bins. In some implementations, the genome is divided into about 25,000 bins. The process then obtains coverages of the bins. See block 806. In some implementations, the coverages used in block 806 are obtained after undergoing normalizing operations shown in block 1123 of FIG. 2J. In other implementations, coverages from different size range may be used.

Each bin is associated with coverages of the samples in the training set. Therefore, for each bin a correlation may be obtained between the coverage of the samples and the fetal fractions of the samples. Process 800 involves obtaining correlations between fetal fraction and coverage for all the bins. See block 808. Then the process selects the bins having correlation values above a threshold. See block 810. In some implementations, bins having the 6000 highest correlation values are selected. The purpose is to identify bins that demonstrate high correlation between coverage and fetal fraction in the training samples. Then the bins may be used to predict fetal fraction in the test sample. Although the training samples are male samples, the correlation between fetal fraction and coverage may be generalized to male and female test samples.

Using the selected bins having high correlation values, the process obtains a linear model relating fetal fraction to coverage. See block 812. Each selected bin provides an independent variable for the linear model. Therefore, the obtained linear model also includes a parameter or weight for each bin. The weights of the bins are adjusted to fit the model to the data. After obtaining the linear model, process 800 involves applying coverage data of the test sample to the model to determine the fetal fraction for the test sample. See block 814. The applied coverage data of the test sample are for the bins that have high correlations between fetal fraction and coverage.

FIG. 2J shows workflow 1100 for processing sequence reads information of which can be used to obtain fetal fraction estimates. The workflow 1100 shares similar processing steps as workflow 600 in FIG. 2D. Blocks 1102, 1104, 1106, 1110, 1112, 1123, 1114, 1116, 1118, and 1122 respectively correspond to blocks 602, 604, 606, 610, 612, 623, 614, 616, 618, and 622. In some implementations, one or more normalizing operations in the 123 block are optional. Pass 1 provides coverage information, which may be used in block 806 of process 800 shown in FIG. 16B. Process 800 then can yield a fetal fraction estimate 1150 in FIG. 2J.

In some implementations, a plurality of fetal fraction estimates (e.g., 1150 and 1152 in FIG. 2J) may be combined to provide a composite fetal fraction estimate (e.g., 1154). Various methods may be used to obtain fetal fraction estimates. For instance, fetal fraction may be obtained from coverage information. See block 1150 of FIG. 2J and process 800 of FIG. 16B. In some implementations, fetal fraction can also be estimated from size distribution of fragments. See block 1152 of FIG. 2J and process 900 of FIG. 16C. In some implementations, fetal fraction can also be estimated from 8-mer frequency distribution. See block 1152 of FIG. 2J and process 1000 of FIG. 16D.

In a test sample including cfDNA of male fetus, fetal fraction may also be estimated from the coverage of the Y chromosome and/or the X chromosome. In some implementations, a composite estimate of fetal fraction (see, e.g., block 1155) for a putatively male fetus is obtained by using information selected from the group consisting of: a fetal fraction obtained from coverage information of bins, a fetal fraction obtained from fragment size information, a fetal fraction obtained from coverage of the Y chromosome, a fetal fraction obtained from the X chromosome, and any combinations thereof. In some implementations, the putative sex of the fetus is obtained by using the coverage of the Y chromosome. Two or more fetal fractions (e.g., 1150 and 1152) may be combined in various ways to provide a composite estimate of fetal fraction (e.g., 1155). For instance, an average or a weighted average approach may be used in some implementations, wherein weighting can be based on the statistical confidence of the fetal fraction estimate.

In some implementations, a composite estimate of fetal fraction for a putatively female fetus is obtained by using information selected from the group consisting of: a fetal fraction obtained from coverage information of bins, a fetal fraction obtained from fragment size information, and any combinations thereof.

Figure 16C:
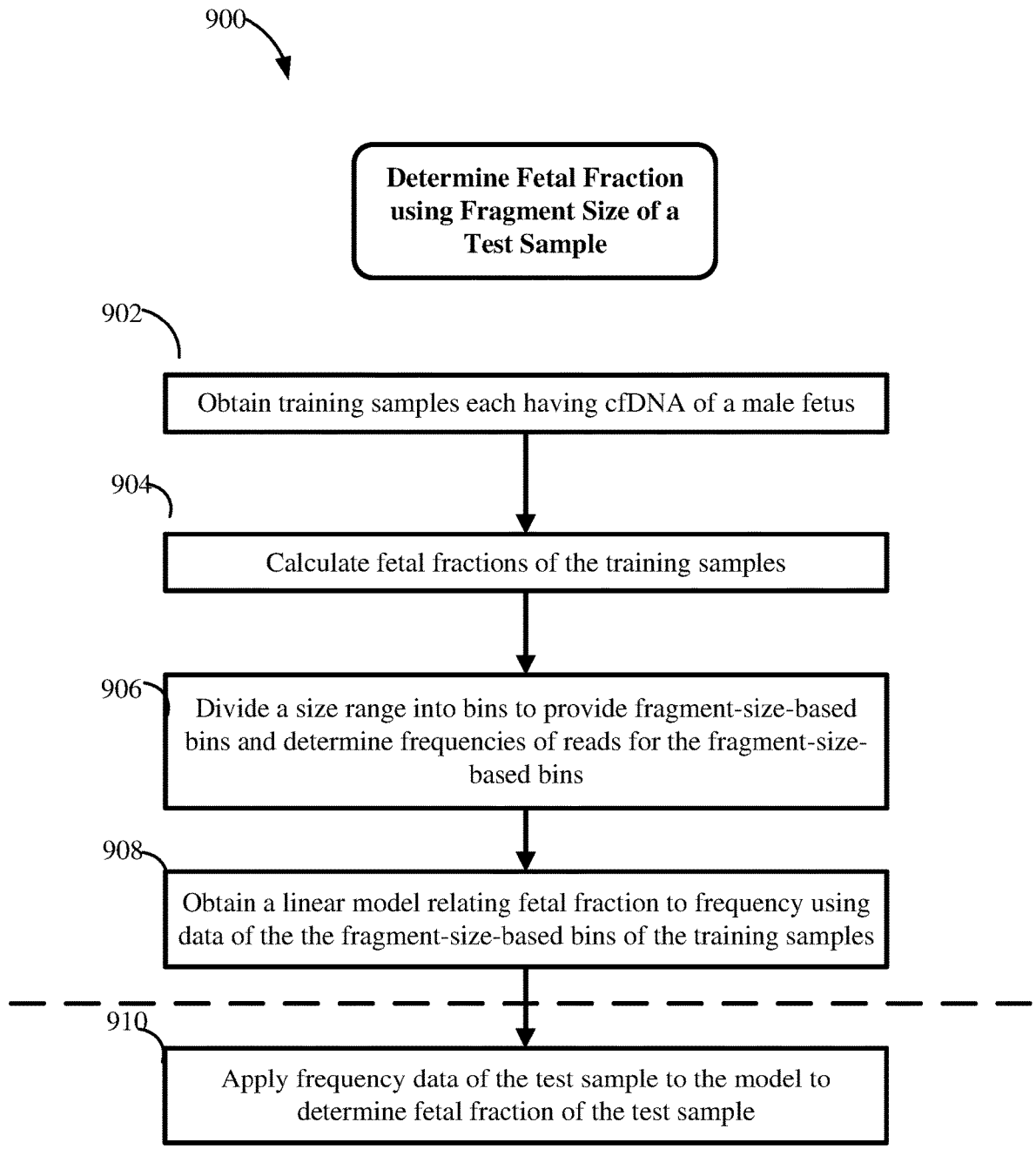
FIG. 16C shows a process for determining fetal fraction from size distribution information according to some implementations.

FIG. 16C shows a process for determining fetal fraction from size distribution information according to some implementations. Process 900 starts by obtaining coverage information (e.g., sequence dose values) of male training samples from a training set. See block 902. Process 900 then involves calculating fetal fractions of the training samples using methods described above with reference to block 804. See block 904.

Process 900 proceeds to divide a size range into a plurality of bins to provide fragment-size-based bins and determine frequencies of reads for the fragment-size-based bins. See block 906. In some implementations, the frequencies of fragment-size-based bins are obtained without normalizing for factors shown in block 1123. See path 1124 of FIG. 2J. In some implementations, the frequencies of fragment-size-based bins are obtained after optionally undergoing normalizing operations shown in block 1123 of FIG. 2J. In some implementations, the size range is divided into 40 bins. In some implementations, the bin at the low end includes fragments of size smaller than about 55 base pairs. In some implementations, the bin at the low end includes fragments of size in the range of about 50-55 base pairs, which excludes information for reads shorter than 50 bp. In some implementations, the bin at the high end includes fragments of size larger than about 245 base pairs. In some implementations, the bin at the high end includes fragments of size in the range of about 245-250 base pairs, which excludes information for reads longer than 250 bp.

Process 900 proceeds by obtaining a linear model relating fetal fraction to frequencies of reads for the fragment-size-based bins, using data of the training samples. See block 908. The obtained linear model includes independent variables for the frequencies of reads of the size-based bins. The model also includes a parameter or weight for each size-based bin. The weights of the bins are adjusted to fit the model to the data. After obtaining the linear model, process 900 involves applying read frequency data of the test sample to the model to determine the fetal fraction for the test sample. See block 910.

Figure 16D:
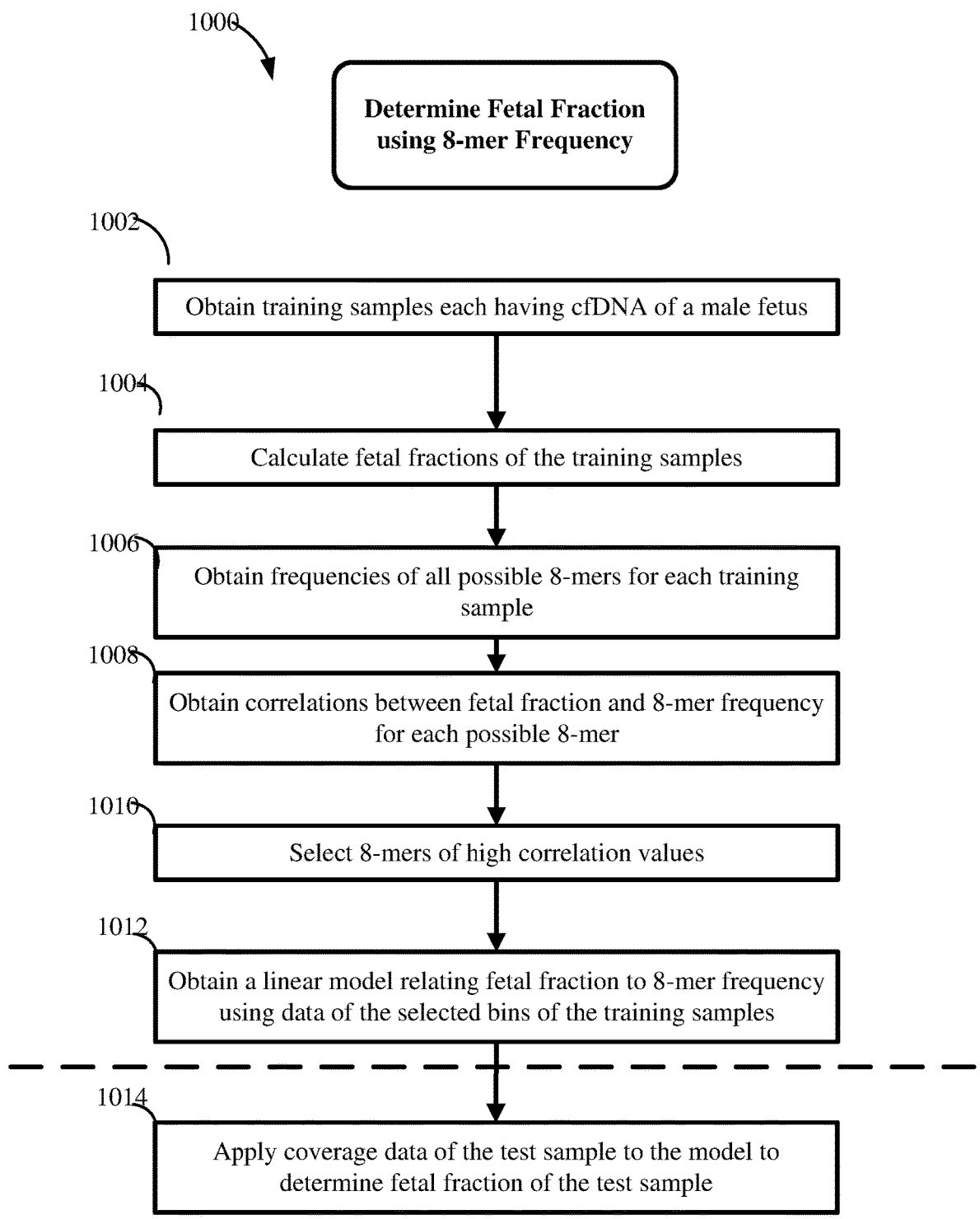
FIG. 16D shows an example process 1000 for determining fetal fraction from 8-mer frequency information according to some implementations of the disclosure.

In some implementations, an 8-mer frequency may be used to calculate fetal fraction. FIG. 16D shows an example process 1000 for determining fetal fraction from 8-mer frequency information according to some implementations of the disclosure. Process 1000 starts by obtaining coverage information (e.g., sequence dose values) of male training samples from a training set. See block 1002. Process 1000 then involves calculating fetal fractions of the training samples using any of the methods described for block 804. See block 1004.

Process 1000 further involves obtaining the frequencies of 8-mers (e.g., all possible permutations of 4 nucleotides at 8 positions) from the reads of each training sample. See block 1006. In some implementations, up to 65,536 or close to that many 8-mers and their frequencies are obtained. In some implementations, the frequencies of 8-mers are obtained without normalizing for factors shown in block 1123. In some implementations, 8-mer frequencies are obtained after optionally undergoing normalizing operations.

Each 8-mer is associated with frequencies of the samples in the training set. Therefore, for each 8-mer a correlation may be obtained between the 8-mer frequency of the samples and the fetal fractions of the samples. Process 1000 involves obtaining correlations between fetal fraction and 8-mer frequencies for all the 8-mers. See block 1008. Then the process selects the 8-mers having correlation values above a threshold. See block 1010. The purpose is to identify 8-mers that demonstrate high correlation between 8-mer frequency and fetal fraction in the training samples. Then the bins may be used to predict fetal fraction in the test sample. Although the training samples are male samples, the correlation between fetal fraction and 8-mer frequency may be generalized to male and female test samples.

Using the selected 8-mers having high correlation values, the process obtains a linear model relating fetal fraction to 8-mer frequency. See block 1012. Each selected bin provides an independent variable for the linear model. Therefore, the obtained linear model also includes a parameter or weight for each bin. After obtaining the linear model, process 1000 involves applying 8-mer frequency data of the test sample to the model to determine the fetal fraction for the test sample. See block 1014.

In some implementations, coverages (or other parameters) having correlation with different portions of a genome are weighted for the different portions in calculating fetal fraction. Examples of such methods include the SeqFF method described in U.S. Patent Application Publication No. US 2015/0005176, and Kim et al. (2015), Prenatal Diagnosis, 35, 1-6, which are incorporated by reference in their entireties for the purpose of calculating fetal fraction. In some implementations, bins having higher fractions of fetal cell-free nucleic acid fragments are weighted more heavily for determining fetal fractions.

Determining Likelihood Ratio

Returning to FIG. 16A, in some implementations, process 700 involves obtaining a final ploidy likelihood in operation 736 using the t-statistic based on the coverage of all fragments provided by operation 726, the fetal fraction estimate provided by operation 726, and the t-statistic based on the coverage of the short fragments provided by operation 730. These implementations combine the results from pass 1 and pass 2 using a multivariate normal models. In some implementations for evaluating CNV, the ploidy likelihood is an aneuploidy likelihood, which is a likelihood of a model having an aneuploid assumption (e.g., trisomy or monosomy) minus the likelihood of a model having an euploid assumption wherein the model uses the t-statistic based on the coverage of all fragments, the fetal fraction estimate, and the t-statistic based on the coverage of the short fragments as an input and provides a likelihood as an output.

In some implementations, the ploidy likelihood is expressed as a likelihood ratio. In some implementations, likelihood ratio is modeled as:

$$LR = \frac{\sum_{ff_{total}} q(ff_{total}) * p_1(T_{short}, T_{all} | ff_{est})}{p_0(T_{short}, T_{all})}$$

where $p_i$ represents the likelihood that data come from a multivariate normal distribution representing a 3-copy or 1-copy model, $p_0$ represents the likelihood that data come from a multivariate normal distribution representing a 2-copy model, $T_{short}$, $T_{all}$ are T scores calculated from chromosomal coverage generated from short and all fragments, while $q(ff_{total})$ being the density distribution of fetal fraction (estimated from training data) considering the error associated with fetal fraction estimation. The model combine coverage generated from short fragments with coverage generated by all fragments, which helps improving separation between coverage scores of affected and unaffected samples. In the depicted embodiment, the model also makes use of fetal fraction, thereby further improves the ability to discriminate between affected and unaffected samples. Here, the likelihood ratio is calculated using t-statistic based on coverage of all fragments (726), t-statistic based on coverage of short fragments (730), and a fetal fraction estimate provided by processes 800 (or block 726), 900, or 1000 as described above. In some implementations, this likelihood ratio is used to analyze chromosomes 13, 18, and 21.

In some implementation, a ploidy likelihood obtained by operation 736 uses only the t-statistics obtained based on relative frequency of short fragments provided by operation 734 of pass 3 and the fetal fraction estimate provided by operation 726, processes 800, 900, or 1000. The likelihood ratio may be calculated according to the following equation:

$$LR = \frac{\sum_{ff_{total}} q(ff_{total}) * p_1(T_{short\_freq} | ff_{est})}{p_0(T_{short\_freq})}$$

where $p_i$ represents the likelihood that data come from a multivariate normal distribution representing a 3-copy or 1-copy model, $p_0$ represents the likelihood that data come from a multivariate normal distribution representing a 2-copy model, $T_{short\_freq}$ is a T score calculated from relative frequency of short fragments, while $q(ff_{total})$ being the density distribution of fetal fraction (estimated from training data) considering the error associated with fetal fraction estimation. Here, the likelihood ratio is calculated using t-statistic based on relative frequency of short fragments (734) and a fetal fraction estimate provided by processes 800 (or block 726), 900, or 1000 as described above. In some implementations, this likelihood ratio is used to analyze chromosome X.

In some implementations, the likelihood ratio is calculated using t-statistic based on coverage of all fragments (726), t-statistic based on coverage of short fragments (730), and relative frequency of short fragments (734). Moreover, fetal fraction obtained as describe above may be combined with t-statistics to calculate likelihood ration. By combining information from any of the three passes 713A, 713B, and 713C, the discriminative ability of the ploidy evaluation can be improved. In some implementations, different combinations may be used to obtain likelihood ratios for a chromosome, e.g., t statistics from all three passes, t statistics from the first and second passes, fetal fraction and three t-statistics, fetal fraction and one t statistic, etc. Then an optimal combination can be selected based on the models performance.

In various implementations explained above, the euploid model and aneuploidy model take t-statistics as input. However, of course they can also take raw or otherwise transformed coverage or abundance value as input, and provide likelihood as outputs. The otherwise transformed or t-statistics input can help to improve predictive ability of the models, but the transformation is not necessary in all implementations.

In some implementations for evaluating autosomes, the modeled likelihood ratio represents the likelihood of the modeled data having been obtained from a trisomy or monosomy sample relative to the likelihood of the modeled data having been obtained from a diploid sample. Such likelihood ratio may be used to determine trisomy or monosomy of the autosomes in some implementations.

In some implementations for evaluating the sex chromosome, the likelihood ratio for monosomy X and the likelihood ratio for trisomy X are evaluated. Moreover, a chromosome coverage measurement (e.g., CNV or coverage z score) for chromosome X and one for chromosome Y are also evaluated. In some implementations, the four values are evaluated using a decision tree to determine copy number of the sex chromosome. In some implementations, the decision tree allows determination of a ploidy case of XX, XY, X, XXY, XXX, or XYY.

In some implementations, the likelihood ratio is transformed into a log likelihood ratio, and a criterion or threshold for calling an aneuploidy or a copy number variation can be empirically set to obtain a particular sensitivity and selectivity. For instance, a log likelihood ratio of 1.5 may be set for calling a trisomy 13 or a trisomy 18 based on a model's sensitivity and selectivity when applied to a training set. Moreover, for instance, a call criterion value of 3 may be set for a trisomy of chromosome 21 in some applications.

Samples and Sample Processing
Samples

Samples that are used for determining a CNV, e.g., chromosomal aneuploidies, partial aneuploidies, and the like, can include samples taken from any cell, tissue, or organ in which copy number variations for one or more sequences of interest are to be determined. Desirably, the samples contain nucleic acids that are that are present in cells and/or nucleic acids that are "cell-free" (e.g., cfDNA).

In some embodiments it is advantageous to obtain cell-free nucleic acids, e.g., cell-free DNA (cfDNA). Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, IN, Qiagen, Valencia, CA, Macherey-Nagel, Duren, DE). Biological samples comprising cfDNA have been used in assays to determine the presence or absence of chromosomal abnormalities, e.g., trisomy 21, by sequencing assays that can detect chromosomal aneuploidies and/or various polymorphisms.

In various embodiments the cfDNA present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a cfDNA sequencing library. Non-specific enrichment can be the selective enrichment of one of the two genomes present in a sample that comprises more than one genome. For example, non-specific enrichment can be selective of the fetal genome in a maternal sample, which can be obtained by known methods to increase the relative proportion of fetal to maternal DNA in a sample. Alternatively, non-specific enrichment can be the non-selective amplification of both genomes present in the sample. For example, non-specific amplification can be of fetal and maternal DNA in a sample comprising a mixture of DNA from the fetal and maternal genomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample comprising the mixture of cfDNA from different genomes is un-enriched for cfDNA of the genomes present in the mixture. In other embodiments, the sample comprising the mixture of cfDNA from different genomes is non-specifically enriched for any one of the genomes present in the sample.

The sample comprising the nucleic acid(s) to which the methods described herein are applied typically comprises a biological sample ("test sample"), e.g., as described above. In some embodiments, the nucleic acid(s) to be screened for one or more CNVs is purified or isolated by any of a number of well-known methods.

Accordingly, in certain embodiments the sample comprises or consists of a purified or isolated polynucleotide, or it can comprise samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In another illustrative, but non-limiting embodiment, the maternal sample is a mixture of two or more biological samples, e.g., the biological sample can comprise two or more of a biological fluid sample, a tissue sample, and a cell culture sample. In some embodiments, the sample is a sample that is easily obtainable by non-invasive procedures, e.g., blood, plasma, serum, sweat, tears, sputum, urine, milk, sputum, ear flow, saliva and feces. In some embodiments, the biological sample is a peripheral blood sample, and/or the plasma and serum fractions thereof. In other embodiments, the biological sample is a swab or smear, a biopsy specimen, or a sample of a cell culture. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation.

Sequencing Library Preparation

In one embodiment, the methods described herein can utilize next generation sequencing technologies (NGS), that allow multiple samples to be sequenced individually as genomic molecules (i.e., singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Marker Nucleic Acids for Tracking and Verifying Sample Integrity

In various embodiments verification of the integrity of the samples and sample tracking can be accomplished by sequencing mixtures of sample genomic nucleic acids, e.g., cfDNA, and accompanying marker nucleic acids that have been introduced into the samples, e.g., prior to processing.

Marker nucleic acids can be combined with the test sample (e.g., biological source sample) and subjected to processes that include, for example, one or more of the steps of fractionating the biological source sample, e.g., obtaining an essentially cell-free plasma fraction from a whole blood sample, purifying nucleic acids from a fractionated, e.g., plasma, or unfractionated biological source sample, e.g., a tissue sample, and sequencing. In some embodiments, sequencing comprises preparing a sequencing library. The sequence or combination of sequences of the marker molecules that are combined with a source sample is chosen to be unique to the source sample. In some embodiments, the unique marker molecules in a sample all have the same sequence. In other embodiments, the unique marker molecules in a sample are a plurality of sequences, e.g., a combination of two, three, four, five, six, seven, eight, nine, ten, fifteen, twenty, or more different sequences.

In one embodiment, the integrity of a sample can be verified using a plurality of marker nucleic acid molecules having identical sequences. Alternatively, the identity of a sample can be verified using a plurality of marker nucleic acid molecules that have at least two, at least three, at least four, at least five, at least six, at least seven, at least eight, at least nine, at least ten, at least 11, at least 12, at least 13, at least 14, at least 15, at least 16, at least 17 m, at least 18, at least 19, at least 20, at least 25, at least 30, at least 35, at least 40, at least 50, or more different sequences. Verification of the integrity of the plurality of biological samples, i.e., two or more biological samples, requires that each of the two or more samples be marked with marker nucleic acids that have sequences that are unique to each of the plurality of test sample that is being marked. For example, a first sample can be marked with a marker nucleic acid having sequence A, and a second sample can be marked with a marker nucleic acid having sequence B. Alternatively, a first sample can be marked with marker nucleic acid molecules all having sequence A, and a second sample can be marked with a mixture of sequences B and C, wherein sequences A, B and C are marker molecules having different sequences.

The marker nucleic acid(s) can be added to the sample at any stage of sample preparation that occurs prior to library preparation (if libraries are to be prepared) and sequencing. In one embodiment, marker molecules can be combined with an unprocessed source sample. For example, the marker nucleic acid can be provided in a collection tube that is used to collect a blood sample. Alternatively, the marker nucleic acids can be added to the blood sample following the blood draw. In one embodiment, the marker nucleic acid is added to the vessel that is used to collect a biological fluid sample, e.g., the marker nucleic acid(s) are added to a blood collection tube that is used to collect a blood sample. In another embodiment, the marker nucleic acid(s) are added to a fraction of the biological fluid sample. For example, the marker nucleic acid is added to the plasma and/or serum fraction of a blood sample, e.g., a maternal plasma sample. In yet another embodiment, the marker molecules are added to a purified sample, e.g., a sample of nucleic acids that have been purified from a biological sample. For example, the marker nucleic acid is added to a sample of purified maternal and fetal cfDNA. Similarly, the marker nucleic acids can be added to a biopsy specimen prior to processing the specimen. In some embodiments, the marker nucleic acids can be combined with a carrier that delivers the marker molecules into the cells of the biological sample. Cell-delivery carriers include pH-sensitive and cationic liposomes.

In various embodiments, the marker molecules have antigenomic sequences, that are sequences that are absent from the genome of the biological source sample. In an exemplary embodiment, the marker molecules that are used to verify the integrity of a human biological source sample have sequences that are absent from the human genome. In an alternative embodiment, the marker molecules have sequences that are absent from the source sample and from any one or more other known genomes. For example, the marker molecules that are used to verify the integrity of a human biological source sample have sequences that are absent from the human genome and from the mouse genome. The alternative allows for verifying the integrity of a test sample that comprises two or more genomes. For example, the integrity of a human cell-free DNA sample obtained from a subject affected by a pathogen, e.g., a bacterium, can be verified using marker molecules having sequences that are absent from both the human genome and the genome of the affecting bacterium. Sequences of genomes of numerous pathogens, e.g., bacteria, viruses, yeasts, fungi, protozoa etc., are publicly available on the World Wide Web at ncbi.nlm.nih.gov/genomes. In another embodiment, marker molecules are nucleic acids that have sequences that are absent from any known genome. The sequences of marker molecules can be randomly generated algorithmically.

In various embodiments the marker molecules can be naturally-occurring deoxyribonucleic acids (DNA), ribonucleic acids or artificial nucleic acid analogs (nucleic acid mimics) including peptide nucleic acids (PNA), morpholino nucleic acid, locked nucleic acids, glycol nucleic acids, and threose nucleic acids, which are distinguished from naturally-occurring DNA or RNA by changes to the backbone of the molecule or DNA mimics that do not have a phosphodiester backbone. The deoxyribonucleic acids can be from naturally-occurring genomes or can be generated in a laboratory through the use of enzymes or by solid phase chemical synthesis. Chemical methods can also be used to generate the DNA mimics that are not found in nature. Derivatives of DNA are that are available in which the phosphodiester linkage has been replaced but in which the deoxyribose is retained include but are not limited to DNA mimics having backbones formed by thioformacetal or a carboxamide linkage, which have been shown to be good structural DNA mimics Other DNA mimics include morpholino derivatives and the peptide nucleic acids (PNA), which contain an N-(2-aminoethyl)glycine-based pseudopeptide backbone (Ann Rev Biophys Biomol Struct 24:167-183 [1995]). PNA is an extremely good structural mimic of DNA (or of ribonucleic acid [RNA]), and PNA oligomers are able to form very stable duplex structures with Watson-Crick complementary DNA and RNA (or PNA) oligomers, and they can also bind to targets in duplex DNA by helix invasion (Mol Biotechnol 26:233-248 [2004]. Another good structural mimic/analog of DNA analog that can be used as a marker molecule is phosphorothioate DNA in which one of the non-bridging oxygens is replaced by a sulfur. This modification reduces the action of endo- and exonucleases2 including 5' to 3' and 3' to 5' DNA POL 1 exonuclease, nucleases S1 and P1, RNases, serum nucleases and snake venom phosphodiesterase.

The length of the marker molecules can be distinct or indistinct from that of the sample nucleic acids, i.e., the length of the marker molecules can be similar to that of the sample genomic molecules, or it can be greater or smaller than that of the sample genomic molecules. The length of the marker molecules is measured by the number of nucleotide or nucleotide analog bases that constitute the marker molecule. Marker molecules having lengths that differ from those of the sample genomic molecules can be distinguished from source nucleic acids using separation methods known in the art. For example, differences in the length of the marker and sample nucleic acid molecules can be determined by electrophoretic separation, e.g., capillary electrophoresis. Size differentiation can be advantageous for quantifying and assessing the quality of the marker and sample nucleic acids. Preferably, the marker nucleic acids are shorter than the genomic nucleic acids, and of sufficient length to exclude them from being mapped to the genome of the sample. For example, as a 30 base human sequence is needed to uniquely map it to a human genome. Accordingly in certain embodiments, marker molecules used in sequencing bioassays of human samples should be at least 30 bp in length.

The choice of length of the marker molecule is determined primarily by the sequencing technology that is used to verify the integrity of a source sample. The length of the sample genomic nucleic acids being sequenced can also be considered. For example, some sequencing technologies employ clonal amplification of polynucleotides, which can require that the genomic polynucleotides that are to be clonally amplified be of a minimum length. For example, sequencing using the Illumina GAII sequence analyzer includes an in vitro clonal amplification by bridge PCR (also known as cluster amplification) of polynucleotides that have a minimum length of 110 bp, to which adaptors are ligated to provide a nucleic acid of at least 200 bp and less than 600 bp that can be clonally amplified and sequenced. In some embodiments, the length of the adaptor-ligated marker molecule is between about 200 bp and about 600 bp, between about 250 bp and 550 bp, between about 300 bp and 500 bp, or between about 350 and 450. In other embodiments, the length of the adaptor-ligated marker molecule is about 200 bp. For example, when sequencing fetal cfDNA that is present in a maternal sample, the length of the marker molecule can be chosen to be similar to that of fetal cfDNA molecules. Thus, in one embodiment, the length of the marker molecule used in an assay that comprises massively parallel sequencing of cfDNA in a maternal sample to determine the presence or absence of a fetal chromosomal aneuploidy, can be about 150 bp, about 160 bp, 170 bp, about 180 bp, about 190 bp or about 200 bp; preferably, the marker molecule is about 170 pp. Other sequencing approaches, e.g., SOLiD sequencing, Polony Sequencing and 454 sequencing use emulsion PCR to clonally amplify DNA molecules for sequencing, and each technology dictates the minimum and the maximum length of the molecules that are to be amplified. The length of marker molecules to be sequenced as clonally amplified nucleic acids can be up to about 600 bp. In some embodiments, the length of marker molecules to be sequenced can be greater than 600 bp.

Single molecule sequencing technologies, that do not employ clonal amplification of molecules, and are capable of sequencing nucleic acids over a very broad range of template lengths, in most situations do not require that the molecules to be sequenced be of any specific length. However, the yield of sequences per unit mass is dependent on the number of 3' end hydroxyl groups, and thus having relatively short templates for sequencing is more efficient than having long templates. If starting with nucleic acids longer than 1000 nt, it is generally advisable to shear the nucleic acids to an average length of 100 to 200 nt so that more sequence information can be generated from the same mass of nucleic acids. Thus, the length of the marker molecule can range from tens of bases to thousands of bases. The length of marker molecules used for single molecule sequencing can be up to about 25 bp, up to about 50 bp, up to about 75 bp, up to about 100 bp, up to about 200 bp, up to about 300 bp, up to about 400 bp, up to about 500 bp, up to about 600 bp, up to about 700 bp, up to about 800 bp, up to about 900 bp, up to about 1000 bp, or more in length.

The length chosen for a marker molecule is also determined by the length of the genomic nucleic acid that is being sequenced. For example, cfDNA circulates in the human bloodstream as genomic fragments of cellular genomic DNA. Fetal cfDNA molecules found in the plasma of pregnant women are generally shorter than maternal cfDNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). DNA isolated from urine with a standard silica-based method consists of two fractions, high molecular weight DNA, which originates from shed cells and low molecular weight (150-250 base pair) fraction of transrenal DNA (Tr-DNA) (Botezatu et al., Clin Chem. 46: 1078-1084, 2000; and Su et al., J Mol. Diagn. 6: 101-107, 2004). The application of newly developed technique for isolation of cell-free nucleic acids from body fluids to the isolation of transrenal nucleic acids has revealed the presence in urine of DNA and RNA fragments much shorter than 150 base pairs (U.S. Patent Application Publication No. 20080139801). In embodiments, wherein cfDNA is the genomic nucleic acid that is sequenced, marker molecules that are chosen can be up to about the length of the cfDNA. For example, the length of marker molecules used in maternal cfDNA samples to be sequenced as single nucleic acid molecules or as clonally amplified nucleic acids can be between about 100 bp and 600. In other embodiments, the sample genomic nucleic acids are fragments of larger molecules. For example, a sample genomic nucleic acid that is sequenced is fragmented cellular DNA. In embodiments, when fragmented cellular DNA is sequenced, the length of the marker molecules can be up to the length of the DNA fragments. In some embodiments, the length of the marker molecules is at least the minimum length required for mapping the sequence read uniquely to the appropriate reference genome. In other embodiments, the length of the marker molecule is the minimum length that is required to exclude the marker molecule from being mapped to the sample reference genome.

In addition, marker molecules can be used to verify samples that are not assayed by nucleic acid sequencing, and that can be verified by common bio-techniques other than sequencing, e.g., real-time PCR.

Sample Controls (e.g, in Process Positive Controls for Sequencing and/or Analysis).

In various embodiments marker sequences introduced into the samples, e.g., as described above, can function as positive controls to verify the accuracy and efficacy of sequencing and subsequent processing and analysis.

Accordingly, compositions and method for providing an in-process positive control (IPC) for sequencing DNA in a sample are provided. In certain embodiments, positive controls are provided for sequencing cfDNA in a sample comprising a mixture of genomes are provided. An IPC can be used to relate baseline shifts in sequence information obtained from different sets of samples, e.g., samples that are sequenced at different times on different sequencing runs. Thus, for example, an IPC can relate the sequence information obtained for a maternal test sample to the sequence information obtained from a set of qualified samples that were sequenced at a different time.

Similarly, in the case of segment analysis, an IPC can relate the sequence information obtained from a subject for particular segment(s) to the sequence obtained from a set of qualified samples (of similar sequences) that were sequenced at a different time. In certain embodiments an IPC can relate the sequence information obtained from a subject for particular cancer-related loci to the sequence information obtained from a set of qualified samples (e.g., from a known amplification/deletion, and the like).

In addition, IPCs can be used as markers to track sample(s) through the sequencing process. IPCs can also provide a qualitative positive sequence dose value, e.g., NCV, for one or more aneuploidies of chromosomes of interest, e.g., trisomy 21, trisomy 13, trisomy 18 to provide proper interpretation, and to ensure the dependability and accuracy of the data. In certain embodiments IPCs can be created to comprise nucleic acids from male and female genomes to provide doses for chromosomes X and Y in a maternal sample to determine whether the fetus is male.

The type and the number of in-process controls depends on the type or nature of the test needed. For example, for a test requiring the sequencing of DNA from a sample comprising a mixture of genomes to determine whether a chromosomal aneuploidy exists, the in-process control can comprise DNA obtained from a sample known comprising the same chromosomal aneuploidy that is being tested. In some embodiments, the IPC includes DNA from a sample known to comprise an aneuploidy of a chromosome of interest. For example, the IPC for a test to determine the presence or absence of a fetal trisomy, e.g., trisomy 21, in a maternal sample comprises DNA obtained from an individual with trisomy 21. In some embodiments, the IPC comprises a mixture of DNA obtained from two or more individuals with different aneuploidies. For example, for a test to determine the presence or absence of trisomy 13, trisomy 18, trisomy 21, and monosomy X, the IPC comprises a combination of DNA samples obtained from pregnant women each carrying a fetus with one of the trisomies being tested. In addition to complete chromosomal aneuploidies, IPCs can be created to provide positive controls for tests to determine the presence or absence of partial aneuploidies.

An IPC that serves as the control for detecting a single aneuploidy can be created using a mixture of cellular genomic DNA obtained from a two subjects one being the contributor of the aneuploid genome. For example, an IPC that is created as a control for a test to determine a fetal trisomy, e.g., trisomy 21, can be created by combining genomic DNA from a male or female subject carrying the trisomic chromosome with genomic DNA with a female subject known not to carry the trisomic chromosome. Genomic DNA can be extracted from cells of both subjects, and sheared to provide fragments of between about 100-400 bp, between about 150-350 bp, or between about 200-300 bp to simulate the circulating cfDNA fragments in maternal samples. The proportion of fragmented DNA from the subject carrying the aneuploidy, e.g., trisomy 21, is chosen to simulate the proportion of circulating fetal cfDNA found in maternal samples to provide an IPC comprising a mixture of fragmented DNA comprising about 5%, about 10%, about 15%, about 20%, about 25%, about 30%, of DNA from the subject carrying the aneuploidy. The IPC can comprise DNA from different subjects each carrying a different aneuploidy. For example, the IPC can comprise about 80% of the unaffected female DNA, and the remaining 20% can be DNA from three different subjects each carrying a trisomic chromosome 21, a trisomic chromosome 13, and a trisomic chromosome 18. The mixture of fragmented DNA is prepared for sequencing. Processing of the mixture of fragmented DNA can comprise preparing a sequencing library, which can be sequenced using any massively parallel methods in singleplex or multiplex fashion. Stock solutions of the genomic IPC can be stored and used in multiple diagnostic tests.

Alternatively the IPC can be created using cfDNA obtained from a mother known to carry a fetus with a known chromosomal aneuploidy. For example, cfDNA can be obtained from a pregnant woman carrying a fetus with trisomy 21. The cfDNA is extracted from the maternal sample, and cloned into a bacterial vector and grown in bacteria to provide an ongoing source of the IPC. The DNA can be extracted from the bacterial vector using restriction enzymes. Alternatively, the cloned cfDNA can be amplified by, e.g., PCR. The IPC DNA can be processed for sequencing in the same runs as the cfDNA from the test samples that are to be analyzed for the presence or absence of chromosomal aneuploidies.

While the creation of IPCs is described above with respect to trisomies, it will be appreciated that IPCs can be created to reflect other partial aneuploidies including for example, various segment amplification and/or deletions. Thus, for example, where various cancers are known to be associated with particular amplifications (e.g., breast cancer associated with 20Q13) IPCs can be created that incorporate those known amplifications.

Sequencing Methods

As indicated above, the prepared samples (e.g., Sequencing Libraries) are sequenced as part of the procedure for identifying copy number variation(s). Any of a number of sequencing technologies can be utilized.

Some sequencing technologies are available commercially, such as the sequencing-by-hybridization platform from Affymetrix Inc. (Sunnyvale, CA) and the sequencing-by-synthesis platforms from 454 Life Sciences (Bradford, CT), Illumina/Solexa (Hayward, CA) and Helicos Biosciences (Cambridge, MA), and the sequencing-by-ligation platform from Applied Biosystems (Foster City, CA), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM)

or transmission electron microscopy (TEM). Illustrative sequencing technologies are described in greater detail below.

In one illustrative, but non-limiting, embodiment, the methods described herein comprise obtaining sequence information for the nucleic acids in a test sample, e.g., cfDNA in a maternal sample, cfDNA or cellular DNA in a subject being screened for a cancer, and the like, using Illumina's sequencing-by-synthesis and reversible terminator-based sequencing chemistry (e.g. as described in Bentley et al., Nature 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos (not to be confused with the anchor/anchored reads in the analysis of repeat expansion). Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free (e.g., PCR free) genomic library preparation is used, and the randomly fragmented genomic DNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adaptors attached to the two ends of the fragment, the adaptors allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced is also referred to as an insert.

In some implementation, a flow cell for clustering in the Illumina platform is a glass slide with lanes. Each lane is a glass channel coated with a lawn of two types of oligos. Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification, a strand folds over, and a second adapter region on a second end of the strand hybridizes with the second type of oligos on the flow cell surface. A polymerase generates a complimentary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves 2 reads from the two ends of a fragment. When a pair of reads are mapped to a reference sequence, the base-pair distance between the two reads can be determined, which distance can then be used to determine the length of the fragments from which the reads were obtained. In some instances, a fragment straddling two bins would have one of its pair-end read aligned to one bin, and another to an adjacent bin. This gets rarer as the bins get longer or the reads get shorter. Various methods may be used to account for the bin-membership of these fragments. For instance, they can be omitted in determining fragment size frequency of a bin; they can be counted for both of the adjacent bins; they can be assigned to the bin that encompasses the larger number of base pairs of the two bins; or they can be assigned to both bins with a weight related to portion of base pairs in each bin.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is also referred to as mate pair reads. In some embodiments involving mate pair reads, two biotin junction adaptors first are attached to two ends of a relatively long insert (e.g., several kb). The biotin junction adaptors then link the two ends of the insert to form a circularized molecule. A sub-fragment encompassing the biotin junction adaptors can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following URL, which is incorporated by reference by its entirety: resl.laluminal.lcom/documents/products/technotes/technote_nextera_matepair_data_processing. Additional information about paired end sequencing can be found in U.S. Pat. No. 7,601,499 and US Patent Publication No. 2012/0,053,063, which are incorporated by reference with regard to materials on paired end sequencing methods and apparatuses.

After sequencing of DNA fragments, sequence reads of predetermined length, e.g., 100 bp, are mapped or aligned to a known reference genome. The mapped or aligned reads and their corresponding locations on the reference sequence are also referred to as tags. In one embodiment, the reference genome sequence is the NCBI36/hg18 sequence, which is available on the world wide web at genome dot ucsc dot edu/cgi-bin/hgGateway?org=Human&db=hg18&hgsid=166260105). Alternatively, the reference genome sequence is the GRCh37/hg19, which is available on the world wide web at genome dot ucsc dot edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, CA, USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

Other sequencing methods and systems may be used to obtain sequence reads.

Apparatus and Systems for Determining CNV

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), chromosome and segment doses, calls such as aneuploidy calls, normalized chromosome and segment values, pairs of chromosomes or segments and corresponding normalizing chromosomes or segments, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the presence or absence of an aneuploidy, e.g., a fetal aneuploidy or cancer, in a test sample. The computer product may contain instructions for performing any one or more of the above-described methods for determining a chromosomal anomaly. As explained, the computer product may include a non-transitory and/or tangible computer readable medium having a computer executable or compilable logic (e.g., instructions) recorded thereon for enabling a processor to determine chromosome doses and, in some cases, whether a fetal aneuploidy is present or absent. In one example, the computer product comprises a computer readable medium having a computer executable or compilable logic (e.g., instructions) recorded thereon for enabling a processor to diagnose a fetal aneuploidy comprising: a receiving procedure for receiving sequencing data from at least a portion of nucleic acid molecules from a maternal biological sample, wherein said sequencing data comprises a calculated chromosome and/or segment dose; computer assisted logic for analyzing a fetal aneuploidy from said received data; and an output procedure for generating an output indicating the presence, absence or kind of said fetal aneuploidy.

The sequence information from the sample under consideration may be mapped to chromosome reference sequences to identify a number of sequence tags for each of any one or more chromosomes of interest and to identify a number of sequence tags for a normalizing segment sequence for each of said any one or more chromosomes of interest. In various embodiments, the reference sequences are stored in a database such as a relational or object database, for example.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable aneuploidy calls generally require mapping thousands (e.g., at least about 10,000) or even millions of reads to one or more chromosomes.

The methods disclosed herein can be performed using a system for evaluation of copy number of a genetic sequence of interest in a test sample. The system comprising: (a) a sequencer for receiving nucleic acids from the test sample providing nucleic acid sequence information from the sample; (b) a processor; and (c) one or more computer-readable storage media having stored thereon instructions for execution on said processor to carry out a method for identifying any CNV, e.g., chromosomal or partial aneuploidies.

In some embodiments, the methods are instructed by a computer-readable medium having stored thereon computer-readable instructions for carrying out a method for identifying any CNV, e.g., chromosomal or partial aneuploidies. Thus one embodiment provides a computer program product comprising one or more computer-readable non-transitory storage media having stored thereon computer-executable instructions that, when executed by one or more processors of a computer system, cause the computer system to implement a method for evaluation of copy number of a sequence of interest in a test sample comprising fetal and maternal cell-free nucleic acids. The method includes: (a) receiving sequence reads obtained by sequencing the cell-free nucleic acid fragments in the test sample; (b) aligning the sequence reads of the cell-free nucleic acid fragments to a reference genome comprising the sequence of interest, thereby providing test sequence tags, wherein the reference genome is divided into a plurality of bins; (c) determining sizes of the cell-free nucleic acid fragments existing in the test sample; (d) weighting the test sequence tags based on the sizes of cell-free nucleic acid fragments from which the tags are obtained; (e) calculating coverages for the bins based on the weighted tags of (d); and (f) identifying a copy number variation in the sequence of interest from the calculated coverages. In some implementations, weighting the test sequence tags involves biasing the coverages toward test sequence tags obtained from cell-free nucleic acid fragments of a size or a size range characteristic of one genome in the test sample. In some implementations, weighting the test sequence tags involves assigning a value of 1 to tags obtained from cell-free nucleic acid fragments of the size or the size range, and assigning a value of 0 to other tags. In some implementations, the method further involves determining, in bins of the reference genome, including the sequence of interest, values of a fragment size parameter including a quantity of the cell-free nucleic acid fragments in the test sample having fragment sizes shorter or longer than a threshold value. Here, identifying the copy number variation in the sequence of interest involves using the values of the fragment size parameter as well as the coverages calculated in (e). In some implementations, the system is configured to evaluate copy number in the test sample using the various methods and processes discussed above.

In some embodiments, the instructions may further include automatically recording information pertinent to the method such as chromosome doses and the presence or absence of a fetal chromosomal aneuploidy in a patient medical record for a human subject providing the maternal test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the maternal test sample was taken. This may involve performing one or more additional tests or analyses on additional samples taken from the subject.

Disclosed methods can also be performed using a computer processing system which is adapted or configured to perform a method for identifying any CNV, e.g., chromosomal or partial aneuploidies. One embodiment provides a computer processing system which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

Reads obtained by sequencing nucleic acids in a test sample

Tags obtained by aligning reads to a reference genome or other reference sequence or sequences The reference genome or sequence Sequence tag density—Counts or numbers of tags for each of two or more regions (typically chromosomes or chromosome segments) of a reference genome or other reference sequences Identities of normalizing chromosomes or chromosome segments for particular chromosomes or chromosome segments of interest Doses for chromosomes or chromosome segments (or other regions) obtained from chromosomes or segments of interest and corresponding normalizing chromosomes or segments Thresholds for calling chromosome doses as either affected, non-affected, or no call The actual calls of chromosome doses Diagnoses (clinical condition associated with the calls)

Recommendations for further tests derived from the calls and/or diagnoses

Treatment and/or monitoring plans derived from the calls and/or diagnoses

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to produce aneuploidy calls. At this remote location, as an example, the reads are aligned to a reference sequence to produce tags, which are counted and assigned to chromosomes or segments of interest. Also at the remote location, the counts are converted to doses using associated normalizing chromosomes or segments. Still further, at the remote location, the doses are used to generate aneuploidy calls.

Among the processing operations that may be employed at distinct locations are the following:

Sample collection

Sample processing preliminary to sequencing

Sequencing

Analyzing sequence data and deriving aneuploidy calls

Diagnosis

Reporting a diagnosis and/or a call to patient or health care provider

Developing a plan for further treatment, testing, and/or monitoring

Executing the plan

Counseling

Any one or more of these operations may be automated as described elsewhere herein. Typically, the sequencing and the analyzing of sequence data and deriving aneuploidy calls will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to sequencing may be performed include health practitioners' offices, clinics, patients' homes (where a sample processing apparatus or kit is provided), mobile health care vehicles, and facilities of aneuploidy analysis providers. Examples of locations where sequencing may be performed include health practitioners' offices, clinics, health practitioners' offices, clinics, patients' homes (where a sample sequencing apparatus and/or kit is provided), mobile health care vehicles, and facilities of aneuploidy analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of an aneuploidy analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis (e.g., the fetus has Downs syndrome or the patient has a particular type of cancer) is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis and derivation of aneuploidy operation. In some implementations, the result of this processing operation is then automatically delivered, possibly with reformatting as a diagnosis, to a system component or entity that processes reports the information to a health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 17:
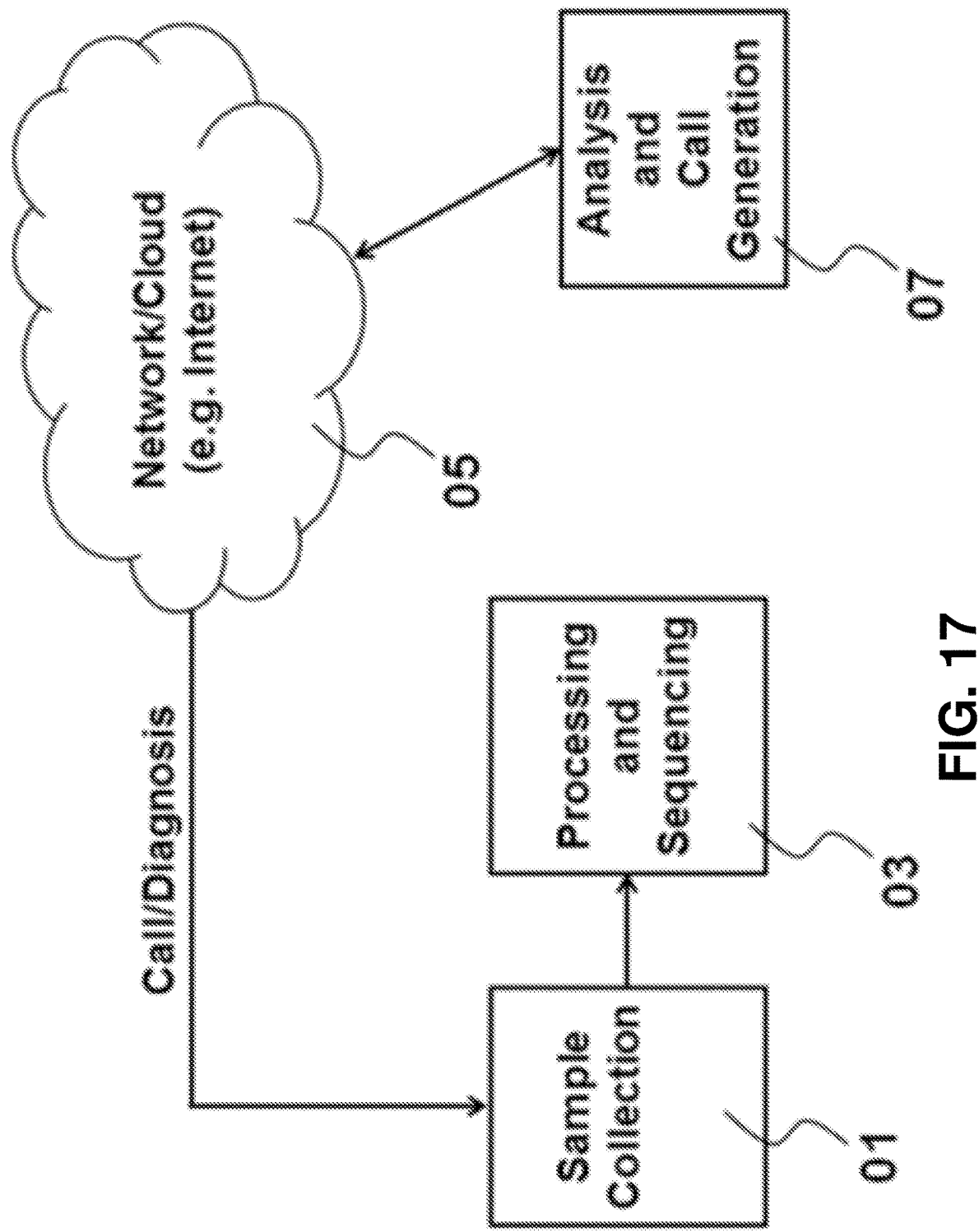
FIG. 17 shows one implementation of a dispersed system for producing a call or diagnosis from a test sample.

FIG. 17 shows one implementation of a dispersed system for producing a call or diagnosis from a test sample. A sample collection location 01 is used for obtaining a test sample from a patient such as a pregnant female or a putative cancer patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 17.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 17. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 18:
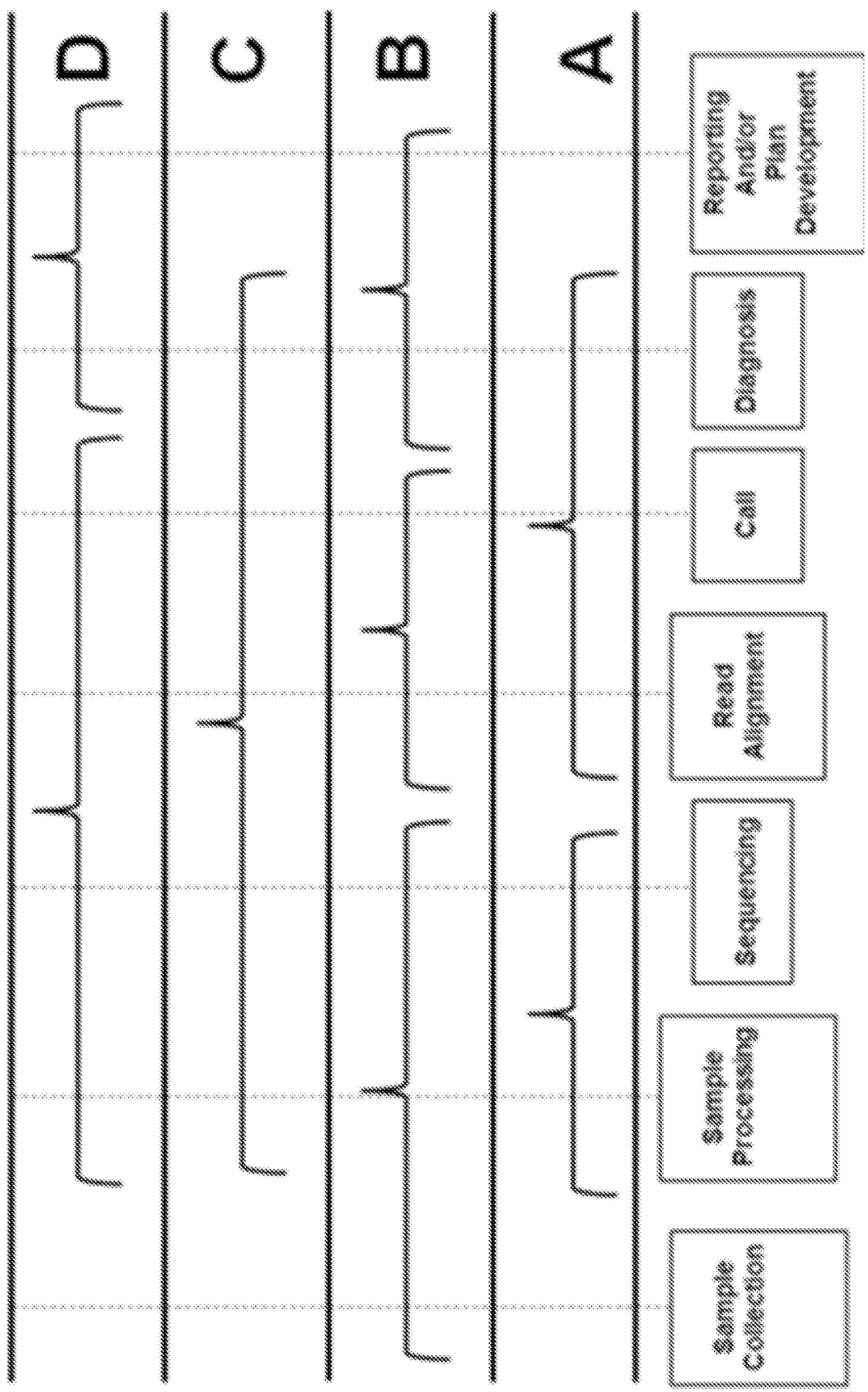
FIG. 18 shows the options for performing various operations at distinct locations.

FIG. 18 elaborates on the options for performing various operations at distinct locations. In the most granular sense depicted in FIG. 18, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 18 identified by reference character A. In another implementation, which is identified by character B in FIG. 18, sample collection, sample processing, and sequencing are all performed at the same location. In this implementation, read alignment and calling are performed in a second location. Finally, diagnosis and reporting and/or plan development are performed in a third location. In the implementation depicted by character C in FIG. 18, sample collection is performed at a first location, sample processing, sequencing, read alignment, calling, and diagnosis are all performed together at a second location, and reporting and/or plan development are performed at a third location. Finally, in the implementation labeled D in FIG. 18, sample collection is performed at a first location, sample processing, sequencing, read alignment, and calling are all performed at a second location, and diagnosis and reporting and/or plan management are performed at a third location.

One embodiment provides a system for use in determining the presence or absence aneuploidies in a test sample comprising fetal and maternal nucleic acids, the system including a sequencer for receiving a nucleic acid sample and providing fetal and maternal nucleic acid sequence information from the sample; one or more processors configured to: (a) determine a value of fetal fraction of the test sample, wherein the fetal fraction of the test sample indicates the relative amount of fetal origin cell-free nucleic acid fragments in the test sample; (b) receive, by the computer system, sequence reads obtained by sequencing the cell-free nucleic acid fragments in the test sample; (c) align, by the computer system, the sequence reads of the cell-free nucleic acid fragments to a reference genome comprising a sequence of interest, thereby providing sequence tags; (d) determine, by the computer system, a coverage of the sequence tags for at least a portion of the reference genome; and (e) determine that the test sample is within an exclusion region based on the coverage of sequences tags determined in (d) and the fetal fraction determined in (a), wherein the exclusion region is defined by at least a fetal fraction limit of detection (LOD) curve, wherein the fetal fraction LOD curve varies with coverage values and indicates minimum values of fetal fractions needed to achieve a detection criterion given different coverages.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

In some embodiments of any of the systems provided herein, the one or more processors are programed to perform various methods described above.

Another aspect of the disclosure relates to a computer program product comprising a non-transitory machine readable medium storing program code that, when executed by one or more processors of a computer system, causes the computer system to: (a) determine a value of fetal fraction of the test sample, wherein the fetal fraction of the test sample indicates the relative amount of fetal origin cell-free nucleic acid fragments in the test sample; (b) receive, by the computer system, sequence reads obtained by sequencing the cell-free nucleic acid fragments in the test sample; (c) align, by the computer system, the sequence reads of the cell-free nucleic acid fragments to a reference genome comprising a sequence of interest, thereby providing sequence tags; (d) determine, by the computer system, a coverage of the sequence tags for at least a portion of the reference genome; and (e) determine that the test sample is within an exclusion region based on the coverage of sequences tags determined in (d) and the fetal fraction determined in (a), wherein the exclusion region is defined by at least a fetal fraction limit of detection (LOD) curve, wherein the fetal fraction LOD curve varies with coverage values and indicates minimum values of fetal fractions needed to achieve a detection criterion given different coverages.

In some embodiments of the systems provided herein, the computer program product comprises a non-transitory machine readable medium storing program code to be executed by the one or more processors to perform the various methods described above.

EXPERIMENTAL

Example 1

The purpose of this example is to illustrate how LOD curve can be obtained using the methods described above.

Study Design

For this study, a portion of the data generated in the VeriSeq NIPT Precision Study (BRIGID-0147 VeriSeq NIPT: Precision Study Protocol and BRIGID-0166 VeriSeq NIPT—Precision Study Report) was used to determine the limit of detection of the VeriSeq NIPT Solution system.

In the VeriSeq NIPT Precision study, pooled cfDNA from Trisomy-21 and non-pregnant plasma pools were combined to create a 5% fetal fraction Trisomy-21 affected pool which was processed through the VeriSeq NIPT assay. Male maternal pools were also processed through the VeriSeq NIPT assay as-is.

Table 1 shows the Within-Lab Precision portion of the precision study design which was used for the LOD study. The Within-Lab Precision portion consisted of 2 Hamilton instruments, 2 NextSeq instruments, and three reagent lots for a total of 12 runs conducted on 6 different days.

TABLE 1

| Within-Lab Precision portion of Precision Study |
|---|
| Within-Lab Precision Site 3 |

| Hamilton 3 | | | | | | Hamilton 4 | | | | | |
|---|---|---|---|---|---|---|---|---|---|---|---|
| NextSeq 3 | | | NextSeq 4 | | | NextSeq 4 | | | NextSeq 3 | | |
| Reagent Lots | | | | | | Reagent lots | | | | | |
| 1 | 2 | 3 | 1 | 2 | 3 | 1 | 2 | 3 | 1 | 2 | 3 |
| Run 10 | Run 12 | Run 14 | Run 16 | Run 18 | Run 20 | Run 11 | Run 13 | Run 15 | Run 17 | Run 19 | Run 21 |

Automation and sequencing instruments were paired with a consistent operator. Operator and instrument variation were combined.

Data generated with reagent lots 1 and 2 were used for establishing limit of detection. By combining the sequence data from the T21 (5% FF) with the sequence data from the non-pregnant female, we generated synthetic sequence data for T21 samples with varying fetal fractions. The process was repeated for 5 different levels of sequencing depth (2, 4, 6, 8 and 10 million of uniquely align reads coverage—see Table 2). Dilution points were selected on a fine grid in a wide range, to cover expected limit of detection for all levels of sequencing depth (1.25%-4.5%) with step size 0.25%.

For each dilution point and each coverage level, 20 replicated synthetic samples were generated (a more detailed method description can be found in DEV REPORT-0072, Mathematical model for Log Likelihood Ratio score and prediction of Limit of Detection).

Using in silico generated dilution series, LoD for T21 was established using probit regression method as described in BRIGID-0150 (VeriSeq NIPT Solution Design Verification Protocol Limit of Detection) for each level of coverage. In addition, LOD for T13 and T18 were determined using the results for the LOD for T21 and a known relationship between LOD T21 and LOD T13 and T18 respectively, as described in DEV REPORT-0072.

Results

The quantitative scores, Log-Likelihood Ratio (LLR) and estimates for fetal fraction for each replicate run were calculated by the R&D Clinical Aneuploidy Detection and Analysis Suite (cADAS) v3.2.

Sample Filtering and Outliers

Figure 19:
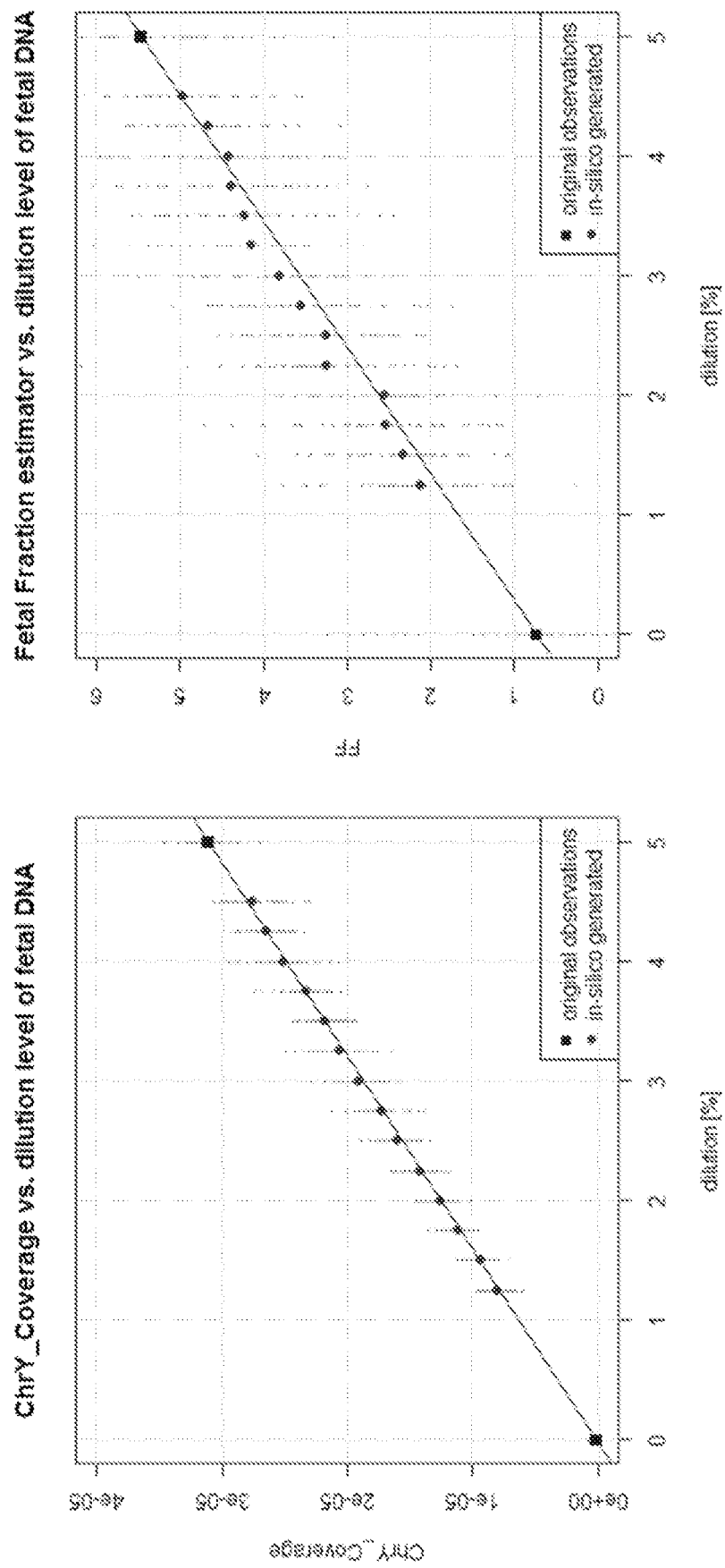
FIG. 19 shows the chromosome Y coverage (left plot) and FF fraction estimator (right plot) for the synthetically generated samples as a function of dilution fraction.

All No-Template Control (NTC) samples were excluded from analysis. Subsequent removal of these samples yielded 564 samples with N=48 T21 pools and N-48 Non-pregnant pools. Which were used in further in silico dilution analysis. Rest of the samples was not directly used and served as fillers for the analysis. One of the non-pregnant samples was marked as NES_FF_QC failure, This QC failure was ignored and sample was included in the analysis, because the sample is non-pregnant (does not have fetal DNA in it) thus expected to fail this metric In Silico Dilution Quality Verification Affected samples were prepared from a pooled mixture of male and female plasma samples with approximately 50% of each. Therefore chrY DNA was present in the samples and could be used for verification of the in silico dilution process. FIG. 19 shows the chromosome Y coverage (left plot) and FF fraction estimator (right plot) for the synthetically generated samples as a function of dilution fraction. Both linear plots showed the coordinated value between FF (original non-pregnant FF=0% and affected FF=5%) and the in silico dilution.

Determining Limit of Detection for Trisomy T21 Test

The procedure for determining LOD from experimental observations for specified levels of coverage is described in BRIGID 0150 vA. (VeriSeq NIPT Solution Design Verification Protocol Limit of Detection).

Measured LOD for T21 for each lot and each coverage level are summarized in Table 2.

TABLE 2

LIMIT OF DETECTION LOD

| Coverage | Precision Study (BRIGID-166) Lot | | | Average | Max (most conservative) |
| --- | --- | --- | --- | --- | --- |
| | Lot 1 | Lot 2 | Lot 3 | | |
| 2 M | 4.3 | 4.1 | 4.4 | 4.3 | 4.4 |
| 4 M | 3.5 | 3.1 | 3.1 | 3.2 | 3.5 |
| 6 M | 3.1 | 2.6 | 2.6 | 2.8 | 3.1 |
| 8 M | 2.9 | 2.2 | 2.1 | 2.4 | 2.9 |
| 10 M | 2.3 | 2 | 2.1 | 2.1 | 2.3 |

Limit of Detection Vs. Coverage

Figure 20:
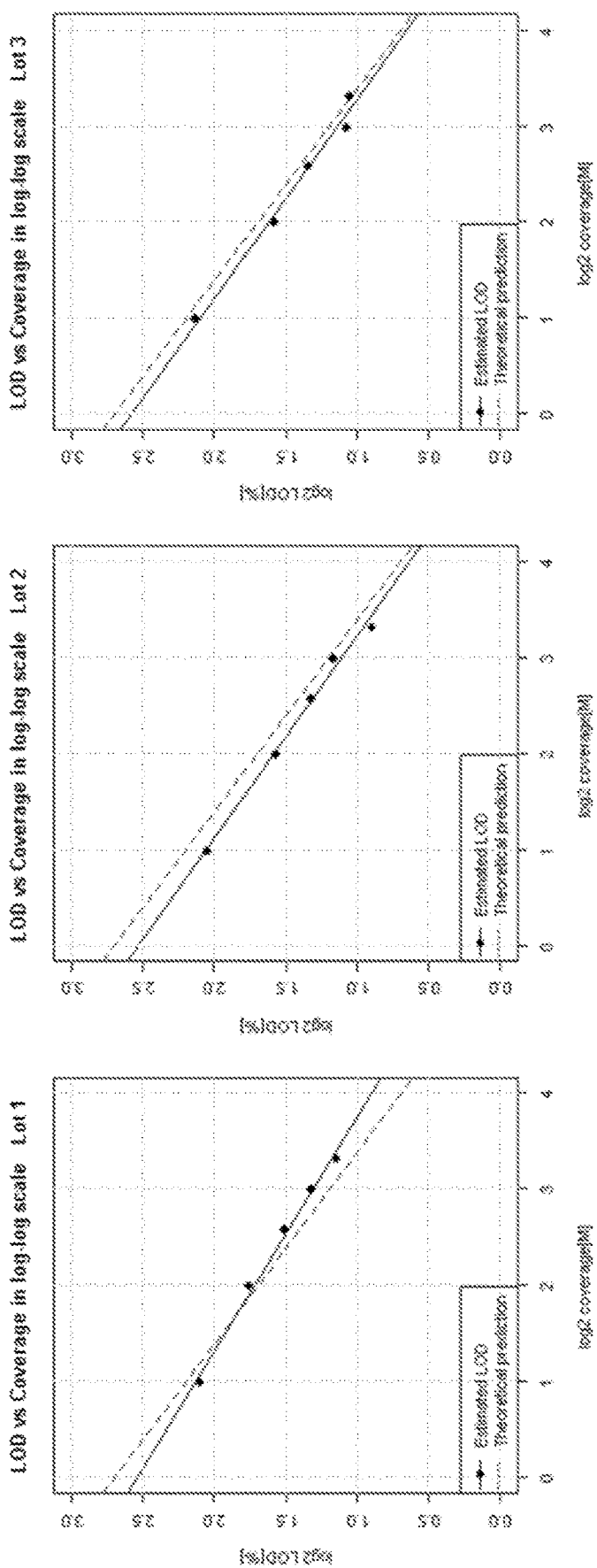
FIG. 20 shows the results of linear fit of LOD vs coverage.

The theoretical model described in DEV REPORT-0072 (Mathematical model for Log Likelihood Ratio score and prediction of Limit of Detection) predicts that LOD vs Coverage in Log-Log scale is a straight line. FIG. 20 shows the results of linear fit of LOD vs coverage (as listed in Table-6.2). We observe a close match of experimental data with the predicted behavior.

Figure 21:
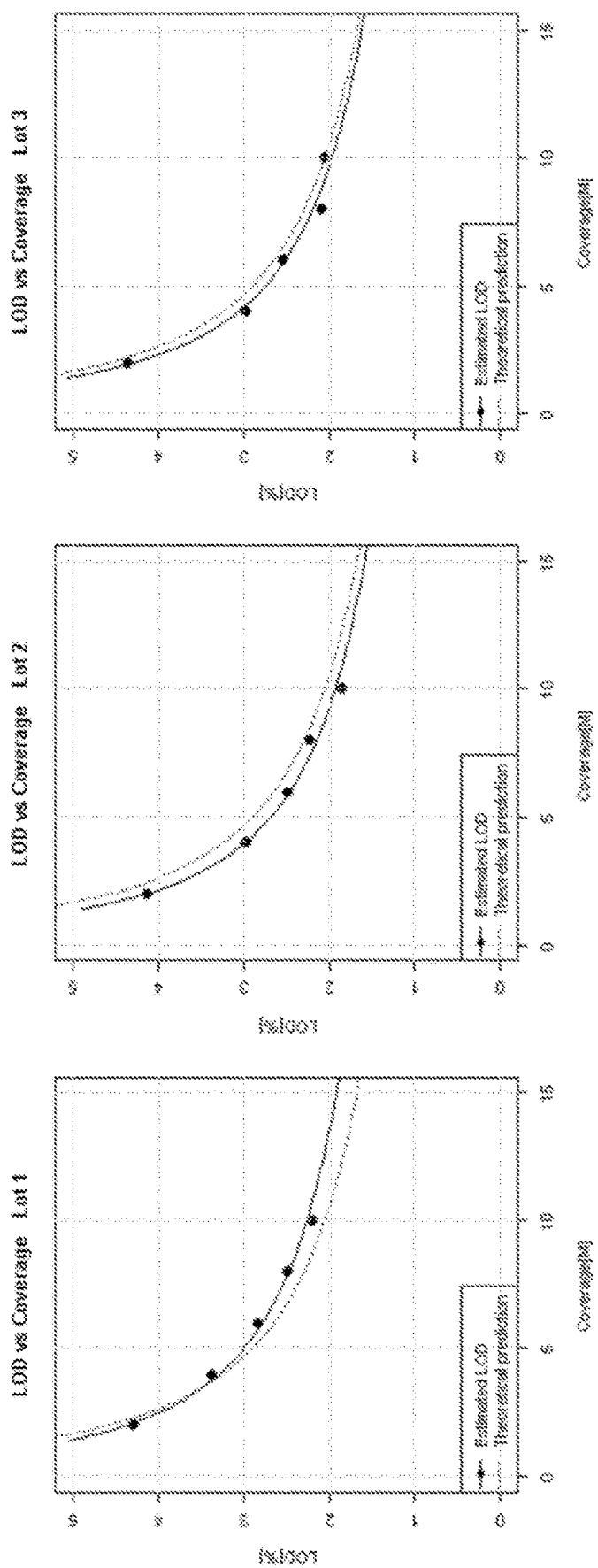
FIG. 21 shows the results of predicted LOD overlaid with observed LOD.

Fitted LOD vs coverage line predicts the Limit of Detection for any coverage. The results of predicted LOD overlaid with observed LOD are shown in FIG. 21.

Limit of Detection for Average Case

Figure 22:
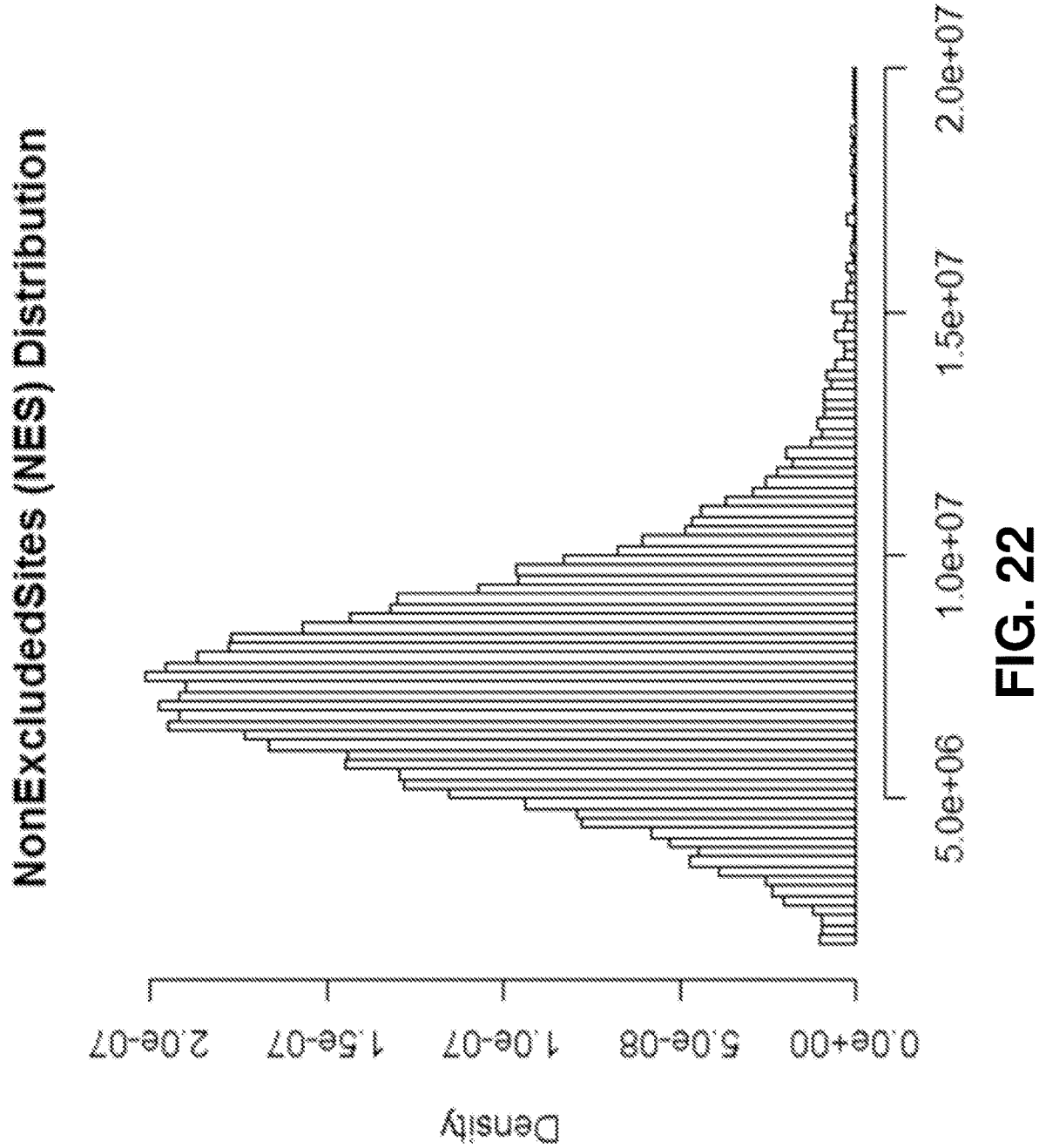
FIG. 22 shows a probability density function of NES.

The general population of samples have variable coverage. FIG.-6.4 shows the distribution of coverage (NES) in a large number of samples (N=14,400) processed using V2 version of the VeriSeq NIPT assay. The expected LOD for the general population is computed as the expectation of LOD as function of coverage over the coverage distribution $\int_{2M}^{20M} LOD(NES)*p(NES)dNES$ where LOD(NES) is a LOD as function of coverage, and p(NES) is probability density function of NES shown on FIG. 22. The resulting average case LOD for T21 is presented in Table 3

TABLE 3

LIMIT OF DETECTION FOR AVERAGE POPULATION COVERAGE

| Metric | Lot1 | Lot2 | Lot3 |
| --- | --- | --- | --- |
| LOD21 | 2.81% | 2.40% | 2.43% |

Limit of Detection for Other Aneuploidies T13, T18

As described in a previous study (Mathematical model for Log Likelihood Ratio score and prediction of Limit of Detection), limit of detection for aneuploidy of different chromosomes could be inferred from the known LOD for at least one of the chromosomes. Using the relationship from prior studies, we can infer LOD for trisomy T13 and T18 using the previously determined multiplication factors with results shown in Table 4 and Table 5.

TABLE 4

INFERRED LIMIT OF DETECTION FOR AVERAGE POPULATION COVERAGE FOR T13 ANDT18 EVALUATION AGAINST ACCEPTANCE CRITERIA

| Aneuploidy | Observed LoD | LoD factor | Inferred from T21 LoD |
| --- | --- | --- | --- |
| T21 | 2.81% | 100% | 2.81% |
| T18 | NA | 81% | 2.27% |
| T13 | NA | 72% | 2.02% |

TABLE 5

| Precision % CV Acceptance Criteria | | | |
|---|---|---|---|
| Metric | % FF | Passing criteria | Pass/Fail |
| LOD13 | 2.02% | LOD < 4% | PASS |
| LOD18 | 2.27% | LOD < 4% | PASS |
| LOD21 | 2.81% | LOD < 4% | PASS |

CONCLUSION

The Limit of Detection (LOD) of the VeriSeq NIPT system with respect to the fetal fraction of fetal cfDNA (trisomies 13/18/21) on a background of normal maternal diploid cfDNA has been determined. Limit of detection values are summarized in Table 6. For all tested aneuploidies the observed LOD was found below the values specified in the test requirements documents. Based on the data presented in Table 6, the determined limits of detection passed the acceptance criteria of another study for all targeted aneuploidies.

TABLE 6

| Aneuploidy Fetal fraction LOD | |
|---|---|
| Aneuploidy | LOD (% FF) |
| T13 | 2.02% |
| T18 | 2.27% |
| T21 | 2.81% |

Example 2

Example 2 shows empirical data of various performance metrics of the conventional method labeled as NES and the fetal fraction LOD curve method described above.

Figure 23:
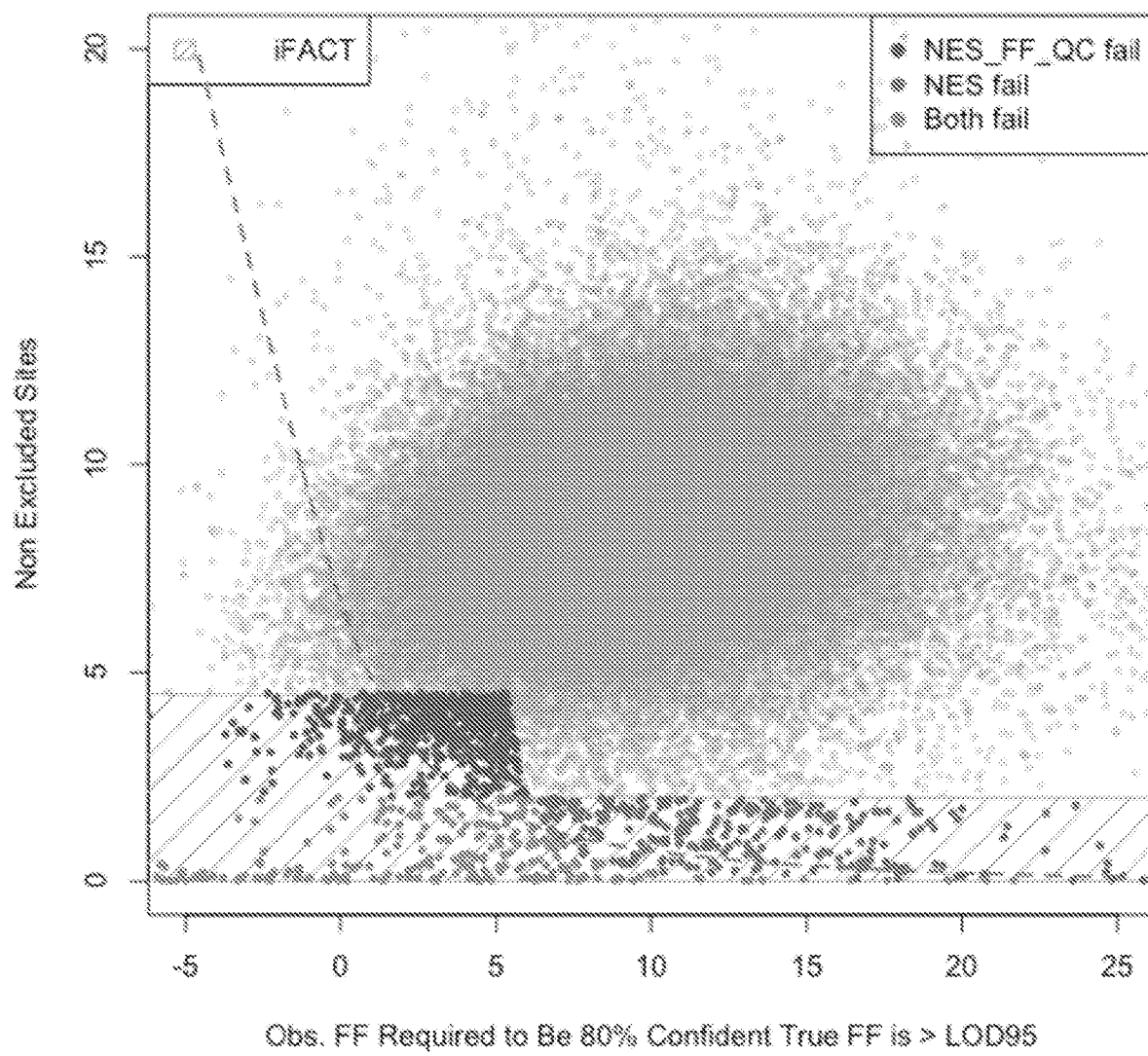
FIG. 23 shows NES coverage as a function of observed fetal fraction.

FIG. 23 shows NES coverage as a function of observed fetal fraction. The two-step coverage threshold technique is used to exclude samples. Various samples falling in the exclusion regions can be seen in the figure. Most of the samples excluded have fetal fraction between 0 and 20%. And their coverages are limited by the two levels of thresholds.

Figure 24:
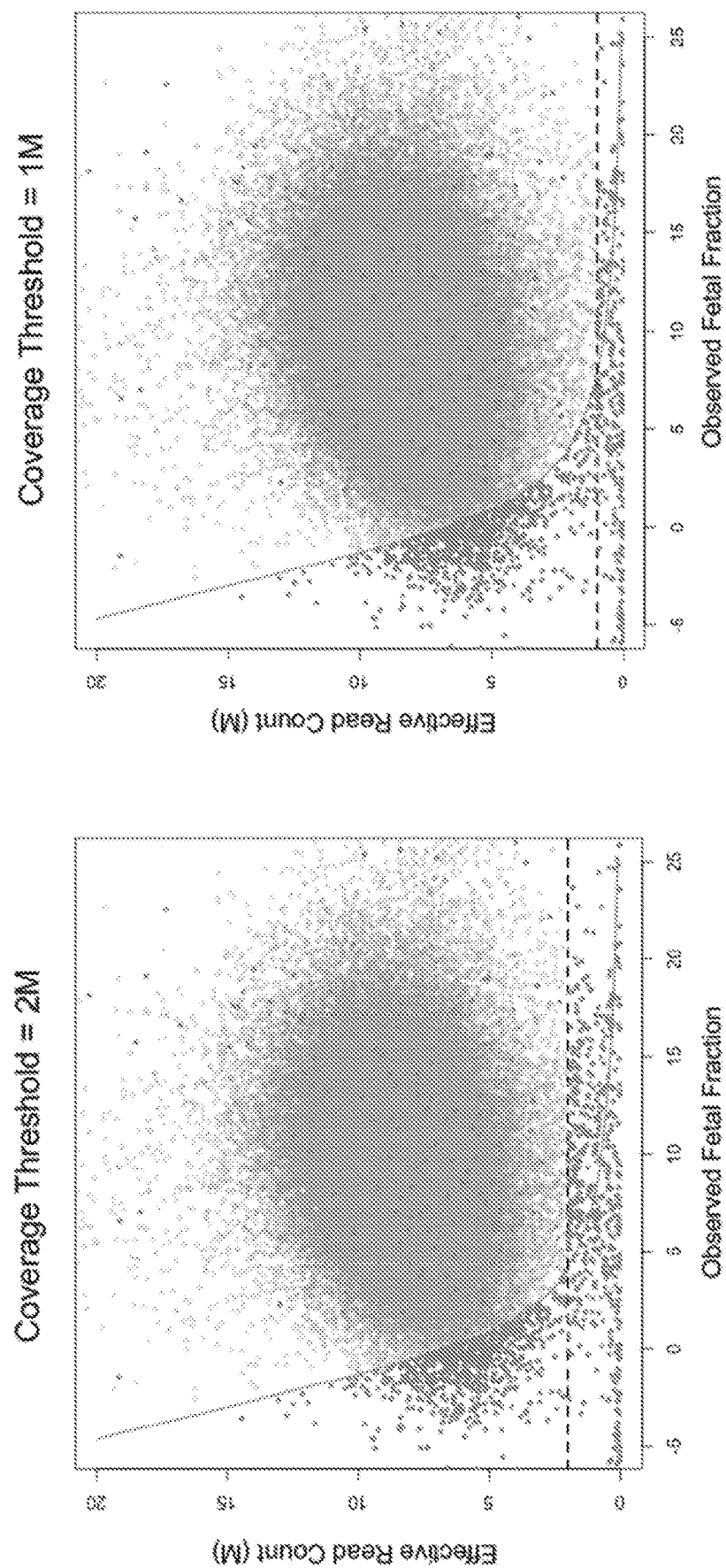
FIG. 24 shows data exclusion using exclusion area that is defined by an LOD curve and read threshold.

FIG. 24 shows data exclusion using exclusion area that is defined by an LOD curve and read threshold. The left panel has the read threshold at 2 million reads. Right panel shows the data using a coverage threshold of 1 million reads. As the figure illustrates, one can lower the coverage threshold to exclude fewer samples in the conditions in which it is desirable to exclude fewer samples. Many excluded samples have a relatively high read coverage and low observed fetal fraction. In contrast, in FIG. 23 many excluded samples have a relatively high fetal fraction and low coverage.

FIG. 25 shows the pass rates and failure rates for the first run and the second run for the prior methods and the LOD QC method described above. The data show that both methods have similar pass rates and failure rates. The final failure rates for the prior method is 0.42%. And it is 0.38% for the LODQC method.

Figure 26:
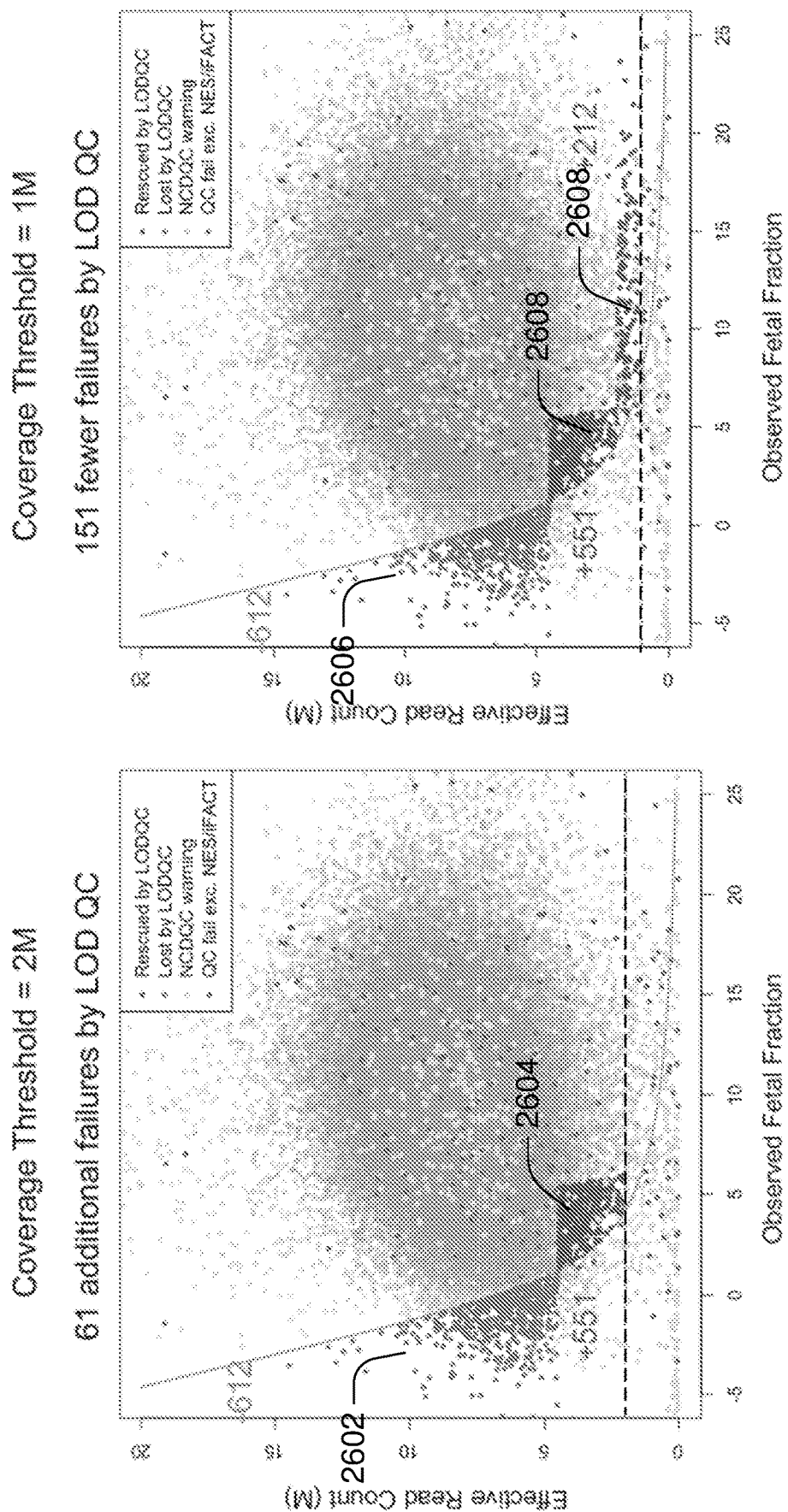
FIG. 26 shows data that are excluded by the two-step thresholding and rescued by the fetal fraction LOD curve method.

FIG. 26 shows data that are excluded by the two-step thresholding and rescued by the fetal fraction LOD curve method labeled as 2604. The samples that are excluded by the LOD QC method and rescued by the conventional method are shown in area 2602. The left panel of FIG. 26 shows the data for a coverage threshold of 2 million reads combined with an LOD curve. The right panel shows the rescued data for a lower coverage threshold of 1 million reads. Using the coverage threshold 2 million reads on the left, LODQC method excluded 61 additional samples. But when the coverage threshold is lowered to 1 million reads, 151 fewer samples are excluded by the LOD QC method.

Figure 27:
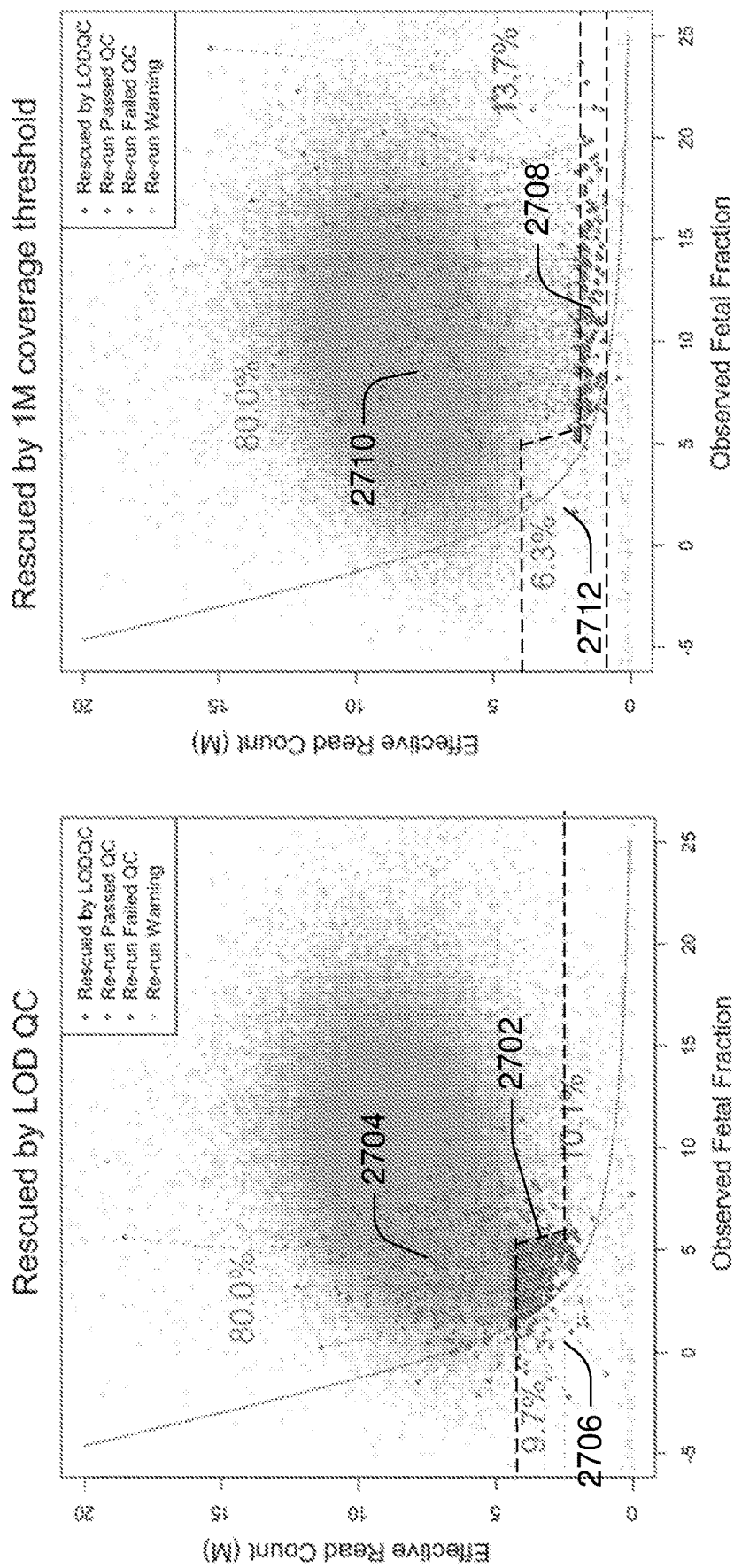
FIG. 27 shows the samples that are rescued by the LOD QC method.

FIG. 27 shows the samples that are rescued by the LOD QC method. The left panel shows in area 2702 the samples that are excluded by the conventional methods and rescued by the LO DQC method. After rerun, 80% of those samples fall within the inclusion area 2704. While 10% of the samples remain in the same area 2702. 9.7% of the samples fell below the LOD curve and into the exclusion region. The right panel shows samples that are rescued by the 1 million coverage threshold applied with the LOD curve. Samples excluded by the conventional method that are rescued by the 1 million reads threshold are shown in area 2708. After rerunning the samples, 80% moved into the inclusion area 2710, 13.7% remains in the same area 2708, and 6.3% fall below the LOD curve into the exclusion area. This figure shows that the LOD method alone or LOD method combined with coverage threshold method can rescue a large percentage of samples that would have otherwise been excluded. In practice, the LODQC method helps to avoid the need to rerun the samples that are rescued, thereby saving time, cost, and resources for CNV detection.

Figure 28:
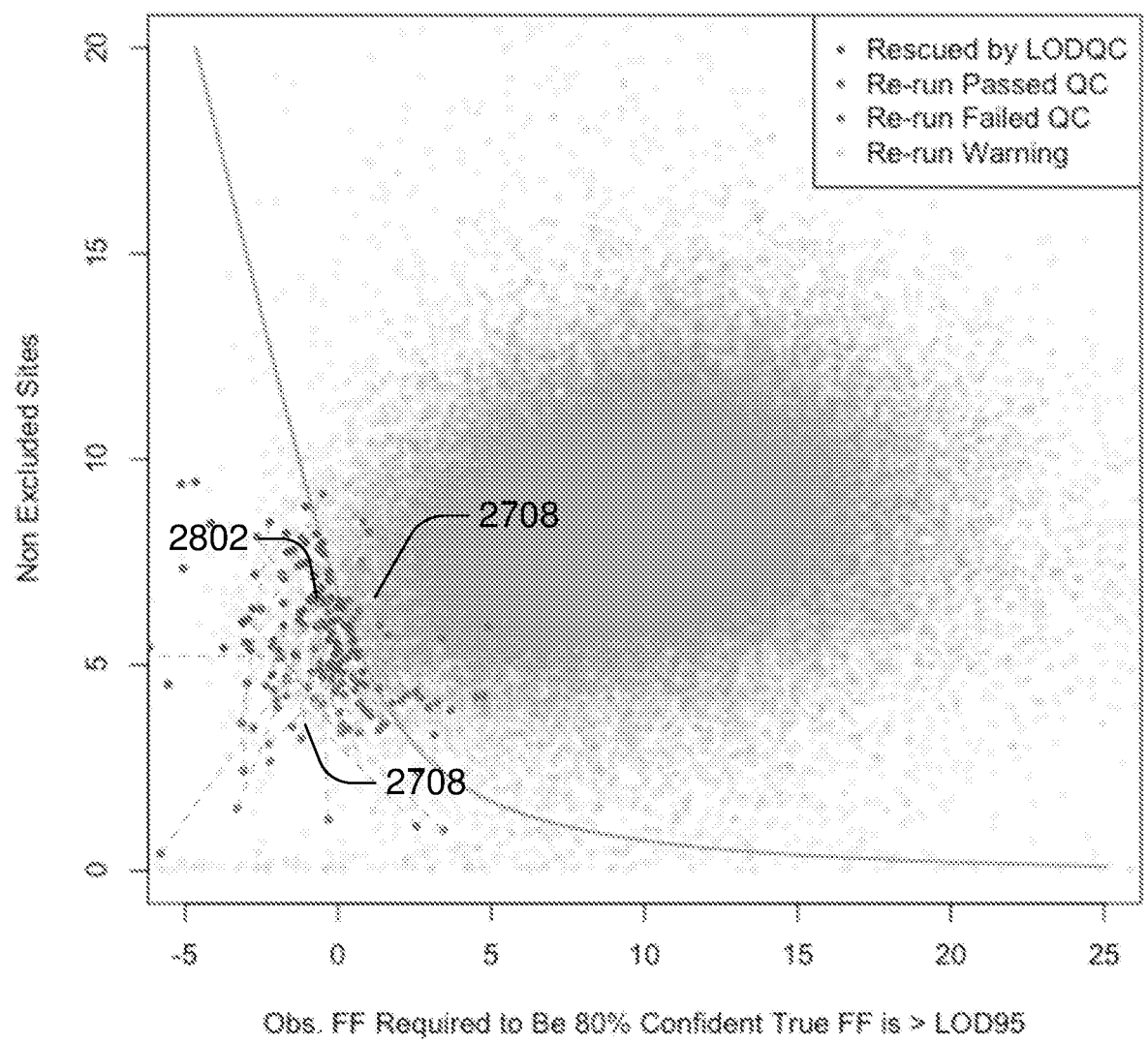
FIG. 28 shows the samples that were excluded by the LOD QC method.

FIG. 28 shows the data that were excluded by the LOD QC method in area 2802. After rerun, few samples moved above the LOD curve, into inclusion area 2708. More data stay in the same 2802 region or move further below the LOD curve 2708. The results from FIG. 27 and FIG. 28 suggest that the LODQC method includes many samples that are actually meeting QC conditions, and excludes samples that cannot meet the QC standard, even upon re-run. This illustrates that the LODQC method can intelligently and correctly separate the positive and negative samples FIG. 29 shows the pass and failure rates for two runs for the existing prior method and the LODQC method. Overall, the pass rates and failure rates in both the first run and the second run are similar for the two methods.

Figure 30:
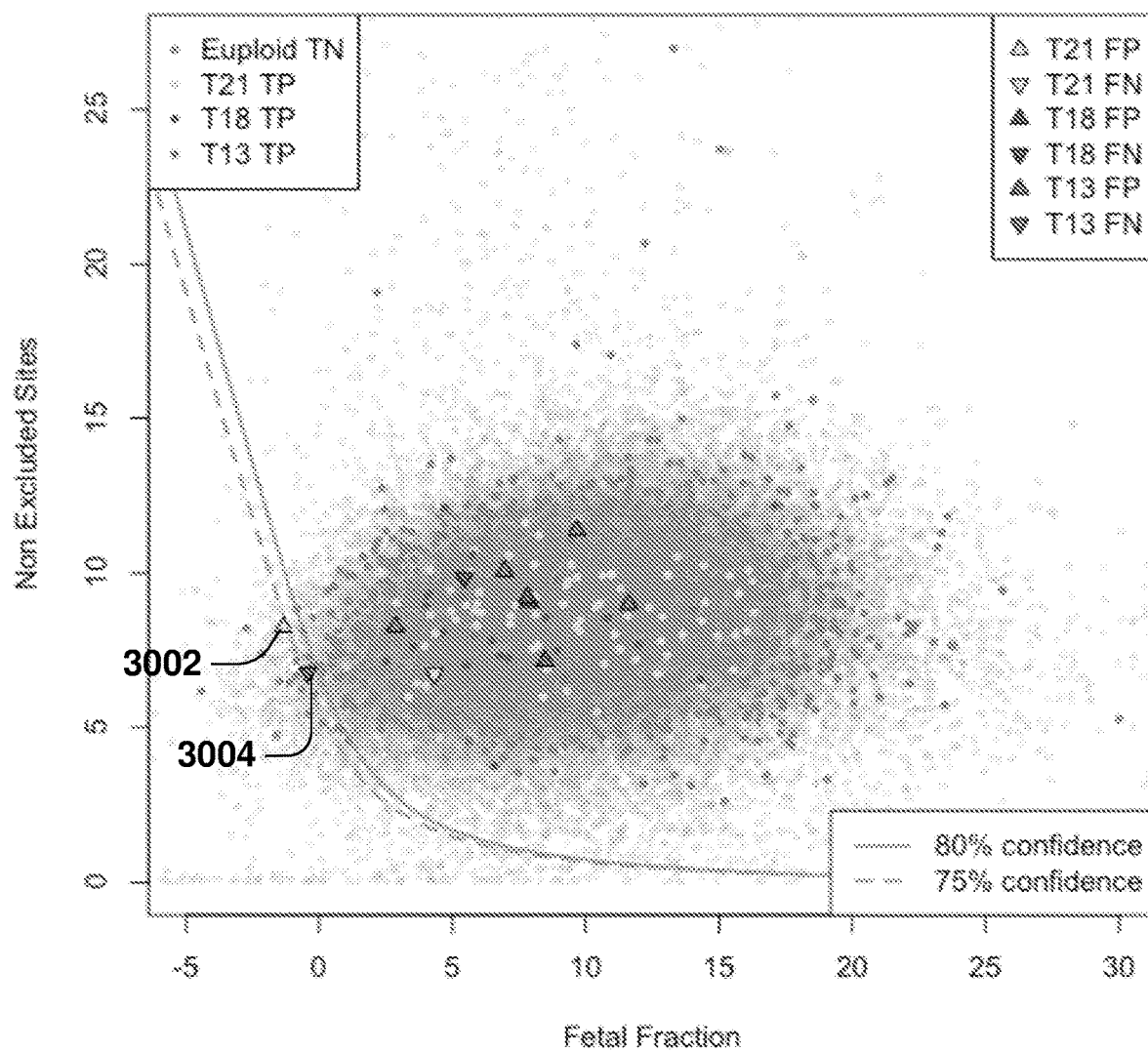
FIG. 30 shows that the 75% confidence LOD curve rescued samples.

FIG. 30 shows that the 75% confidence LOD curve rescued sample 3002, which is trisomy 21 (T21) false positive. It also rescued samples 3004 which is trisomy 18 (T18) false negative. This results in a 100% reduction in T21 false positives and 50% reduction in T18 false negatives. It illustrates that the LOD QC method can increase both sensitivity and specificity.

Figure 31:
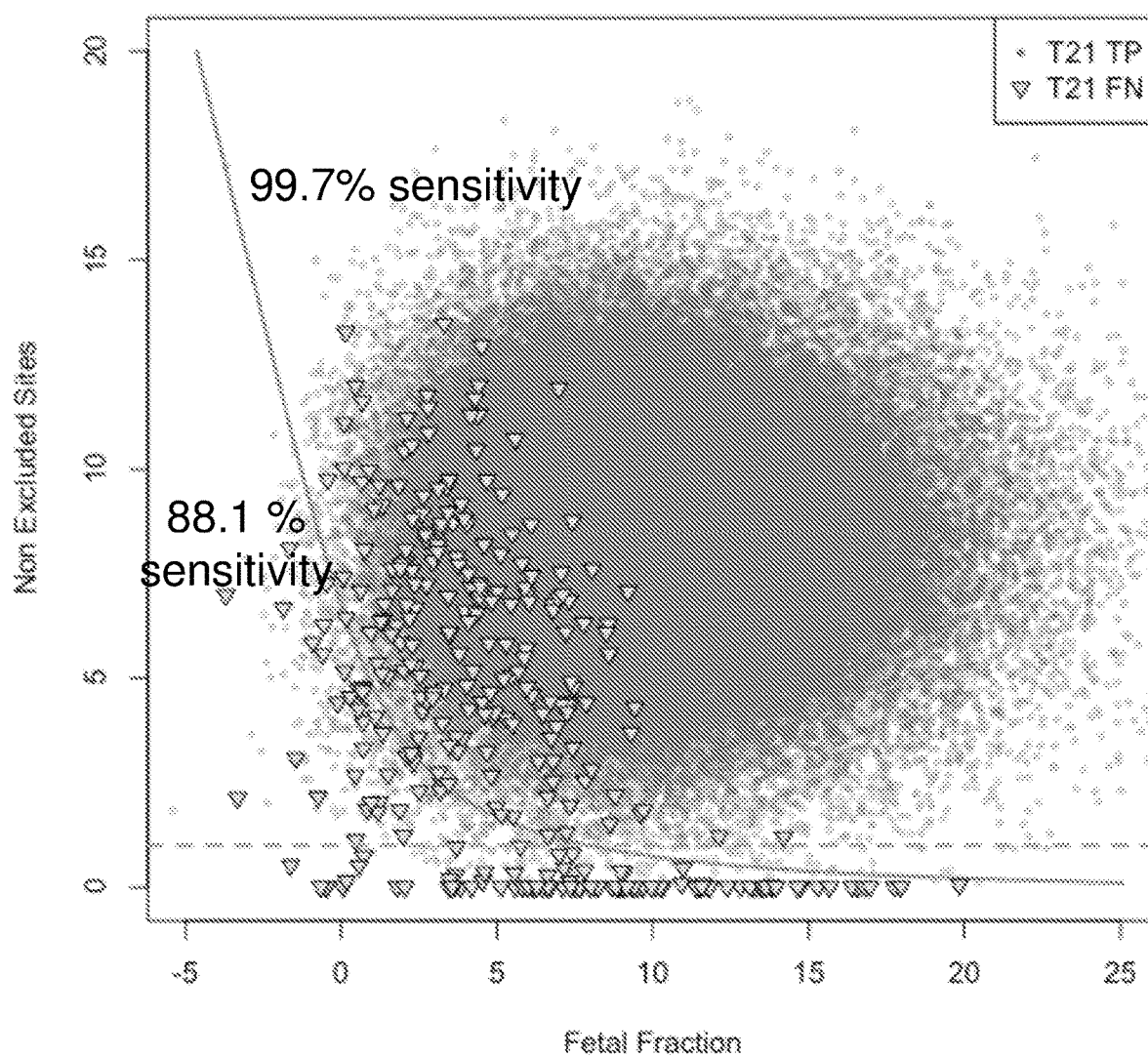
FIG. 31 shows sensitivities for detecting T21 samples using methods of some implementations.

FIG. 31 shows that for simulated T21 samples, those that pass the LOD QC can be detected with 99.7% sensitivity and those fail the LOD QC can be detected with 88.1% sensitivity. The overall sensitivity in all samples regardless of LODQC status is 99.7.

What is claimed is:

1. A method, implemented using a nucleic acid sequencer and a computer system comprising one or more processors and memory, for processing a test sample comprising cell-free nucleic acid fragments originating from a mother and a fetus, the method comprising:
   (A) sequencing, at a first depth of sequencing, the test sample comprising the cell-free nucleic acid fragments originating from a mother and a fetus;
   (B) computationally analyzing sequence information from the test sample, the analyzing comprising:
      (a) determining an observed value of a fetal fraction of the test sample, wherein the fetal fraction of the test sample indicates a relative amount of fetal origin cell-free nucleic acid fragments in the test sample;

(b) receiving, by the computer system, sequence reads obtained by sequencing the cell-free nucleic acid fragments in the test sample;

(c) aligning, by the computer system, the sequence reads of the cell-free nucleic acid fragments to a reference genome comprising a sequence of interest, thereby providing sequence tags;

(d) determining, by the computer system, a coverage of the sequence tags for at least a portion of the reference genome; and (e) determining that the test sample is within an exclusion region based on the coverage of sequences tags determined in (d) and the observed value of the fetal fraction determined in (a), wherein the exclusion region is defined by at least a fetal fraction limit of detection (LOD) curve, wherein the fetal fraction LOD curve varies with coverage values and indicates, for a given coverage value of different coverage values, a minimum observed value of the fetal fraction to achieve a given level of confidence that a corresponding ground truth fetal fraction is greater than a minimum value of fetal fractions needed to achieve a detection criterion; and (C) re-sequencing, at a second depth of sequencing that is greater than the first depth of sequencing, the test sample to obtain re-sequenced sequence reads;

(D) repeating (B) (a)-(d) for the re-sequenced sequence reads; and (E) determining that the re-sequenced test sample is outside the exclusion region;

further comprising: obtaining the LOD curve by:

(i) selecting from a first plurality of training samples, for each observed fetal fraction of a plurality of observed fetal fractions and for each coverage level of a plurality of coverage levels, one or more selected training samples whose true fetal fractions have the given level of confidence, wherein each training sample comprises cell-free nucleic acid fragments originating from a mother and a fetus, (ii) obtaining, using the one or more selected training samples for each observed fetal fraction and each coverage level, true fetal fraction versus observed fetal fraction curves of the plurality of coverage levels, (iii) obtaining, using a second plurality of training samples, true fetal fractions having at least the minimum value of fetal fraction needed to achieve the detection criterion for the plurality of coverage levels, (iv) obtaining, using the true fetal fraction versus observed fetal fraction curves and the true fetal fractions having at least the minimum value of fetal fraction needed to achieve the detection criterion, a plurality of minimal observed fetal fractions for the plurality of coverage levels required to have the given level of confidence that true fetal fractions have at least the minimum value of fetal fraction needed to achieve the detection criterion, and (v) obtaining the fetal fraction LOD curve using the plurality of minimal observed fetal fractions for the plurality of coverage levels.

2. The method of claim 1, further comprising, after (B) and prior to (C), determining that the test sample is negative for a copy number variation (CNV) of the sequence of interest.

3. The method of claim 1, further comprising:
repeating (a)-(d) using the re-sequenced sequence reads;
determining that the test sample is outside the exclusion region; and
(F) in response to determining that the re-sequenced test sample is outside the exclusion region, calling the test sample as either having a copy number variation (CNV) of the sequence of interest or not having the CNV of the sequence of interest.

4. The method of claim 1, wherein the fetal fraction LOD curve is obtained based on LODs of affected training samples that are affected by a copy number variation (CNV).

5. The method of claim 1, wherein the detection criterion is X % confident that, for the minimum observed value of the fetal fraction, the corresponding ground truth fetal fraction is larger than a specified LOD needed to detect the affected samples with Y % confidence of detection.

6. The method of claim 5, wherein the X % is about 50%, 55%, 60%, 65%, 70%, 75%, 80%, 85%, 90%, 95%, 99%, or 99.5%.

7. The method of claim 5, wherein the Y % is about 50%, 55%, 60%, 65%, 70%, 75%, 80%, 85%, 90%, 95%, or 99% confidence of detection.

8. The method of claim 5, wherein the X % is 50% and the Y % is 95%.

9. The method of claim 1, wherein the minimum observed value of the fetal fraction is determined as a smallest observed fetal fraction at which Y % of the affected samples can be detected.

10. The method of claim 1, wherein the detection criterion for an observed fetal fraction at an observed coverage is obtained using a distribution of ground truth fetal fractions of the observed fetal fraction at the observed coverage.

11. The method of claim 1, wherein the exclusion region is under the fetal fraction LOD curve.

12. The method of claim 1, wherein the exclusion region is under both the fetal fraction LOD curve and a coverage threshold.

13. The method of claim 1, wherein the observed value of the fetal fraction of the test sample is determined based on sizes of the cell-free nucleic acid fragments.

14. The method of claim 13, wherein the observed value of the fetal fraction of the test sample is determined by:
obtaining a frequency distribution of the sizes of the cell-free nucleic acid fragments; and
applying the frequency distribution to a model relating fetal fraction to frequency of fragment size to obtain the observed value of the fetal fraction.

15. The method of claim 1, wherein the observed value of the fetal fraction of the test sample is determined based on coverage information for bins of the reference genome.

16. The method of claim 15, wherein the observed value of the fetal fraction is calculated by: applying coverage values of a plurality of bins of the reference genome to a model relating fetal fraction to coverage of a bin to obtain the observed value of the fetal fraction.

17. The method of claim 1, wherein the observed value of the fetal fraction of the test sample is determined based on coverage information for bins of a sex chromosome.

18. A computer system for evaluation of copy number of a nucleic acid sequence of interest in a test sample comprising cell-free nucleic acid fragments originating from a mother and a fetus, the system comprising a sequencer and a computer system comprising a processor and one or more computer-readable storage media having stored thereon instructions for execution on said processor, wherein the system is configured to cause:

(A) the sequencer to sequence, at a first depth of sequencing, the test sample;
(B) the computer system to:
  (a) determine an observed value of a fetal fraction of the test sample, wherein the fetal fraction of the test sample indicates a relative amount of fetal origin cell-free nucleic acid fragments in the test sample;
  (b) receive sequence reads obtained by sequencing the cell-free nucleic acid fragments in the test sample;
  (c) align the sequence reads of the cell-free nucleic acid fragments to a reference genome comprising a sequence of interest, thereby providing sequence tags;
  (d) determine a coverage of the sequence tags for at least a portion of the reference genome; and
  (e) determine that the test sample is within an exclusion region based on the coverage of sequences tags determined in (d) and the observed value of the fetal fraction determined in (a), wherein the exclusion region is defined by at least a fetal fraction limit of detection (LOD) curve, wherein the fetal fraction LOD curve varies with coverage values and indicates, for a given coverage value of different coverage values, a minimum observed value of the fetal fraction to achieve a given level of confidence that a corresponding ground truth fetal fraction is greater than a minimum value of fetal fractions needed to achieve a detection criterion; and
(C) the sequencer to re-sequence, at a second depth of sequencing that is greater than the first depth of sequencing, the test sample; and
(D) the computer system to repeat (a)-(d) for the re-sequenced sequence reads;
further comprising: obtaining the LOD curve by:
  (i) selecting from a first plurality of training samples, for each observed fetal fraction of a plurality of observed fetal fractions and for each coverage level of a plurality of coverage levels, one or more selected training samples whose true fetal fractions have the given level of confidence, wherein each training sample comprises cell-free nucleic acid fragments originating from a mother and a fetus,
  (ii) obtaining, using the one or more selected training samples for each observed fetal fraction and each coverage level, true fetal fraction versus observed fetal fraction curves of the plurality of coverage levels,
  (iii) obtaining, using a second plurality of training samples, true fetal fractions having at least the minimum value of fetal fraction needed to achieve the detection criterion for the plurality of coverage levels,
  (iv) obtaining, using the true fetal fraction versus observed fetal fraction curves and the true fetal fractions having at least the minimum value of fetal fraction needed to achieve the detection criterion, a plurality of minimal observed fetal fractions for the plurality of coverage levels required to have the given level of confidence that true fetal fractions have at least the minimum value of fetal fraction needed to achieve the detection criterion, and
  (v) obtaining the fetal fraction LOD curve using the plurality of minimal observed fetal fractions for the plurality of coverage levels.

19. The system of claim 18, wherein the system is further configured to cause:
(E) the computer system to, in response to determining that the re-sequenced test sample is outside the exclusion region, make a call of a copy number variation (CNV) of the sequence of interest.

* * * * *